(12) United States Patent
Goto et al.

(10) Patent No.: US 10,261,417 B2
(45) Date of Patent: Apr. 16, 2019

(54) ACTIVE-LIGHT-SENSITIVE OR RADIATION-SENSITIVE RESIN COMPOSITION, ACTIVE-LIGHT-SENSITIVE OR RADIATION-SENSITIVE FILM AND PATTERN FORMING METHOD, EACH USING COMPOSITION, AND METHOD FOR MANUFACTURING ELECTRONIC DEVICE

(71) Applicant: FUJIFILM Corporation, Tokyo (JP)

(72) Inventors: Akiyoshi Goto, Shizuoka (JP); Michihiro Shirakawa, Shizuoka (JP); Keita Kato, Haibara-gun (JP); Fumihiro Yoshino, Shizuoka (JP); Kei Yamamoto, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/291,538

(22) Filed: Oct. 12, 2016

(65) Prior Publication Data
US 2017/0038685 A1 Feb. 9, 2017

Related U.S. Application Data

(63) Continuation of application No. PCT/JP2015/061278, filed on Apr. 10, 2015.

(30) Foreign Application Priority Data

Apr. 14, 2014 (JP) ................. 2014-083076

(51) Int. Cl.
| | |
|---|---|
| *G03F 7/004* | (2006.01) |
| *G03F 7/039* | (2006.01) |
| *C07C 309/06* | (2006.01) |
| *C07C 381/12* | (2006.01) |
| *G03F 7/16* | (2006.01) |
| *H01L 21/027* | (2006.01) |
| *G03F 7/20* | (2006.01) |
| *G03F 7/32* | (2006.01) |
| *G03F 7/38* | (2006.01) |
| *G03F 7/40* | (2006.01) |

(52) U.S. Cl.
CPC .......... *G03F 7/0397* (2013.01); *C07C 309/06* (2013.01); *C07C 381/12* (2013.01); *G03F 7/0045* (2013.01); *G03F 7/0046* (2013.01); *G03F 7/16* (2013.01); *G03F 7/168* (2013.01); *G03F 7/2006* (2013.01); *G03F 7/2041* (2013.01); *G03F 7/325* (2013.01); *G03F 7/38* (2013.01); *G03F 7/40* (2013.01); *H01L 21/0274* (2013.01)

(58) Field of Classification Search
CPC ...... G03F 7/004; G03F 7/0045; G03F 7/0046; G03F 7/0397; G03F 7/2041; C07C 309/06; C07C 381/12; H01L 21/0274
USPC ............... 430/270.1, 322, 325, 913; 560/149
See application file for complete search history.

(56) References Cited

U.S. PATENT DOCUMENTS

| | | | |
|---|---|---|---|
| 7,235,343 B2 | 6/2007 | Ohsawa et al. | |
| 8,084,188 B2 | 12/2011 | Otsuka et al. | |
| 8,227,183 B2 | 7/2012 | Tsubaki et al. | |
| 8,951,718 B2 | 2/2015 | Tsubaki et al. | |
| 9,291,892 B2 | 3/2016 | Shibuya et al. | |
| 9,291,904 B2 | 3/2016 | Tsubaki et al. | |
| 9,405,197 B2* | 8/2016 | Shibuya ............... | G03F 7/0045 |
| 2004/0229162 A1 | 11/2004 | Ohsawa et al. | |
| 2008/0138742 A1* | 6/2008 | Kodama ............... | C07C 381/12 |
| | | | 430/281.1 |
| 2008/0187860 A1 | 8/2008 | Tsubaki et al. | |
| 2010/0068647 A1 | 3/2010 | Otsuka et al. | |
| 2010/0255419 A1* | 10/2010 | Kodama ............... | C07C 309/06 |
| | | | 430/270.1 |

(Continued)

FOREIGN PATENT DOCUMENTS

| | | |
|---|---|---|
| JP | 2001-114822 A | 4/2001 |
| JP | 2004-138892 A | 5/2004 |

(Continued)

OTHER PUBLICATIONS

Machine translation of JP2004-138892 (no date).*

(Continued)

*Primary Examiner* — Amanda C. Walke
(74) *Attorney, Agent, or Firm* — Sughrue Mion, PLLC

(57) ABSTRACT

An active-light-sensitive or radiation-sensitive resin composition includes a resin (A) and a photoacid generator (B) capable of generating an acid upon irradiation with active light or radiation, in which the active-light-sensitive or radiation-sensitive resin composition contains at least a photoacid generator (B1) represented by the following General Formula (1) and a photoacid generator (B2) other than the photoacid generator (B1) as the photoacid generator (B).

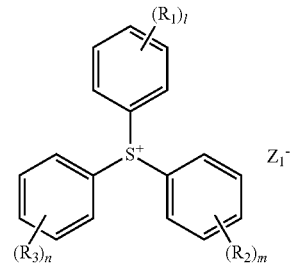

23 Claims, No Drawings

(56) References Cited

U.S. PATENT DOCUMENTS

| | | | |
|---|---|---|---|
| 2011/0117494 A1* | 5/2011 | Ichikawa | C07C 25/18 430/270.1 |
| 2012/0058436 A1 | 3/2012 | Tsubaki et al. | |
| 2012/0315449 A1 | 12/2012 | Tsubaki et al. | |
| 2013/0122427 A1 | 5/2013 | Kataoka et al. | |
| 2014/0287363 A1 | 9/2014 | Shibuya et al. | |
| 2014/0356787 A1* | 12/2014 | Komuro | C07C 381/12 430/281.1 |
| 2015/0072274 A1 | 3/2015 | Tsuchimura et al. | |
| 2015/0079522 A1 | 3/2015 | Tsubaki et al. | |
| 2016/0103395 A1 | 4/2016 | Tsubaki et al. | |

FOREIGN PATENT DOCUMENTS

| | | |
|---|---|---|
| JP | 2004-334060 A | 11/2004 |
| JP | 2008-292975 A | 12/2008 |
| JP | 2010-066631 A | 3/2010 |
| JP | 2010-140014 A | 6/2010 |
| JP | 2011-141494 A | 7/2011 |
| JP | 2012-027436 A | 2/2012 |
| JP | 2013-011857 A | 1/2013 |
| JP | 2013-137339 A | 7/2013 |
| JP | 2013-235253 A | 11/2013 |
| JP | 2014-002359 A | 1/2014 |

OTHER PUBLICATIONS

International Search Report for PCT/JP2015/061278 dated Jun. 16, 2015 [PCT/ISA/210].

Written Opinion for PCT/JP2015/061278 dated Jun. 16, 2015 [PCT/ISA/237].

Office Action for corresponding Taiwanese Application No. 104111797 dated Mar. 17, 2016.

International Preliminary Report on Patentability with translation of Written Opinion dated Oct. 27, 2016, issued by the International Searching Authority in Application No. PCT/JP2015/061278.

Office Action dated Oct. 31 2017, from the Japanese Patent Office in counterpart Japanese Application No. 2016-513766.

Office Action dated May 22, 2018 from the Japanese Patent Office in counterpart Japanese Application No. 2016-513766.

* cited by examiner

ACTIVE-LIGHT-SENSITIVE OR RADIATION-SENSITIVE RESIN COMPOSITION, ACTIVE-LIGHT-SENSITIVE OR RADIATION-SENSITIVE FILM AND PATTERN FORMING METHOD, EACH USING COMPOSITION, AND METHOD FOR MANUFACTURING ELECTRONIC DEVICE

CROSS-REFERENCE TO RELATED APPLICATIONS

This application is a Continuation Application of PCT Application No. PCT/JP2015/061278, filed Apr. 10, 2015, and based upon and claiming the benefit of priority from Japanese Patent Application No. 2014-083076, filed Apr. 14, 2014, the entire contents of all of which are incorporated herein by reference.

BACKGROUND OF THE INVENTION

1. Field of the Invention

The present invention relates to an active-light-sensitive or radiation-sensitive resin composition, an active-light-sensitive or radiation-sensitive film and a pattern forming method, each using the composition, a method for manufacturing an electronic device, and an electronic device. More specifically, the present invention relates to an active-light-sensitive or radiation-sensitive resin composition which is suitably used for a process for manufacturing a semiconductor such as an IC, a process for manufacture of liquid crystals and a circuit board for a thermal head or the like, other photofabrication processes, a planographic printing plate, or an acid curable composition; an active-light-sensitive or radiation-sensitive film and a pattern forming method, each using the composition; and a method for manufacturing an electronic device and an electronic device.

2. Description of the Related Art

Since a resist for a KrF excimer laser (248 nm) was developed, an image forming method called chemical amplification has been used as an image forming method of a resist in order to complement desensitization caused by light absorption. By way of san example of an image forming method with positive type chemical amplification, the method is an image forming method in which an acid generating agent in an exposed area decomposes by exposure with excimer laser, electron beams, extreme ultraviolet rays, or the like to produce an acid, the generated acid is used as a reaction catalyst during post exposure bake (PEB) after the exposure to change alkali-insoluble groups to alkali-soluble groups, and the exposed area is removed by an alkali developer. Currently, various alkaline developers have been suggested as an alkaline developer, but water-based alkaline developers with 2.38% by mass of an aqueous tetramethylammonium hydroxide solution (TMAH) is universally used.

Moreover, in order to make semiconductor elements finer, the wavelength of an exposure light source has been shortened and a projection lens with a high numerical aperture (high NA) has been advanced. Thus, an exposure machine using an ArF excimer laser having a wavelength of 193 nm as a light source has been currently developed. In addition, as a technique for further improving resolving power, a so-called liquid immersion method in which a liquid having a high refractive index (hereinafter also referred to as an "immersion liquid") is filled between a projection lens and a sample; EUV lithography that performs exposure with ultraviolet rays at a shorter wavelength (13.5 nm); and the like have been proposed from the related art.

Various compounds have been developed as a photoacid generator which is the main constituent of a chemical amplification resist composition. For example, JP2013-137339A discloses a technique for forming a positive tone pattern by a liquid immersion method employing ArF excimer laser as a light source, by using a chemical amplification type resist composition containing two specific kinds of photoacid generators.

On the other hand, a negative tone pattern forming method using a developer including an organic solvent (hereinafter referred to as an "organic solvent developer") has recently been developed, in addition to a positive tone pattern forming method (see, for example, JP2008-292975A and JP2011-141494A). For example, in JP2011-141494A, in pattern formation by alkali development using a negative type resist composition in the related art, a chemical amplification type resist composition to which a specific compound including at least one of a fluorine atom or a silicon atom had been added is used in a negative tone pattern forming method using a developer including an organic solvent, taking into consideration a demand for further improvement of line width roughness (LWR), depth of focus (DOF), and other performance, each of which is presumed to be due to swelling during the development.

However, in the current situation, it is highly difficult to discover an appropriate combination of a resist composition, a developer, a rinsing liquid, and the like, which is required to form a pattern having comprehensively good performance, and there is a demand for further improvement. In particular, there is a demand for improvement of performance of line width roughness (LWR) as well as depth of focus (DOF) as the line width of resolution of the resist becomes finer.

SUMMARY OF THE INVENTION

Taking into consideration the background art, the present invention has an object to provide an active-light-sensitive or radiation-sensitive resin composition having excellent pattern roughness properties such as LWR and excellent depth of focus (DOF), an active-light-sensitive or radiation-sensitive film and a pattern forming method, each using the composition, and a method for manufacturing an electronic device, and an electronic device.

In one aspect, the present invention is as follows.

[1] An active-light-sensitive or radiation-sensitive resin composition comprising:

a resin (A); and a photoacid generator (B) capable of generating an acid upon irradiation with active light or radiation, in which the active-light-sensitive or radiation-sensitive resin composition contains at least a photoacid generator (B1) represented by the following General Formula (1) and a photoacid generator (B2) other than the photoacid generator (B1) as the photoacid generator (B):

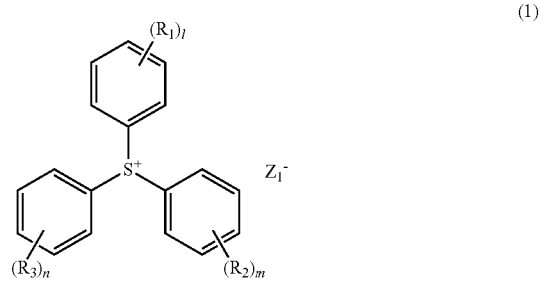

In General Formula (1), $R_1$, $R_2$, and $R_3$ each independently represent a halogen atom, an alkyl group, a cycloalkyl group, an alkoxy group, an alkylcarbonyloxy group, an alkyloxycarbonyl group, an alkylthio group, a cycloalkylcarbonyloxy group, a cycloalkyloxycarbonyl group, or a cycloalkylthio group;

l, m, and n each independently represent an integer of 0 to 3, and l+m+n is 1 or more. When l is 2 or more, a plurality of $R_1$'s may be the same as or different from each other, and at least two $R_1$'s may be bonded to each other to form a ring. When m is 2 or more, a plurality of $R_2$'s may be the same as or different from each other, and at least two $R_2$'s may be bonded to each other to form a ring. When n is 2 or more, a plurality of $R_3$'s may be the same as or different from each other, and at least two $R_3$'s may be bonded to each other to form a ring; and $Z_1^-$ represents a non-nucleophilic anion.

[2] The active-light-sensitive or radiation-sensitive resin composition as described in [1], in which the photoacid generator (B2) is a compound represented by the following General Formula (ZI-3) or the following General Formula (ZI-4):

$$\text{(ZI-3)}$$

In General Formula (ZI-3), $R_1$ represents an alkyl group, a cycloalkyl group, an alkoxy group, a cycloalkoxy group, an aryl group, or an alkenyl group;

$R_2$ and $R_3$ each independently represent a hydrogen atom, an alkyl group, a cycloalkyl group, or an aryl group, and $R_2$ and $R_3$ may be linked to each other to form a ring;

$R_1$ and $R_2$ may be linked to each other to form a ring;

$R_x$ and $R_y$ each independently represent an alkyl group, a cycloalkyl group, an alkenyl group, an aryl group, a 2-oxoalkyl group, a 2-oxocycloalkyl group, an alkoxycarbonylalkyl group, or an alkoxycarbonylcycloalkyl group. $R_X$ and $R_y$ may be linked to each other to form a ring, and this ring structure may include an oxygen atom, a nitrogen atom, a sulfur atom, a ketone group, an ether bond, an ester bond, or an amide bond; and $Z^-$ represents a non-nucleophilic anion.

$$\text{(ZI-4)}$$

In General Formula (ZI-4), $R_{13}$ represents a hydrogen atom, a fluorine atom, a hydroxyl group, an alkyl group, a cycloalkyl group, an alkoxy group, an alkoxycarbonyl group, or a group having a cycloalkyl group;

in the case where $R_{14}$'s are present in plural numbers, they each independently represent a hydroxyl group, an alkyl group, a cycloalkyl group, an alkoxy group, an alkoxycarbonyl group, an alkylcarbonyl group, an alkylsulfonyl group, a cycloalkylsulfonyl group, or a group having a cycloalkyl group;

$R_{15}$'s each independently represent an alkyl group, a cycloalkyl group, or a naphthyl group. Two $R_{15}$'s may be bonded to each other to form a ring together with a sulfur atom in the formula, and may further include a hetero atom, in addition to a sulfur atom in the formula, as an atom constituting the ring;

l represents an integer of 0 to 2;

r represents an integer of 0 to 8; and $Z^-$ represents a non-nucleophilic anion.

[3] The active-light-sensitive or radiation-sensitive resin composition as described in [2], in which $Z^-$ in General Formula (ZI-3) or $Z^-$ in General Formula (ZI-4) is a non-nucleophilic anion represented by the following General Formula (2):

$$\text{(2)}$$

In General Formula (2),

Xf's each independently represent a fluorine atom or an alkyl group substituted with at least one fluorine atom;

$R_{16}$ and $R_{17}$ each independently represent a hydrogen atom, a fluorine atom, an alkyl group, or an alkyl group substituted with at least one fluorine atom, and in the case where $R_{16}$ and $R_{17}$ are present in plural numbers, they may be the same as or different from each other;

L represents a divalent linking group, and in the case where L's are present in plural numbers, they may be the same as or different from each other;

W represents an organic group including a cyclic structure;

o represents an integer of 1 to 20;

p represents an integer of 0 to 10; and q represents an integer of 0 to 10.

[4] The active-light-sensitive or radiation-sensitive resin composition as described in any one of [1] to [3], in which $Z_1^-$ in General Formula (1) is a non-nucleophilic anion represented by the following General Formula (2):

$$\text{(2)}$$

In General Formula (2),

Xf's each independently represent a fluorine atom or an alkyl group substituted with at least one fluorine atom;

$R_{16}$ and $R_{17}$ each independently represent a hydrogen atom, a fluorine atom, an alkyl group, or an alkyl group substituted with at least one fluorine atom, and in the case where $R_{16}$ and $R_{17}$ are present in plural numbers, they may be the same as or different from each other;

L represents a divalent linking group, and in the case where L's are present in plural numbers, they may be the same as or different from each other;

W represents an organic group including a cyclic structure;

o represents an integer of 1 to 20;

p represents an integer of 0 to 10; and q represents an integer of 0 to 10.

[5] The active-light-sensitive or radiation-sensitive resin composition as described in any one of [1] to [4], in which the content of the photoacid generator (B) is 10% by mass or more with respect to the total solid content in the composition.

[6] The active-light-sensitive or radiation-sensitive resin composition as described in any one of [1] to [5], in which the resin (A) is a resin which decomposes by the action of an acid to increase the polarity thereof.

[7] The active-light-sensitive or radiation-sensitive resin composition as described in any one of [1] to [6], further comprising a basic compound having a nitrogen atom or a basic compound whose basicity decreases or is lost upon irradiation with active light or radiation.

[8] An active-light-sensitive or radiation-sensitive film formed by using the active-light-sensitive or radiation-sensitive resin composition as described in any one of [1] to [7].

[9] A pattern forming method comprising:

a step of forming an active-light-sensitive or radiation-sensitive film using the active-light-sensitive or radiation-sensitive resin composition as described in any one of [1] to [7];

a step of exposing the active-light-sensitive or radiation-sensitive film; and a step of developing the exposed active-light-sensitive or radiation-sensitive film.

[10] The pattern forming method as described in [9], in which the exposing step is liquid immersion exposure.

[11] The pattern forming method as described in [9] or [10], in which the developer used in the developing step is a developer containing an organic solvent.

[12] A method for manufacturing an electronic device, comprising the pattern forming method as described in any one of [9] to [11].

[13] An electronic device manufactured by the method for manufacturing an electronic device as described in [12].

According to the present invention, it is possible to provide an active-light-sensitive or radiation-sensitive resin composition having excellent pattern roughness properties such as LWR and excellent depth of focus (DOF), an active-light-sensitive or radiation-sensitive film and a pattern forming method, each using the composition, a method for manufacturing an electronic device, and an electronic device.

DESCRIPTION OF THE PREFERRED EMBODIMENTS

Hereinafter, embodiments of the present invention will be described in detail.

In citations for a group (atomic group) in the present specification, in the case where the group is denoted without specifying whether it is substituted or unsubstituted, the group includes both a group not having a substituent and a group having a substituent. For example, an "alkyl group" includes not only an alkyl group not having a substituent (unsubstituted alkyl group), but also an alkyl group having a substituent (substituted alkyl group).

In the present invention, "active light" or "radiation" means, for example, a bright line spectrum of a mercury lamp or the like, far ultraviolet rays represented by an excimer laser, extreme ultraviolet rays (EUV light), X-rays, electron beams (EB), or the like. In addition, in the present invention, light means active light or radiation.

Furthermore, unless otherwise specified, "exposure" in the present specification includes not only exposure by a mercury lamp, far ultraviolet rays represented by an excimer laser, extreme ultraviolet rays, X-rays, EUV light, or the like, but also writing by particle rays such as electron beams and ion beams.

Moreover, in the present specification, "(a value) to (a value)" is used to mean a range including the numeral values described before and after "to" as a lower limit value and an upper limit value, respectively.

In addition, in the present specification, "(meth)acrylate" represents acrylate and methacrylate, and "(meth)acryl" represents acryl and methacryl.

[Active-Light-Sensitive or Radiation-Sensitive Resin Composition]

Hereinafter, the resin (A) and the photoacid generator (B) capable of generating an acid upon irradiation with active light or radiation, which are contained in the active-light-sensitive or radiation-sensitive resin composition of the present invention (hereinafter also referred to as "the composition of the present invention"), and optional components which may be contained in the composition will be described.

The active-light-sensitive or radiation-sensitive resin composition of the present invention is preferably used for ArF exposure, and more preferably for ArF liquid immersion exposure.

The active-light-sensitive or radiation-sensitive resin composition of the present invention may be used for forming a negative tone pattern by using an organic solvent developer, or may also be used for forming a positive tone pattern by using an alkali developer. However, in the case where the composition is used for forming a negative tone pattern by using an organic solvent developer, an effect of improving LWR and DOF by the present invention is particularly significant. In addition, the composition according to the present invention is typically a chemical amplification type resist composition.

<Photoacid Generator (B) Capable of Generating Acid Upon Irradiation with Active Light or Radiation>

The composition of the present invention contains at least a photoacid generator (B1) represented by General Formula (1) shown below and a photoacid generator (B2) other than the photoacid generator (B1) as the photoacid generator (B) capable of generating an acid upon irradiation with active light or radiation (hereinafter also referred to as a "photoacid generator" or a "compound (B)").

[Photoacid Generator (B1)]

The photoacid generator (B1) is a compound represented by the following General Formula (1).

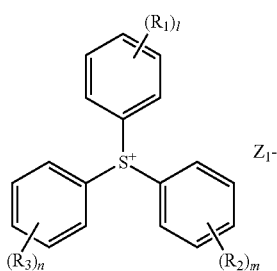
(1)

In General Formula (1), $R_1$, $R_2$, $R_3$ each independently represent a halogen atom, an alkyl group, a cycloalkyl group, an alkoxy group, an alkylcarbonyloxy group, an alkyloxycarbonyl group, an alkylthio group, a cycloalkylcarbonyloxy group, a cycloalkyloxycarbonyl group, or a cycloalkylthio group.

l, m, and n each independently represent an integer of 0 to 3. When l is 2 or more, a plurality of $R_1$'s may be the same as or different from each other, and at least two $R_1$ may be bonded to each other to form a ring. When m is 2 or more, a plurality of $R_2$'s may be the same as or different from each other and at least two $R_2$'s may be bonded to each other to form a ring. When n is 2 or more, a plurality of $R_3$'s may be the same as or different from each other, and at least two $R_3$'s may be bonded to each other to form a ring. l+m+n is 1 or more.

$Z_1^-$ represents a non-nucleophilic anion.

Hereinafter, General Formula (1) will be described in detail.

Examples of the halogen atom as $R_1$, $R_2$, and $R_3$ include a fluorine atom, a chlorine atom, and a bromine atom.

The alkyl group as $R_1$, $R_2$, and $R_3$ may be linear or branched, and may have a substituent. Further, the carbon atom included in alkyl group may be substituted with carbonyl carbon. As the alkyl group, for example, an alkyl group having 1 to 20 carbon atoms is preferable, and an alkyl group having 1 to 10 carbon atoms is more preferable. Specific examples thereof include linear alkyl groups such as a methyl group, an ethyl group, an n-propyl group, an n-butyl group, an n-pentyl group, an n-hexyl group, an n-octyl group, an n-dodecyl group, an n-tetradecyl group, and an n-octadecyl group, and branched alkyl groups such as an isopropyl group, an isobutyl group, a t-butyl group, a neopentyl group, and a 2-ethylhexyl group. Examples of the substituent which the alkyl group may have include a fluorine atom, an alkoxy group, and a hydroxyl group.

The cycloalkyl group as $R_1$, $R_2$, and $R_3$ may be monocyclic or polycyclic, and may have a substituent. For example, the cycloalkyl group is preferably a cycloalkyl group having 3 to 20 carbon atoms, and more preferably a cycloalkyl group having 3 to 10 carbon atoms. Specific examples thereof include a cyclopropyl group, a cyclopentyl group, a cyclohexyl group, a norbornyl group, and an adamantyl group. Further, the cycloalkyl group may include a hetero atom such as an oxygen atom, a sulfur atom, and a nitrogen atom, and may be, for example, a tetrahydropyran ring, a lactone ring, or a cyclic ketone ring. In addition, the carbon atom included in the cycloalkyl group may be substituted with carbonyl carbon.

Examples of the substituent which the cycloalkyl group may have include an alkyl group, a trifluoromethyl group, an alkoxy group, and a hydroxyl group.

The alkoxy group as $R_1$, $R_2$, and $R_3$ may be linear or branched, or may be cyclic, and may have a substituent. For example, the alkoxy group is preferably an alkoxy group having 1 to 20 carbon atoms, and more preferably an alkoxy group having 1 to 10 carbon atoms. Specific examples thereof include a methoxy group, an ethoxy group, an isopropyloxy group, a t-butyloxy group, a t-amyloxy group, and an n-butyloxy group. Examples of the substituent which the alkoxy group may have are the same specific examples as the aforementioned substituents which the alkyl group or the cycloalkyl group may have.

The alkyl group included in the alkylcarbonyloxy group as $R_1$, $R_2$, and $R_3$ has the same definition as the alkyl group as $R_1$, $R_2$, and $R_3$ as described above, and specific examples thereof are also the same.

The alkoxy group included in the alkyloxycarbonyl group as $R_1$, $R_2$, and $R_3$ has the same definition as the alkoxy group as $R_1$, $R_2$, and $R_3$ as described above, and specific examples thereof are also the same.

The alkyl group included in the alkylthio group as $R_1$, $R_2$, and $R_3$ has the same definition as the alkyl group as $R_1$, $R_2$, and $R_3$ as described above, and specific examples thereof are also the same.

The cycloalkyl group included in the cycloalkylcarbonyloxy group, the cycloalkyloxycarbonyl group, and the cycloalkylthio group as $R_1$, $R_2$, and $R_3$ has the same definition as the cycloalkyl group as $R_1$, $R_2$, and $R_3$ as described above, and specific examples thereof are also the same.

In order to maximize the effects exerted by the present invention, at least one of $R_1$, $R_2$, or $R_3$ is preferably an alkoxy group or an alkylthio group, more preferably an alkoxy group, and particularly preferably a methoxy group.

In one aspect of the present invention, l is preferably an integer of 1 to 3, m is preferably an integer of 0 to 3, and n is preferably an integer of 0 to 3. l+m+n is preferably an integer of 1 to 3.

Examples of the non-nucleophilic anion represented by $Z_1^-$ include a sulfonic acid anion, a carboxylic acid anion, a sulfonylimide anion, a bis(alkylsulfonyl)imide anion, and a tris(alkylsulfonyl)methyl anion.

The non-nucleophilic anion is an anion having an extremely low ability of causing a nucleophilic reaction, which can suppress the decomposition with aging due to an intramolecular nucleophilic reaction. With this anion, the temporal stability of the composition is improved.

Examples of the sulfonic acid anion include an aliphatic sulfonic acid anion, an aromatic sulfonic acid anion, and a camphorsulfonic acid anion.

Examples of the carboxylic acid anion include an aliphatic carboxylic acid anion, an aromatic carboxylic acid anion, and an aralkylcarboxylic acid anion.

The aliphatic moiety in the aliphatic sulfonic acid anion and the aliphatic carboxylic acid anion may be an alkyl group, or a cycloalkyl group, and preferred examples thereof include an alkyl group having 1 to 30 carbon atoms or a cycloalkyl group having 3 to 30 carbon atoms and preferred examples of the aromatic group in the aromatic sulfonic acid anion and the aromatic carboxylic acid anion include an aryl group having 6 to 14 carbon atoms, for example, a phenyl group, a tolyl group, and a naphthyl group.

The alkyl group, the cycloalkyl group, and the aryl group in the aliphatic sulfonic acid anion and the aromatic sulfonic acid anion may have a substituent.

Examples of the other non-nucleophilic anions include fluorinated phosphorus (for example, $PF_6^-$), fluorinated boron (for example, $BF_4^-$), and fluorinated antimony (for example, $SbF_6^-$).

The non-nucleophilic anion of $Z_1^-$ is preferably an aliphatic sulfonic acid anion substituted with a fluorine atom at least at the α-position of sulfonic acid, an aromatic sulfonic acid anion substituted with a fluorine atom or a group having a fluorine atom, a bis(alkylsulfonyl)imide anion in which the alkyl group is substituted with a fluorine atom, or a tris(alkylsulfonyl)methide anion in which the alkyl group is substituted with a fluorine atom. The non-nucleophilic anion is more preferably a perfluoroaliphatic sulfonic acid anion having 4 to 8 carbon atoms or a benzenesulfonic acid anion having a fluorine atom, still more preferably a nonafluorobutanesulfonic acid anion, a perfluorooctanesulfonic acid anion, a pentafluorobenzenesulfonic acid anion, or a 3,5-bis(trifluoromethyl)benzenesulfonic acid anion.

The non-nucleophilic anion of $Z_1^-$ is preferably represented by General Formula (2). In this case, it is presumed that the volume of the generated acid is large and the diffusion of the acid is inhibited, and therefore, the improvement of exposure latitude is further promoted.

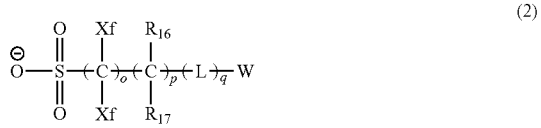

(2)

In General Formula (2),

Xf's each independently represent a fluorine atom or an alkyl group substituted with at least one fluorine atom.

$R_{16}$ and $R_{17}$ each independently represent a hydrogen atom, a fluorine atom, an alkyl group, or an alkyl group substituted with at least one fluorine atom, and in the case where $R_{16}$ and $R_{17}$ are present in plural numbers, they may be the same as or different from each other.

L represents a divalent linking group, and in the case where L's are present in plural numbers, they may be the same as or different from each other.

W represents an organic group including a cyclic structure.

o represents an integer of 1 to 20. p represents an integer of 0 to 10. q represents an integer of 0 to 10.

The anion of General Formula (2) will be described in more detail.

Xf is a fluorine atom or an alkyl group substituted with at least one fluorine atom as described above, and as an alkyl group in the alkyl group substituted with a fluorine atom, an alkyl group having 1 to 10 carbon atoms is preferable, and an alkyl group having 1 to 4 carbon atoms is more preferable. Further, the alkyl group substituted with a fluorine atom of Xf is preferably a perfluoroalkyl group.

Xf is preferably a fluorine atom or a perfluoroalkyl group having 1 to 4 carbon atoms. Specific examples thereof include a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$, and among these, a fluorine atom and $CF_3$ are preferable. It is particularly preferable that both Xf's are fluorine atoms.

$R_{16}$ and $R_{17}$ each represent a hydrogen atom, a fluorine atom, an alkyl group, or an alkyl group substituted with at least one fluorine atom as described above, and the alkyl group is preferably an alkyl group having 1 to 4 carbon atoms, and more preferably a perfluoroalkyl group having 1 to 4 carbon atoms. Specific examples of the alkyl group substituted with at least one fluorine atom in $R_{16}$ and $R_{17}$ include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$, and among these, $CF_3$ is preferable.

L represents a divalent linking group, —COO—, —OCO—, —CO—, —O—, —S—, —SO—, —SO$_2$—, —N(Ri)- (in the formula, Ri represents a hydrogen atom or alkyl), an alkylene group (preferably an alkyl group having 1 to 6 carbon atoms, more preferably an alkyl group having 1 to 4 carbon atoms, particularly preferably a methyl group or an ethyl group, and most preferably a methyl group), a cycloalkylene group (preferably having 3 to 10 carbon atoms), an alkenylene group (preferably having 2 to 6 carbon atoms), or a divalent linking group formed by combination of these plurality of groups. L is preferably —COO—, —OCO—, —CO—, —SO$_2$—, —CON(Ri)-, —SO$_2$N(Ri)-, —CON(Ri)-alkylene group-, —N(Ri)CO-alkylene group-, —COO-alkylene group-, or —OCO-alkylene group-, and more preferably —SO$_2$—, —COO—, —OCO—, —COO-alkylene group-, or —OCO-alkylene group-. As the alkylene group in —CON(Ri)-alkylene group-, —N(Ri)CO-alkylene group-, —COO-alkylene group-, —OCO-alkylene group-, an alkylene group having 1 to 20 carbon atoms is preferable, and an alkylene group having 1 to 10 carbon atoms is more preferable. In the case where L's are present in plural numbers, they may be the same as or different from each other.

Specific examples and preferred examples of the alkyl group for Ri are the same as the aforementioned specific examples and preferred examples as $R_1$ to $R_3$ in General Formula (1).

The organic group including a cyclic structure of W is not particularly limited as long as it has a cyclic structure, and examples thereof include structures with an alicyclic group, an aryl group, a heterocyclic group (including not only an aromatic heterocyclic group but also a non-aromatic heterocyclic group, for example, a tetrahydropyran ring, a lactone ring structure, and a sultone ring).

The alicyclic group may be monocyclic or polycyclic, and it is preferably a monocyclic cycloalkyl group such as a cyclopentyl group, a cyclohexyl group, and a cyclooctyl group, and a polycyclic cycloalkyl group such as a norbornyl group, a norbornenyl group, a tricyclodecanyl group (for example, a tricyclo[5.2.1.0(2,6)]decanyl group), a tetracyclodecanyl group, a tetracyclododecanyl group, and an adamantyl group, and particularly preferably an adamantyl group. Further, a nitrogen atom-containing alicyclic group such as a piperidine group, a decahydroquinoline group, and a decahydroisoquinoline group is preferable. Among these, an alicyclic group having a bulky structure having 7 or more carbon atoms, such as a norbornyl group, a tricyclodecanyl group, a tetracyclodecanyl group, a tetracyclododecanyl group, an adamantyl group, a decahydroquinoline group, and a decahydroisoquinoline group is preferable from the viewpoints of suppressing diffusion in a film in a post exposure baking (PEB) step, and improving exposure latitude. Among these, an adamantyl group and a decahydroisoquinoline group are particularly preferable.

Examples of the aryl group include a benzene ring group, a naphthalene ring group, a phenanthrene ring group, and an anthracene ring group. Among these, naphthalene having a low light absorbance is preferable from the viewpoint of the light absorbance at 193 nm.

Examples of the heterocyclic group include a furan ring, a thiophene ring, a benzofuran ring, a benzothiophene ring, a dibenzofuran ring, a dibenzothiophene ring, and a piperidine ring. Among these, a furan ring, a thiophene ring, and a pyridine ring are preferable. Examples of other preferred heterocyclic group include the structures shown below (in the formulae, X represents a methylene group or an oxygen atom, and R represents a monovalent organic group).

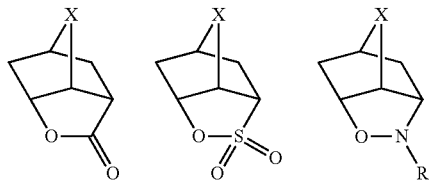

The cyclic organic group may have a substituent, and examples of its substituent include an alkyl group (which may be linear, branched, or cyclic, and preferably has 1 to 12 carbon atoms), an aryl group (having 6 to 14 carbon atoms), a hydroxy group, an alkoxy group, an ester group, an amide group, a urethane group, a ureido group, a thioether group, a sulfonamide group, and sulfonic acid ester group.

Moreover, carbon constituting an organic group including a cyclic structure (carbon contributing ring formation) may be carbonyl carbon.

o is preferably 1 to 8, more preferably 1 to 4, and particularly preferably 1. p is preferably 0 to 4, more preferably 0 or 1, and particularly preferably 1. q is preferably 0 to 8, more preferably 0 to 4, and still more preferably 1.

Furthermore, in other aspects of the present invention, the non-nucleophilic anion of $Z_1^-$ may be a disulfonylimidic acid anion.

As the disulfonylimidic acid anion, a bis(alkylsulfonyl) imide anion is preferable.

The alkyl group in the bis(alkylsulfonyl)imide anion is preferably an alkyl group having 1 to 5 carbon atoms.

Two alkyl groups in the bis(alkylsulfonyl)imide anion may be linked to each other to form an alkylene group (preferably having 2 to 4 carbon atoms), or may form a ring together with an imide group and two sulfonyl groups. As the ring structure which the bis(alkylsulfonyl)imide anion may form, a 5- to 7-membered ring is preferable, and a 6-membered ring is more preferable.

Examples of the substituent which the alkylene group formed by the mutual linking of an alkyl group, and two alkyl groups may have include a halogen atom, an alkyl group substituted with a halogen atom, an alkoxy group, an alkylthio group, an alkyloxysulfonyl group, an aryloxysulfonyl group, and a cycloalkylaryloxysulfonyl group, and the fluorine atom or the alkyl group substituted with a fluorine atom is preferable.

From the viewpoint of the acid strength, the non-nucleophilic anion of $Z_1^-$ preferably has a pKa of the generated acid of −1 or less in order to improve the sensitivity.

The non-nucleophilic anion of $Z_1^-$ has a fluorine content represented by (sum of mass of all the fluorine atoms included in the anion)/(sum of mass of all the atoms included in the anion) of preferably 0.25 or less, more preferably 0.20 or less, and still more preferably 0.15 or less.

[Photoacid Generator (B2)]

The photoacid generator (B2) is a photoacid generator which is different from the photoacid generator (B1) as described above. In one aspect of the present invention, the photoacid generator (B2) is preferably an ionic compound having a cation structure from that of the photoacid generator (B1) represented by General Formula (1). Further, in another aspect, the photoacid generator (B2) is more preferably an ionic compound which has a cation structure different from that of the photoacid generator (B1) represented by General Formula (1), and has the same anion structure as that of the photoacid generator (B1).

The photoacid generator (B2) is, for example, a compound represented by General Formula (ZI-3) or General Formula (ZI-4).

First, the compound represented by the General Formula (ZI-3) will be described.

(ZI-3)

In General Formula (ZI-3), $R_1$ represents an alkyl group, a cycloalkyl group, an alkoxy group, a cycloalkoxy group, an aryl group, or an alkenyl group. These groups may have a substituent.

$R_2$ and $R_3$ each independently represent a hydrogen atom, an alkyl group, a cycloalkyl group, or an aryl group, and $R_2$ and $R_3$ may be linked to each other to form a ring. These groups may have a substituent.

$R_1$ and $R_2$ may be linked to each other to form a ring structure.

$R_X$ and $R_y$ each independently represent an alkyl group, a cycloalkyl group, an alkenyl group, an aryl group, a 2-oxoalkyl group, a 2-oxocycloalkyl group, an alkoxycarbonylalkyl group, or an alkoxycarbonylcycloalkyl group. These groups may have a substituent. $R_X$ and $R_y$ may be linked to each other to form a ring structure, and this ring structure may include an oxygen atom, a nitrogen atom, a sulfur atom, a ketone group, an ether bond, an ester bond, or an amide bond.

$Z^-$ represents a non-nucleophilic anion.

General Formula (ZI-3) will be described in detail.

The alkyl group as $R_1$ preferably a linear or branched alkyl group having 1 to 20 carbon atoms, and may have an oxygen atom, a sulfur atom, or a nitrogen atom in the alkyl chain. Specific examples thereof include linear alkyl groups such as a methyl group, an ethyl group, an n-propyl group, an n-butyl group, an n-pentyl group, an n-hexyl group, an n-octyl group, an n-dodecyl group, an n-tetradecyl group, and an n-octadecyl group, and branched alkyl groups such as an isopropyl group, an isobutyl group, a t-butyl group, a neopentyl group, and a 2-ethylhexyl group. The alkyl group of $R_1$ may have a substituent, and examples of the alkyl group having a substituent include a cyanomethyl group, a 2,2,2-trifluoroethyl group, a methoxycarbonylmethyl group, and an ethoxycarbonylmethyl group.

The cycloalkyl group as $R_1$ is preferably a cycloalkyl group having 3 to 20 carbon atoms, and may have an oxygen atom or a sulfur atom in the ring. Specific examples thereof include a cyclopropyl group, a cyclopentyl group, a cyclohexyl group, a norbornyl group, and an adamantyl group. The cycloalkyl group of $R_1$ may have a substituent, and examples of the substituent include an alkyl group and an alkoxy group.

The alkoxy group as $R_1$ is preferably an alkoxy group having 1 to 20 carbon atoms. Specific examples thereof include a methoxy group, an ethoxy group, an isopropyloxy group, a t-butyloxy group, a t-amyloxy group, and an n-butyloxy group. The alkoxy group as $R_1$ may have a substituent, and examples of the substituent include an alkyl group and a cycloalkyl group.

The cycloalkoxy group as $R_1$ preferably a cycloalkoxy group having 3 to 20 carbon atoms, and examples thereof include a cyclohexyloxy group, a norbornyloxy group, and an adamantyloxy group. The cycloalkoxy group of $R_1$ may have a substituent, and examples of the substituent include an alkyl group and a cycloalkyl group.

The aryl group as $R_1$ is preferably an aryl group having 6 to 14 carbon atoms, and examples thereof include a phenyl group, a naphthyl group, and a biphenyl group. The aryl group of $R_1$ may have a substituent, and preferred examples of the substituent include an alkyl group, a cycloalkyl group, an alkoxy group, a cycloalkoxy group, an aryloxy group, an alkylthio group, and an arylthio group. In the case where the substituent is an alkyl group, a cycloalkyl group, an alkoxy group, or a cycloalkoxy group, examples thereof are the same as those for the alkyl group, the cycloalkyl group, the alkoxy group, and the cycloalkoxy group as $R_1$.

Examples of the alkenyl group as $R_1$ include a vinyl group and an allyl group.

$R_2$ and $R_3$ represent a hydrogen atom, an alkyl group, a cycloalkyl group, or an aryl group, and $R_2$ and $R_3$ may be linked to each other to form a ring. However, at least one of $R_2$ or $R_3$ represents an alkyl group, a cycloalkyl group, or an aryl group. Specific and preferred examples of the alkyl group, the cycloalkyl group, and the aryl group for $R_2$ or $R_3$ are the same specific and preferred examples as described above for $R_1$. In the case where $R_2$ and $R_3$ are linked to each other to form a ring, the total number of carbon atoms contributing to formation of a ring included in $R_2$ and $R_3$ is preferably 4 to 7, and particularly preferably 4 or 5.

$R_1$ and $R_2$ may be linked to each other to form a ring structure. In the case where $R_1$ and $R_2$ are linked to each other to form a ring, it is preferable that $R_1$ is an aryl group (preferably a phenyl group having a substituent or a naphthyl group) and $R_2$ is an alkylene group having 1 to 4 carbon atoms (preferably a methylene group or an ethylene group), and preferred examples of the substituent include the same ones as the substituent which the aryl group as $R_1$ may have. In another aspect of the case where $R_1$ and $R_2$ are linked to each other to form a ring, it is also preferable that $R_1$ is a vinyl group and $R_2$ is an alkylene group having 1 to 4 carbon atoms.

The alkyl group represented by $R_X$ and $R_Y$ is preferably an alkyl group having 1 to 15 carbon atoms, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

The cycloalkyl group represented by $R_X$ and $R_Y$ is preferably a cycloalkyl group having 3 to 20 carbon atoms, and examples thereof include a cyclopropyl group, a cyclopentyl group, a cyclohexyl group, a norbornyl group, and an adamantyl group.

The alkenyl group represented by $R_X$ and $R_Y$ is preferably an alkenyl group having 2 to 30 carbon atoms, and examples thereof include a vinyl group, an allyl group, and a styryl group.

The aryl group represented by $R_X$ and $R_Y$ is preferably, for example, an aryl group having 6 to 20 carbon atoms, and specific examples thereof include a phenyl group, a naphthyl group, an azulenyl group, an acenaphthylenyl group, a phenanthrenyl group, a phenalenyl group, a phenanthracenyl group, a fluorenyl group, anthracenyl group, a pyrenyl group, and a benzopyrenyl group. The aryl group is preferably a phenyl group or a naphthyl group, and more preferably a phenyl group.

Examples of the alkyl group moiety of the 2-oxoalkyl group and the alkoxycarbonylalkyl group represented by $R_X$ and $R_Y$ include those enumerated above as $R_X$ and $R_Y$.

Examples of the cycloalkyl group moiety in the 2-oxocycloalkyl group and the alkoxycarbonylcycloalkyl group represented by $R_X$ and $R_Y$ include those enumerated above as $R_X$ and $R_Y$.

Examples of $Z^-$ include those enumerated as $Z_1^-$ in General Formula (1). In one aspect of the present invention, $Z^-$ is more preferably the same as the anion structure $(Z_1^-)$ in the acid generator (B1), and even more preferably the non-nucleophilic anion represented by General Formula (2).

Next, a compound represented by General Formula (ZI-4) will be described.

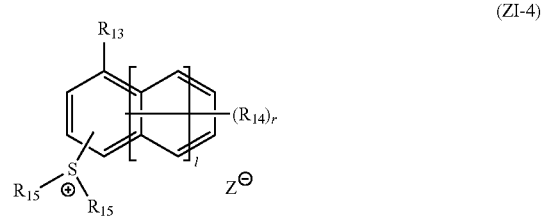

(ZI-4)

In General Formula (ZI-4), $R_{13}$ represents a hydrogen atom, a fluorine atom, a hydroxyl group, an alkyl group, a cycloalkyl group, an alkoxy group, an alkoxycarbonyl group, or a group having a cycloalkyl group. These groups may have a substituent.

In the case where $R_{14}$'s are present in plural numbers, they each independently represent a hydroxyl group, an alkyl group, a cycloalkyl group, an alkoxy group, an alkoxycarbonyl group, an alkylcarbonyl group, an alkylsulfonyl group, a cycloalkylsulfonyl group, or a group having a cycloalkyl group. These groups may have a substituent.

$R_{15}$'s each independently represent an alkyl group, a cycloalkyl group, or a naphthyl group. Two $R_{15}$'s may be bonded to each other to form a ring together with a sulfur atom in the formula, and may further include a hetero atom such as an oxygen atom, a sulfur atom, and a nitrogen atom, in addition to the sulfur atom in the formula, as an atom constituting the ring. These groups may have a substituent.

l represents an integer of 0 to 2.

r represents an integer of 0 to 8.

$Z^-$ represents a non-nucleophilic anion.

General Formula (ZI-4) will be described in more detail.

In General Formula (ZI-4), the alkyl group of $R_{13}$, $R_{14}$, and $R_{15}$ is linear or branched, and is preferably an alkyl group having 1 to 10 carbon atoms.

Examples of the cycloalkyl group of $R_{13}$, $R_{14}$, and $R_{15}$ include monocyclic or polycyclic cycloalkyl groups.

The alkoxy group of $R_{13}$ and $R_{14}$ is linear or branched, and is preferably an alkyl group having 1 to 10 carbon atoms.

The alkoxycarbonyl group of $R_{13}$ and $R_{14}$ is linear or branched, and is preferably an alkoxycarbonyl group having 2 to 11 carbon atoms.

Examples of group having the cycloalkyl group of $R_{13}$ and $R_{14}$ include groups having a monocyclic or polycyclic cycloalkyl group. These groups may further have a substituent.

Examples of the alkyl group of the alkylcarbonyl group of $R_{14}$ include the same those as the specific examples of the alkyl group as $R_{13}$ to $R_{15}$ above.

The alkylsulfonyl group and the cycloalkylsulfonyl group of $R_{14}$ are linear, branched, or cyclic, and preferably have 1 to 10 carbon atoms.

Examples of a substituent which each of the groups may have may include a halogen atom (for example, a fluorine atom), a hydroxyl group, a carboxyl group, a cyano group, a nitro group, an alkoxy group, an alkoxyalkyl group, an alkoxycarbonyl group, and an alkoxycarbonyloxy group.

Examples of the ring structure which may formed by the mutual bonding of two $R_{15}$'s include a 5- or 6-membered ring formed by two $R_{15}$'s together with a sulfur atom in General Formula (ZI-4), and particularly preferably a 5-membered ring (that is, a tetrahydrothiophene ring or a 2,5-dihydrothiophene ring) and may be fused with an aryl group or a cycloalkyl group. The two $R_{15}$'s may have a substituent, and examples of the substituent may include a hydroxyl group, a carboxyl group, a cyano group, a nitro group, an alkyl group, a cycloalkyl group, an alkoxy group, an alkoxyalkyl group, an alkoxycarbonyl group, and an alkoxycarbonyloxy group. Substituents may be present in plural numbers for the ring structure, and may be bonded to each other to form a ring.

In General Formula (ZI-4), $R_{15}$ is preferably a methyl group, an ethyl group, a naphthyl group or a divalent group capable of forming a tetrahydrothiophene ring structure together with the sulfur atom by the mutual bonding of two $R_{15}$'s, and is particularly preferably a divalent group capable of forming a tetrahydrothiophene ring structure together with the sulfur atom by the mutual bonding of two $R_{15}$'s.

The substituent which $R_{13}$ and $R_{14}$ can have is preferably a hydroxyl group, an alkoxy group, an alkoxycarbonyl group or a halogen atom (particularly a fluorine atom).

l is preferably 0 or 1, and more preferably 1.

r is preferably 0 to 2.

Examples of $Z^-$ include those enumerated as $Z_1^-$ in General Formula (1) as described above. In one aspect of the present invention, 7 is more preferably the same one as the anion structure ($Z_1^-$) in the acid generator (B1), and even more preferably the non-nucleophilic anion represented by General Formula (2) as described above.

Specific examples of the cation structure which the compound represented by General Formula (ZI-3) or (ZI-4) as described above has include the cation structures in the chemical structures and the like exemplified in paragraphs 0046, 0047, 0072 to 0077, and 0107 to 0110 of JP2011-53360A, and the cation structures in the chemical structures and the like exemplified in paragraphs 0135 to 0137, 0151, and 0196 to 0199 of JP2011-53430A, in addition to the cation structures of the compounds and the like exemplified in JP2004-233661A, JP2003-35948A, US2003/0224288A1, and US2003/0077540A1 as described above.

The photoacid generator as described above can be synthesized by known methods, and can be synthesized in accordance with the method described in, for example, JP2007-161707A.

The photoacid generator (B1) can be used alone or in combination of two or more kinds thereof, and the photoacid generator (B2) can be used alone or in combination of two or more kinds thereof.

Incidentally, other known compounds may be contained, in addition to the compounds as described above, as the photoacid generator (B).

In the present invention, the blend ratio of the photoacid generator (B1) to the photoacid generator (B2) can be appropriately set.

The content of the photoacid generator (B) (a total sum of contents in the case where the photoacid generators (B) are present in plural kinds) in the composition is preferably 0.1% to 30% by mass, more preferably 1% to 25% by mass, still more preferably 5% to 20% by mass, and particularly preferably 10% to 20% by mass, with respect to the total solid content of the composition.

Specific examples of the photoacid generator are shown below, but the present invention is not limited thereto.

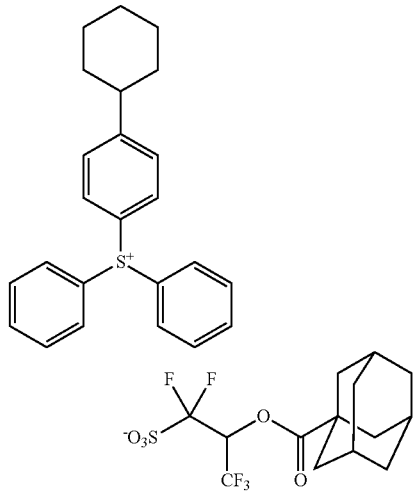

B1-1

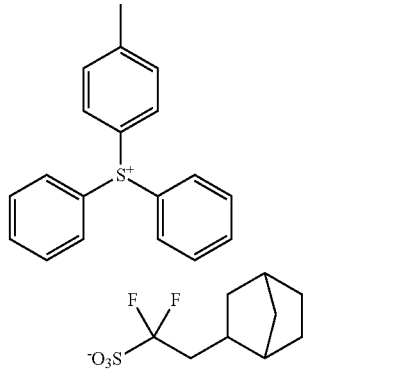

B1-2

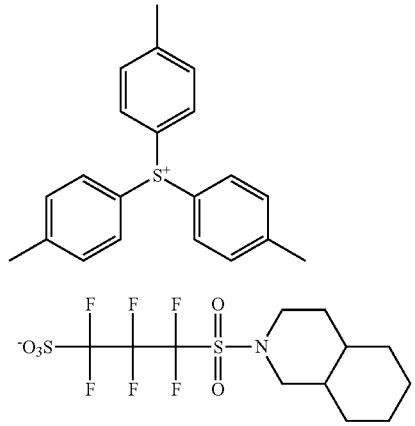

B1-3

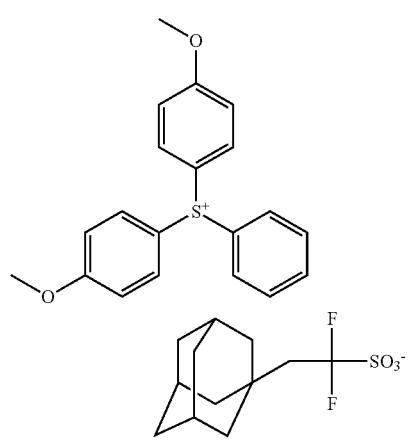
B1-4
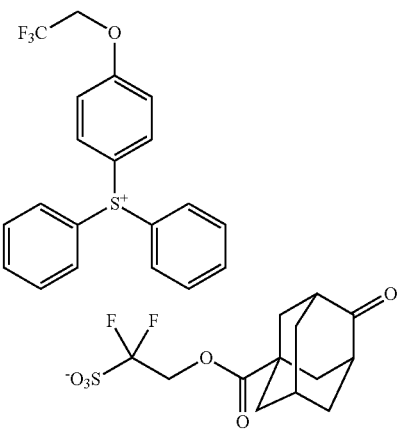
B1-7
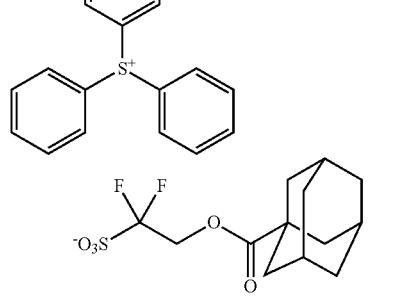
B1-5
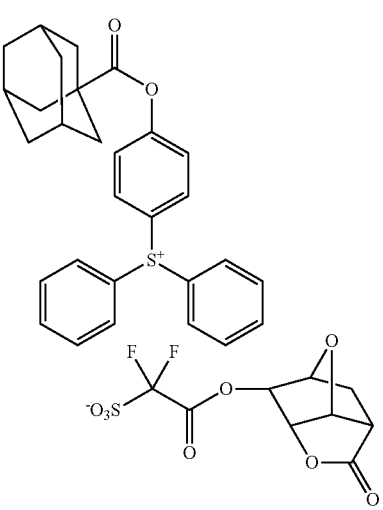
B1-8
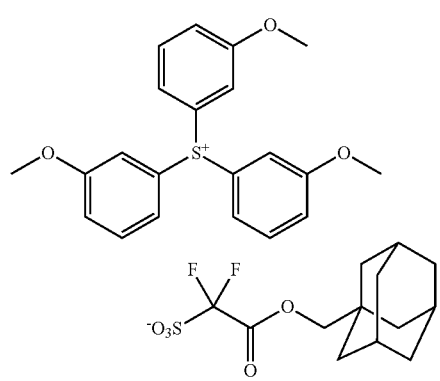
B1-6
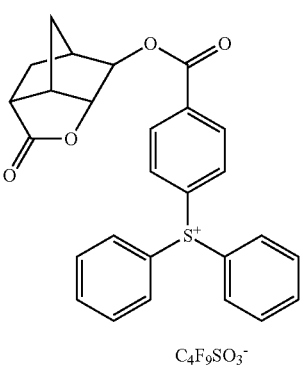
B1-9
$C_4F_9SO_3^-$ B1-10
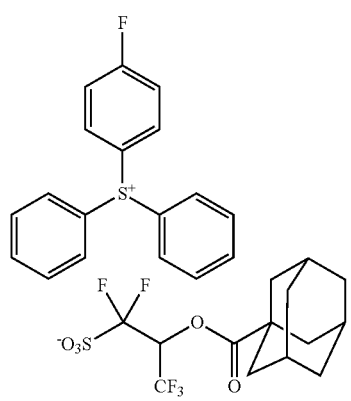
B1-11
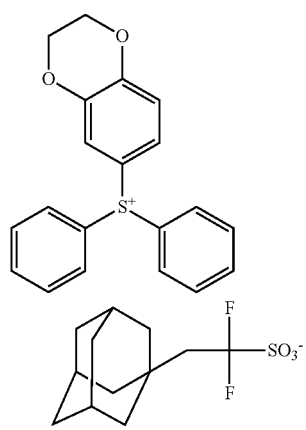
B1-12
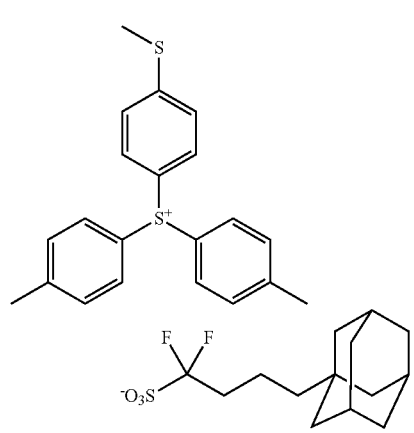
B2-1
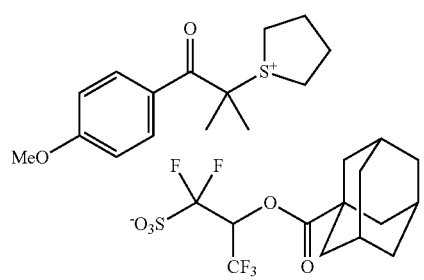
B2-2
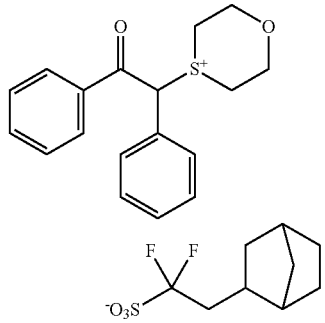
B2-3
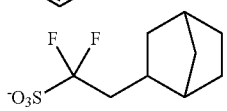
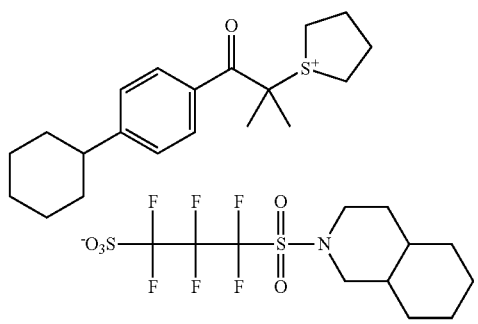
B2-4
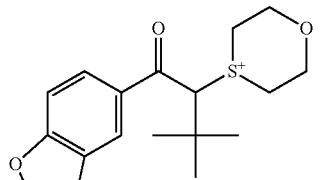
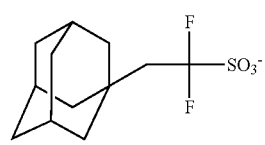
B2-5
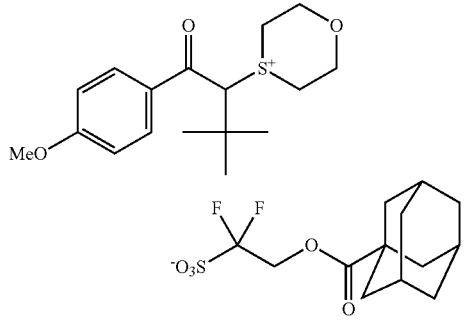

B2-6
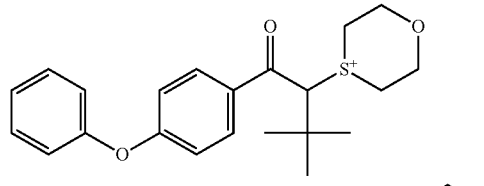
B2-7
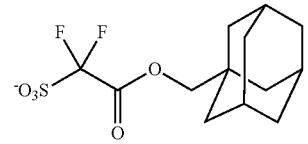
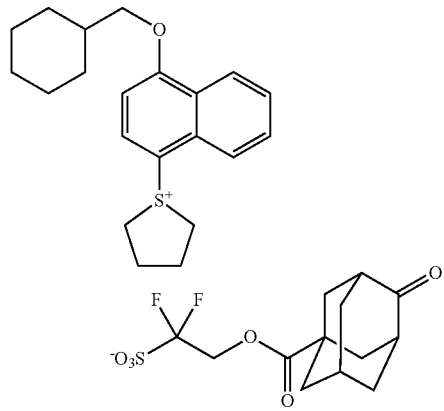
B2-8
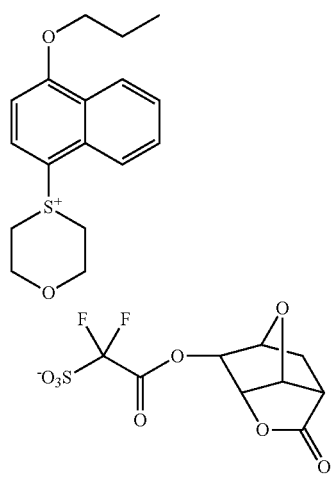
B2-9
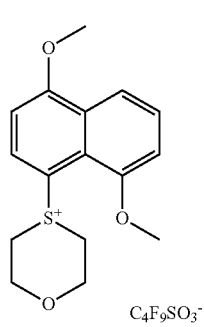
C4F9SO3-
B2-10
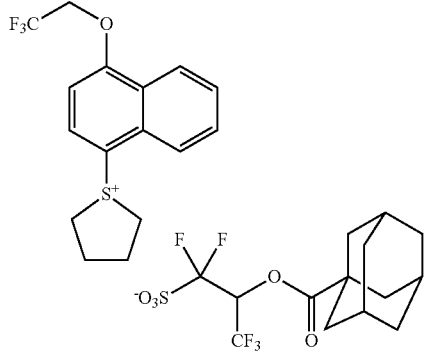
B2-11
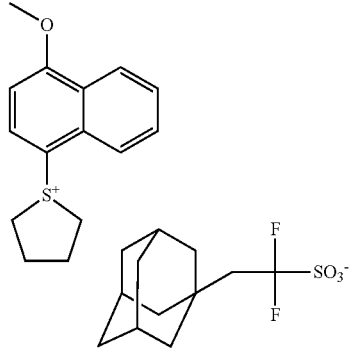
B2-12
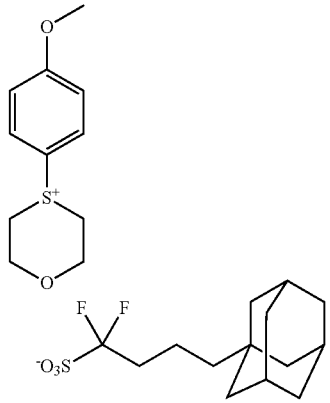
PAG-1
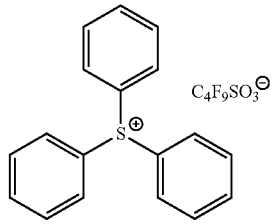
PAG-2
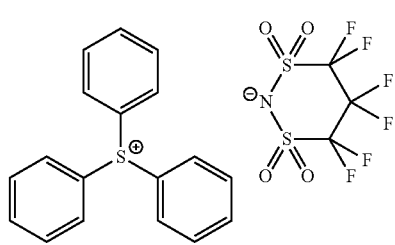

PAG-3
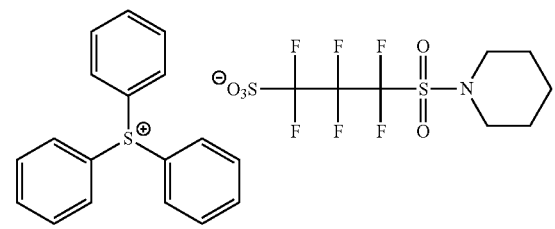
PAG-4
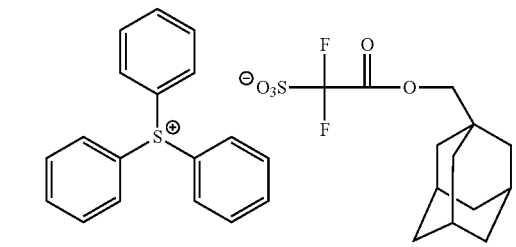
PAG-5
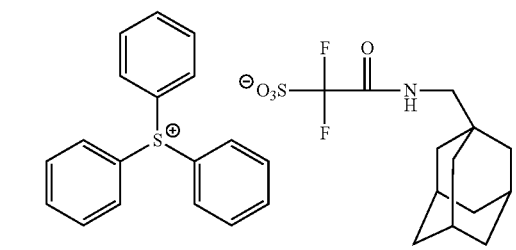
PAG-6
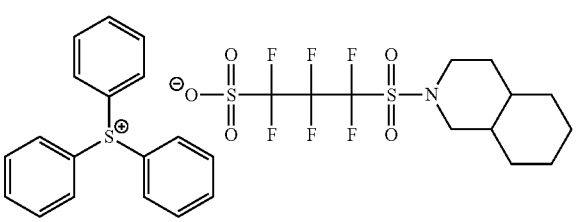
PAG-7
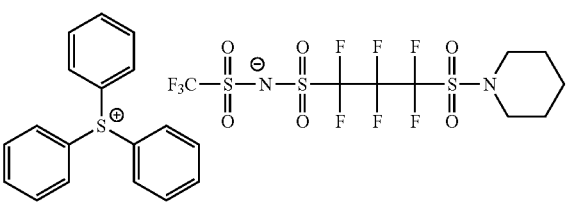
PAG-8
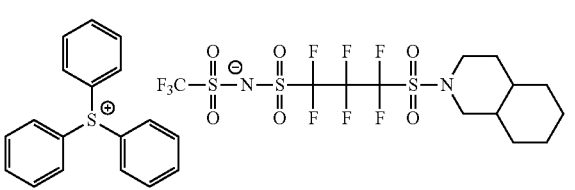
PAG-9
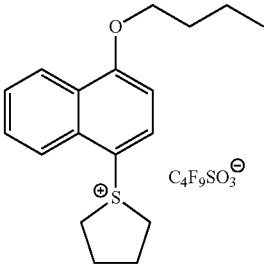
PAG-10
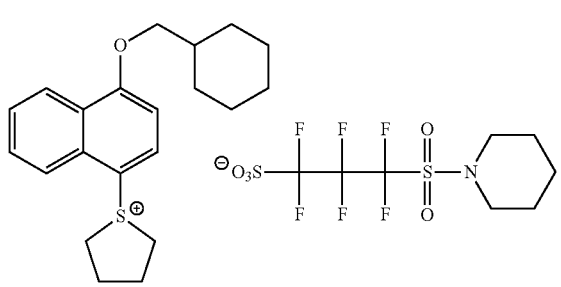
PAG-11
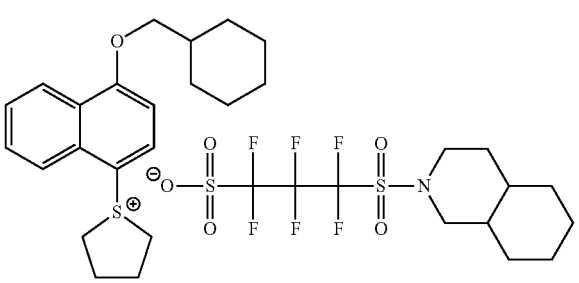
PAG-13
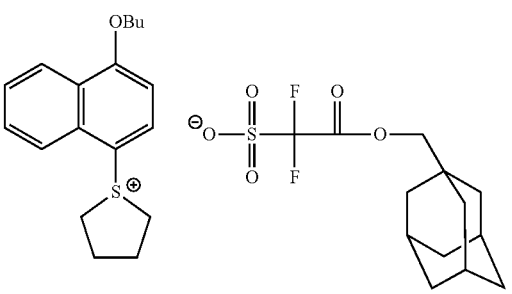
PAG-14
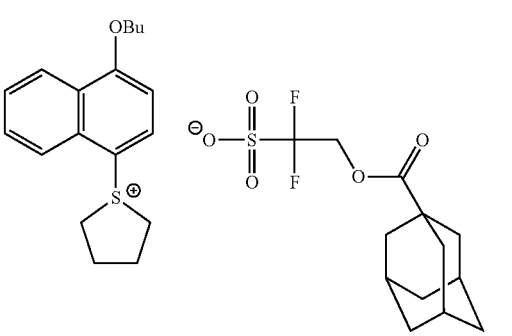

-continued

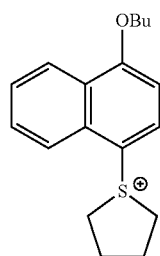
PAG-15

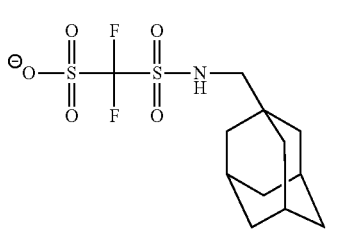
PAG-16

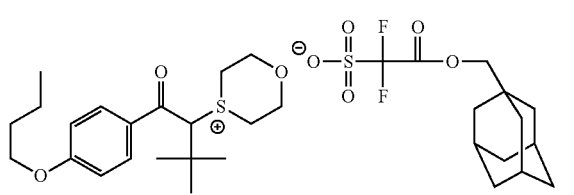
PAG-17

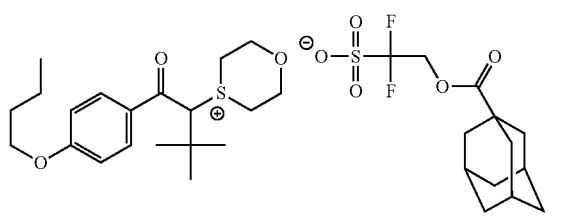
PAG-18

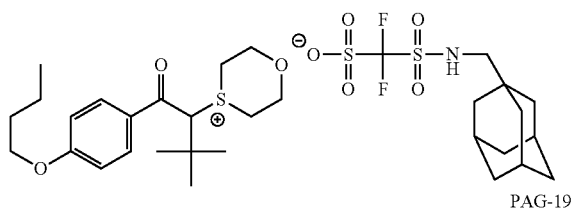
PAG-19

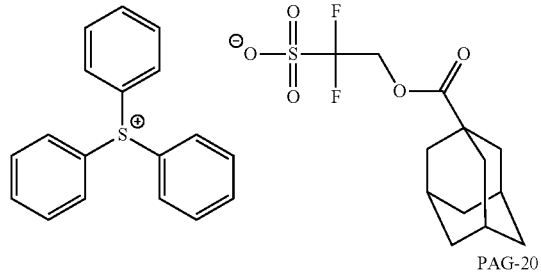
PAG-20

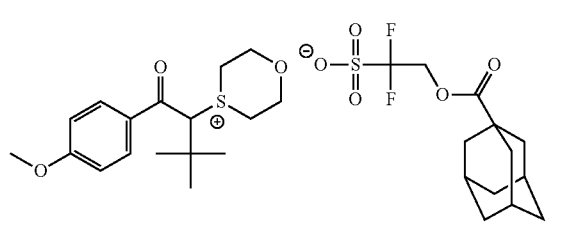

<Resin (A)>

The resin (A) contained in the composition of the present invention is preferably a resin which is typically capable of decomposing by the action of an acid to increase the polarity, and has an increased solubility in an alkali developer by the action of an acid, and a decreased solubility in a developer having an organic solvent as a main component by the action of an acid. The resin (A) preferably has a group (hereinafter also referred to as an "acid-decomposable group") capable of decomposing by the action of an acid to generate an alkali-soluble group at either the main chain or side chain of the resin, or at both the main chain and the side chain.

The resin (A) is preferably insoluble or sparingly soluble in an alkali developer.

The acid-decomposable group preferably has a structure which is protected with a group capable of decomposing by the action of an acid to leave an alkali-soluble group.

Examples of the alkali-soluble group include a phenolic hydroxyl group, a carboxylic acid group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group.

Preferred examples of the alkali-soluble group include a carboxyl group, a fluorinated alcohol group (preferably a hexafluoroisopropanol group), and a sulfonic acid group.

A preferred acid-decomposable group is a group obtained by substituting a hydrogen atom of these groups with a group capable of leaving by the action of an acid.

Examples of the group capable of leaving by the action of an acid include $—C(R_{36})(R_{37})(R_{38})$, $—C(R_{36})(R_{37})(OR_{39})$, and $—C(R_{01})(R_{02})(OR_{39})$.

In General Formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, an aralkyl group, or an alkenyl group.

As the acid-decomposable group, a cumyl ester group, an enol ester group, an acetal ester group, a tertiary alkyl ester group, and the like are preferable, and a tertiary alkyl ester group is more preferable.

As a repeating unit having the acid-decomposable group, which can be contained in the resin (A), a repeating unit represented by the following General Formula (AI) is preferable.

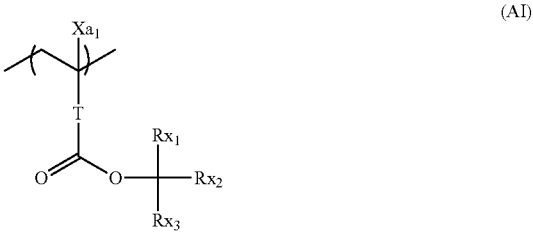

(AI)

In General Formula (AI), $Xa_1$ represents a hydrogen atom or an alkyl group which may have a substituent.

T represents a single bond or a divalent linking group.

$Rx_1$ to $Rx_3$ each independently represent an (linear or branched) alkyl group or a (monocyclic or polycyclic) cycloalkyl group.

Two members out of $Rx_1$ to $Rx_3$ may be bonded to each other to form a (monocyclic or polycyclic) cycloalkyl group.

Examples of the alkyl group which may have a substituent, represented by $Xa_1$, include a methyl group and a group represented by —$CH_2$—$R_{11}$. $R_{11}$ represents a halogen atom (a fluorine atom or the like), a hydroxyl group, or a monovalent organic group, and examples thereof include an alkyl group having 5 or less carbon atoms, and an acyl group having 5 or less carbon atoms, preferably an alkyl group having 3 or less carbon atoms, and more preferably a methyl group. In one aspect, $Xa_1$ is preferably a hydrogen atom, a methyl group, a trifluoromethyl group, a hydroxymethyl group, or the like.

Examples of the divalent linking group of T include an alkylene group, a —COO-Rt- group, and an —O-Rt- group. In the formulae, Rt represents an alkylene group or a cycloalkylene group.

T is preferably a single bond or a —COO-Rt- group. Rt is preferably an alkylene group having 1 to 5 carbon atoms, and more preferably a —$CH_2$— group, a —$(CH_2)_2$— group, or a —$(CH_2)_3$— group.

As the alkyl group of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group is preferable.

As the cycloalkyl group of $Rx_1$ to $Rx_3$, a monocyclic cycloalkyl such as a cyclopentyl group and a cyclohexyl group, and a polycyclic cycloalkyl group such as a norbornyl group, a tetracyclodecanyl group, a tetracyclododecanyl group, and an adamantyl group are preferable.

As the cycloalkyl group formed by the mutual bonding of two members of $Rx_1$ to $Rx_3$, a monocyclic cycloalkyl group such as a cyclopentyl group and a cyclohexyl group, and a polycyclic cycloalkyl group such as a norbornyl group, a tetracyclodecanyl group, a tetracyclododecanyl group, and an adamantyl group are preferable, and a monocyclic cycloalkyl group having 5 or 6 carbon atoms is particularly preferable.

In the cycloalkyl group formed by the mutual bonding of two members of $Rx_1$ to $Rx_3$, for example, one of the methylene groups constituting the ring may be substituted with a hetero atom such as an oxygen atom, or with a group having a hetero atom, such as a carbonyl group.

An aspect of the repeating unit represented by General Formula (AI), for example, in which $Rx_1$ is a methyl group or an ethyl group, and $Rx_2$ and $Rx_3$ are bonded to form the afore-mentioned cycloalkyl group, is preferable.

Each of the groups may have a substituent, and examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms), with those having 8 or less carbon atoms being preferable.

The total content of all the repeating units having acid-decomposable groups is preferably 20% to 90% by mole, more preferably 25% to 85% by mole, and still more preferably 30% to 80% by mole, with respect to all the repeating units in the resin (A).

Specific preferred examples of the preferred repeating unit having an acid-decomposable group are shown below, but the present invention is not limited thereto.

In the specific examples, Rx and $Xa_1$ each represent a hydrogen atom, $CH_3$, $CF_3$, or $CH_2OH$. Rxa and Rxb each represent an alkyl group having 1 to 4 carbon atoms. Z represents a substituent including a polar group, and in the case where Z's are present in plural numbers, they may be the same as or different from each other. p represents 0 or a positive integer. Examples of the substituent including a polar group, represented by Z, include a hydroxyl group, a cyano group, an amino group, a linear or branched alkyl group having an alkylamide group or a sulfonamide group, and a cycloalkyl group, with an alkyl group having a hydroxyl group being preferable. As the branched alkyl group, an isopropyl group is particularly preferable.

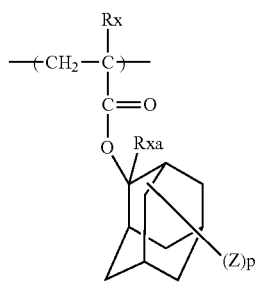

1

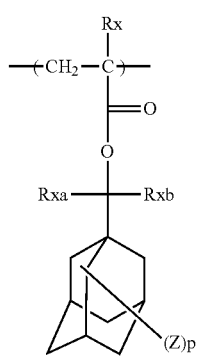

2

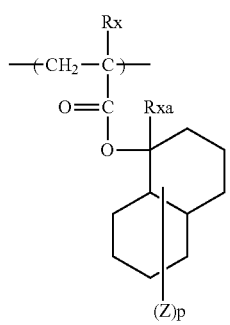

3

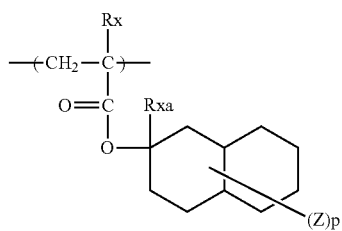

4

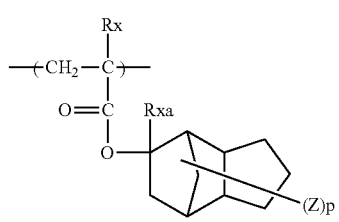

5

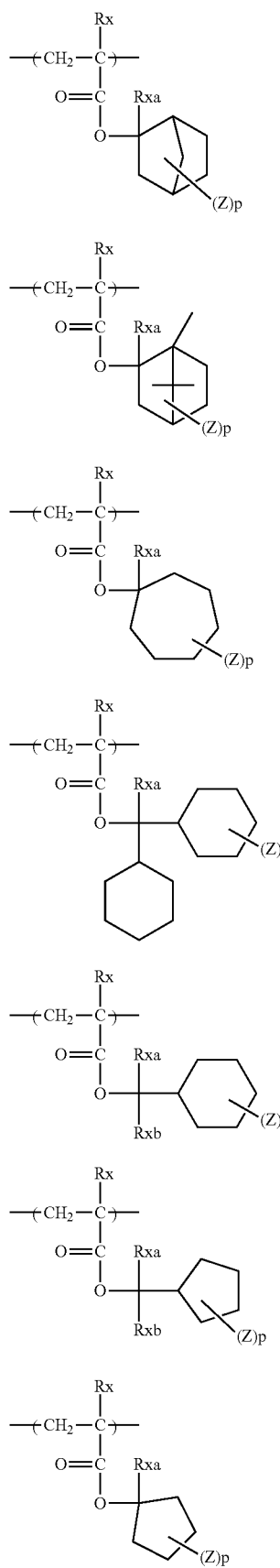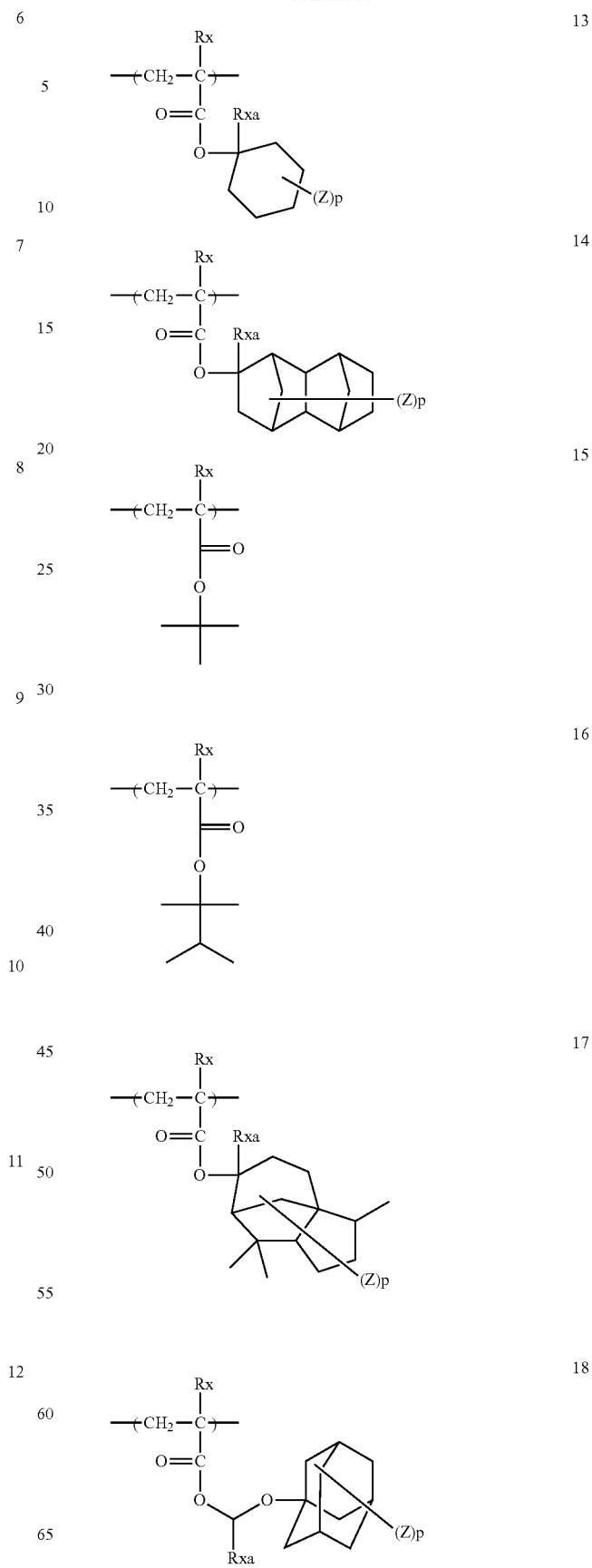

19 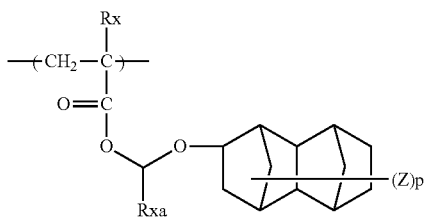

20 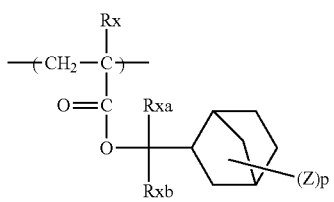

21 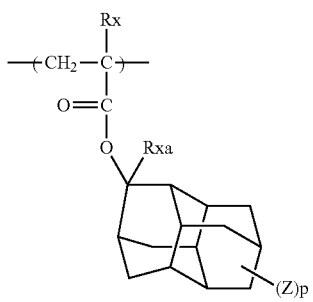

22 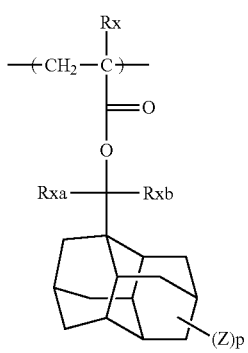

23 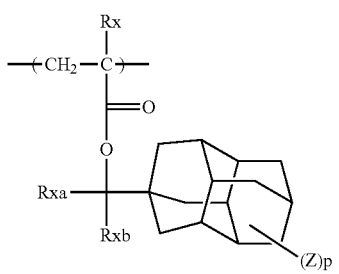

24 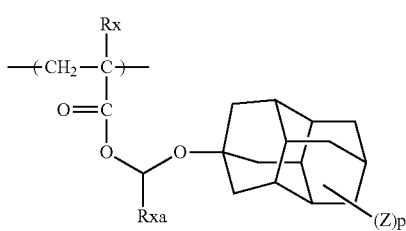

25 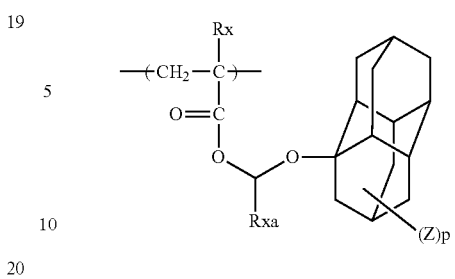

It is preferable that the resin (A) contains, for example, a repeating unit represented by General Formula (3) as the repeating unit represented by General Formula (AI).

(3)

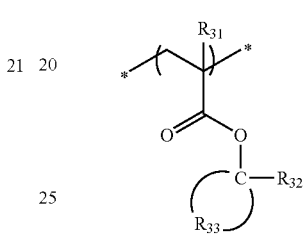

In General Formula (3), $R_{31}$ represents a hydrogen atom or an alkyl group.

$R_{32}$ represents an alkyl group or a cycloalkyl group, and specific examples thereof include a methyl group, an ethyl group, an n-propyl group, an isopropyl group, an n-butyl group, an isobutyl group, a sec-butyl group, a tert-butyl group, and a cyclohexyl group.

$R_{33}$ represents an atomic group required for forming a monocyclic alicyclic hydrocarbon structure together with carbon atoms to which $R_{32}$ is bonded. In the alicyclic hydrocarbon structure, a part of carbon atoms constituting a group may be substituted with a hetero atom, or a group having a hetero atom.

The alkyl group of $R_{31}$ may have a substituent and examples of the substituent include a fluorine atom and a hydroxyl group. $R_{31}$ preferably represents a hydrogen atom, a methyl group, a trifluoromethyl group, or a hydroxymethyl group.

$R_{32}$ is preferably a methyl group, an ethyl group, an n-propyl group, an isopropyl group, a tert-butyl group, or a cyclohexyl group, and more preferably a methyl group, an ethyl group, an isopropyl group, or a tert-butyl group.

The monocyclic alicyclic hydrocarbon structure formed by $R_{33}$ together with carbon atoms is preferably a 3- to 8-membered ring, and more preferably a 5- or 6-membered ring.

In the monocyclic alicyclic hydrocarbon structure formed by $R_{33}$ together with carbon atoms, examples of the hetero atom which can constitute a ring include an oxygen atom and a sulfur atom, and examples of the group having a hetero atom include a carbonyl group. However, it is preferable that the group having a hetero atom is not an ester group (ester bond).

The monocyclic alicyclic hydrocarbon structure formed by $R_{33}$ together with carbon atoms is preferably formed with only carbon atoms and hydrogen atoms.

The repeating unit represented by General Formula (3) is preferably a repeating unit represented by the following General Formula (3').

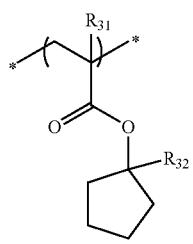
(3')
In General Formula (3'), $R_{31}$ and $R_{32}$ have the same definitions as those in General Formula (3), respectively.
Specific examples of the repeating unit having the structure represented by General Formula (3) are shown below, but are not limited thereto.
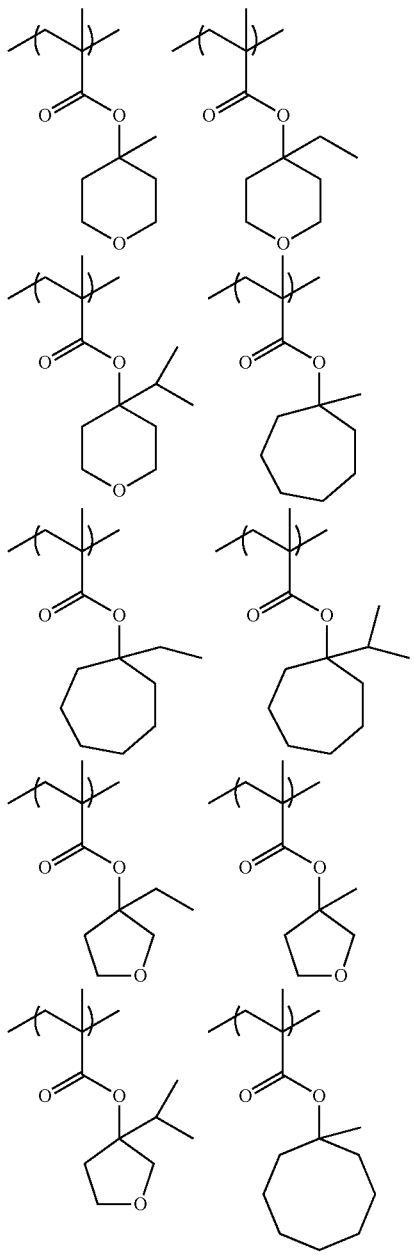
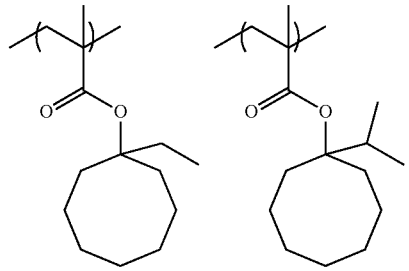
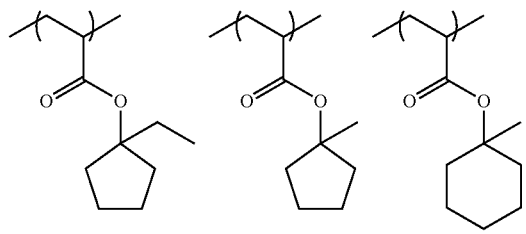
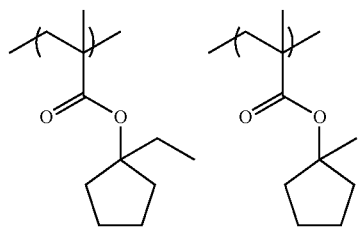
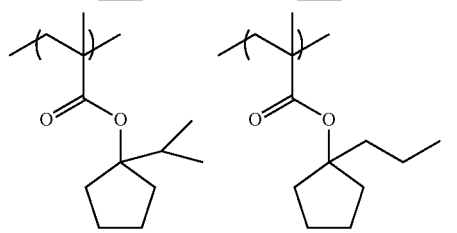
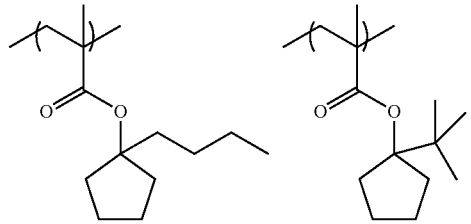
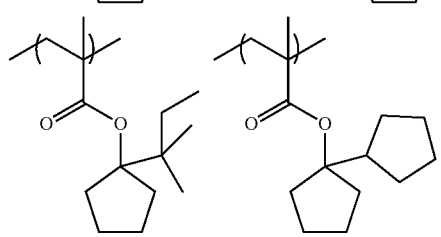
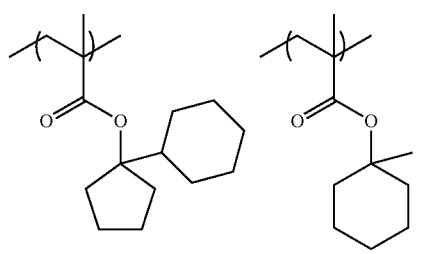

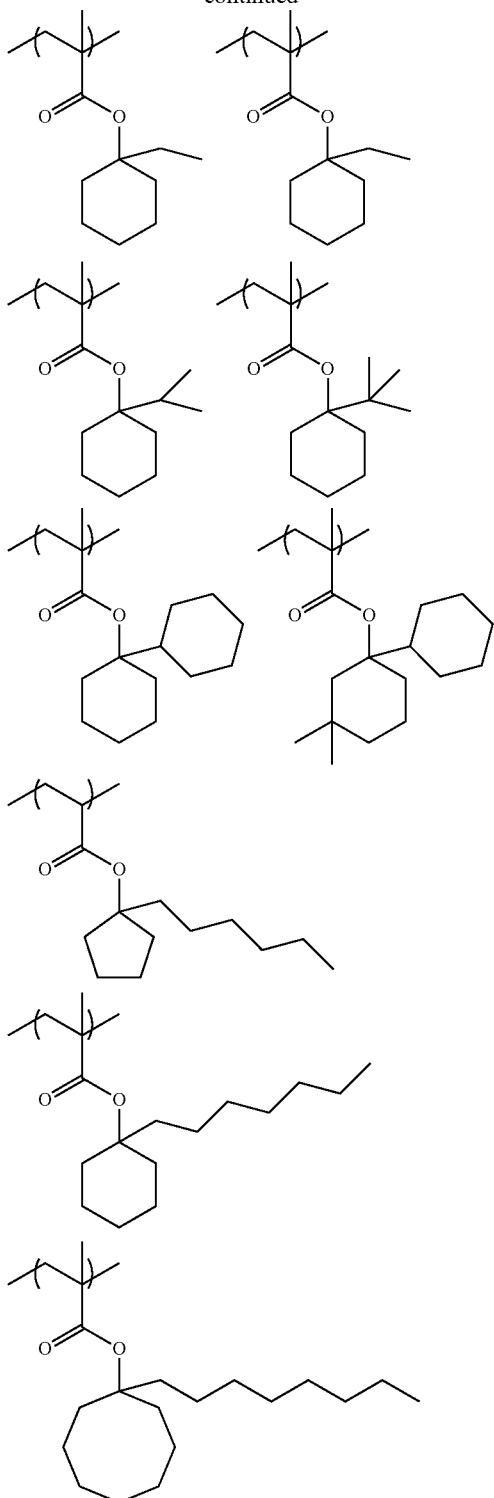

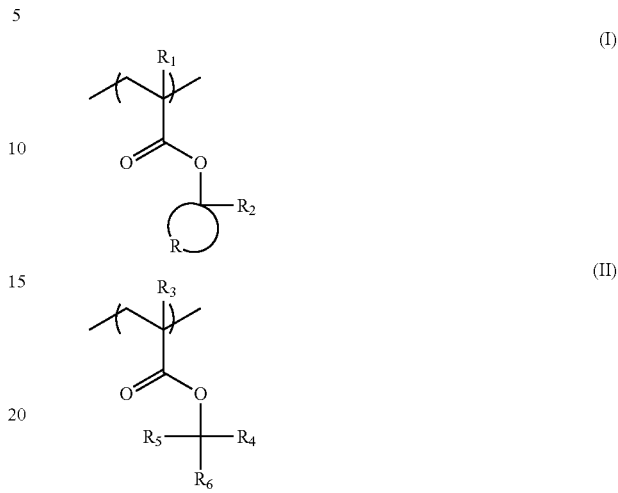

The content of the repeating unit having a structure represented by General Formula (3) is preferably 20% to 80% by mole, more preferably 25% to 75% by mole, and still more preferably 30% to 70% by mole, with respect to all the repeating units of the resin (A).

The resin (A) is more preferably resin which has at least one of the repeating unit represented by General Formula (I) or the repeating unit represented by General Formula (II), for example, as the repeating unit represented by General Formula (AI).

In Formulae (I) and (II), $R_1$ and $R_3$ each independently represent a hydrogen atom, a methyl group which may have a substituent, or a group represented by —$CH_2$—$R_{11}$. $R_{11}$ represents a monovalent organic group.

$R_2$, $R_4$, $R_5$, and $R_6$ each independently represent an alkyl group or a cycloalkyl group.

R represents an atomic group required for forming an alicyclic structure together with a carbon atom to which $R_2$ is bonded.

$R_1$ and $R_3$ preferably represent a hydrogen atom, a methyl group, a trifluoromethyl group, or a hydroxymethyl group. Specific and preferred examples of the monovalent organic group in $R_{11}$ include the same ones as described for $R_{11}$ in General Formula (AI).

The alkyl group in $R_2$ may be linear or branched, and may have a substituent.

The cycloalkyl group in $R_2$ monocyclic or polycyclic, and may have a substituent.

$R_2$ is preferably an alkyl group, more preferably an alkyl group having 1 to 10 carbon atoms, and still more preferably an alkyl group having 1 to 5 carbon atoms, and examples thereof include a methyl group, an ethyl group, an n-propyl group, an i-propyl group, and a t-butyl group. As the alkyl group in $R_2$, a methyl group, an ethyl group, an i-propyl group, and a t-butyl group are preferable.

R represents an atomic group required to form an alicyclic structure together with a carbon atom. The alicyclic structure formed by R together with the carbon atom is preferably a monocyclic alicyclic structure. R preferably has 3 to 7 carbon atoms, and more preferably 5 or 6 carbon atoms.

$R_3$ is preferably a hydrogen atom or a methyl group, and more preferably a methyl group.

The alkyl group in $R_4$, $R_5$, or $R_6$ may be linear or branched, and may have a substituent. Examples of the alkyl group include alkyl groups having 1 to 4 carbon atoms, such as a methyl group, an ethyl group, an n-propyl group, an isopropyl group, an n-butyl group, an isobutyl group, and a t-butyl group.

The cycloalkyl group in $R_4$, $R_5$, or $R_6$ may be monocyclic or polycyclic, and may have a substituent. Preferred examples of the cycloalkyl group include monocyclic cycloalkyl groups such as a cyclopentyl group and a cyclohexyl group, and polycyclic cycloalkyl group such as a norbornyl group, a tetracyclodecanyl group, a tetracyclodo-decanyl group, and an adamantyl group.

Examples of the substituent which each of the groups may have include the same groups as those described as the substituent which each of the groups in General Formula (AI) may have.

In General Formula (II), $R_4$, $R_5$, and $R_6$ are preferably an alkyl group, and the sum of the numbers of carbon atoms of $R_4$, $R_5$, and $R_6$ is preferably 5 or more, preferably 6 or more, and still more preferably 7 or more.

The resin (A) is more preferably a resin which contains the repeating unit represented by General Formula (I) and the repeating unit represented by General Formula (II), as the repeating unit represented by General Formula (AI).

Moreover, in another aspect, a resin which contains at least two kinds of the repeating unit represented by General Formula (I) as the repeating unit represented by General Formula (AI) is more preferable. In the case where the resin contains at least two kinds of the repeating unit represented by General Formula (I), it is preferable that the resin contains both of a repeating unit in which an alicyclic structure formed by R together with a carbon atom is a monocyclic alicyclic structure and a repeating unit in which an alicyclic structure formed by R together with a carbon atom is a polycyclic alicyclic structure. The monocyclic alicyclic structure preferably has 5 to 8 carbon atoms, more preferably 5 or 6 carbon atoms, and particularly preferably 5 carbon atoms. As the polycyclic alicyclic structure, a norbornyl group, a tetracyclodecanyl group, a tetracyclodo-decanyl group, and an adamantyl group are preferable.

The repeating unit having an acid-decomposable group which the resin (A) contains may be used alone or in combination of two or more kinds thereof. In the case where the repeating units are used in combination, the following combinations are preferable. In the following formulae, R's each independently represent a hydrogen atom or a methyl group.

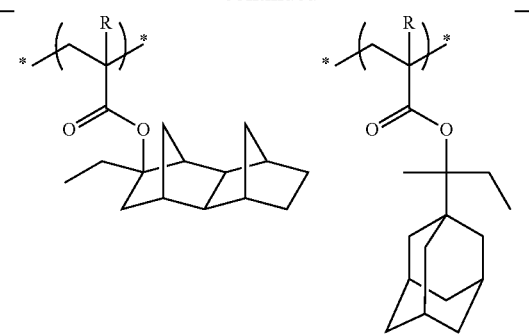

-continued

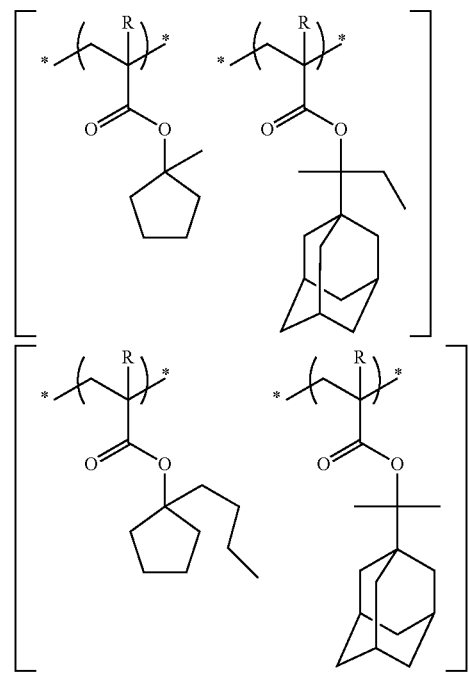

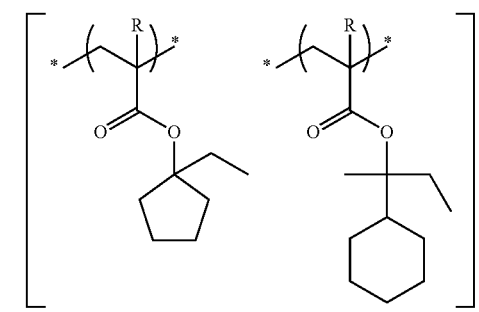

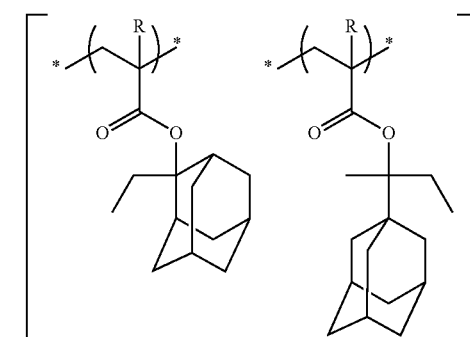

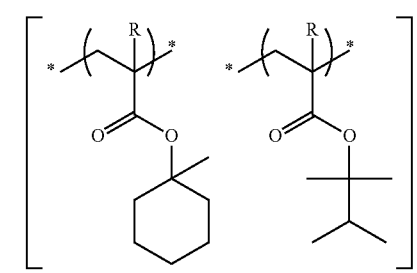

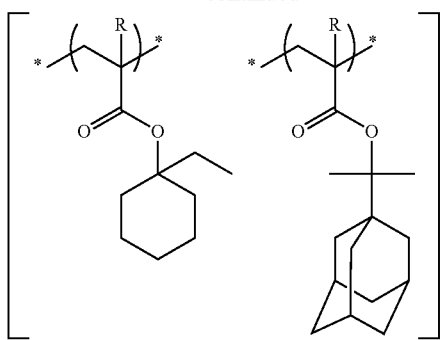
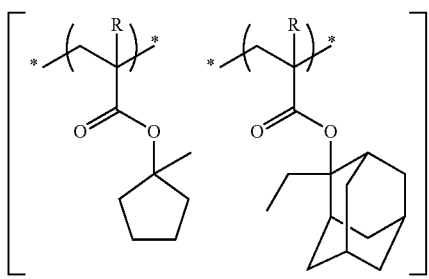
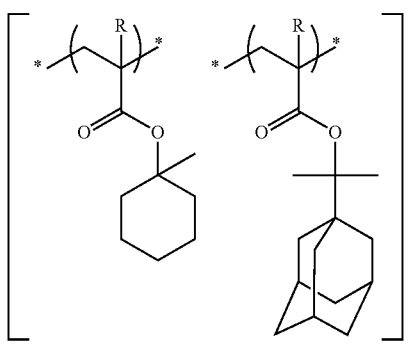
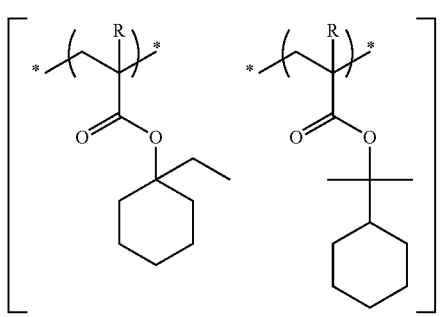
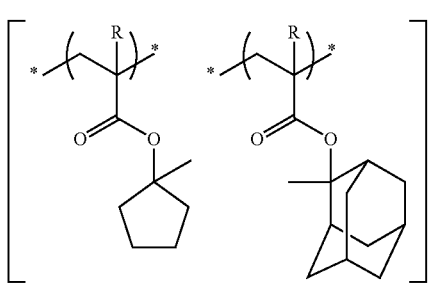
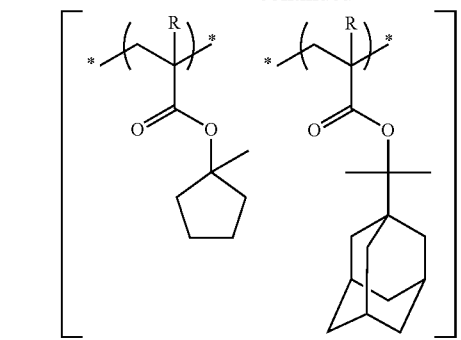
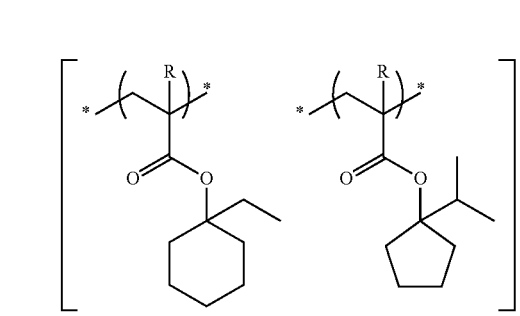
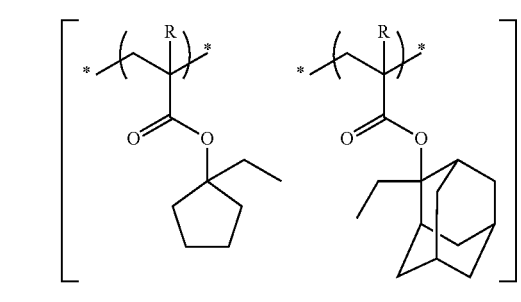
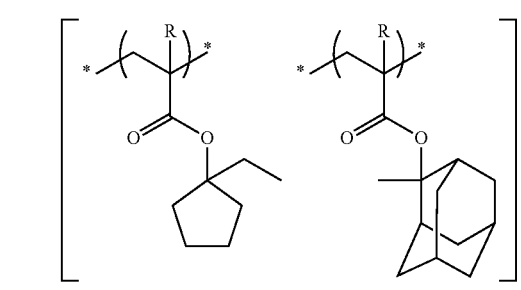
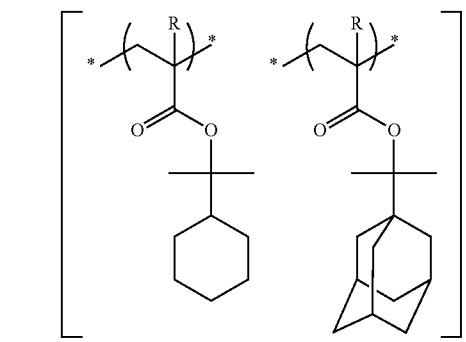

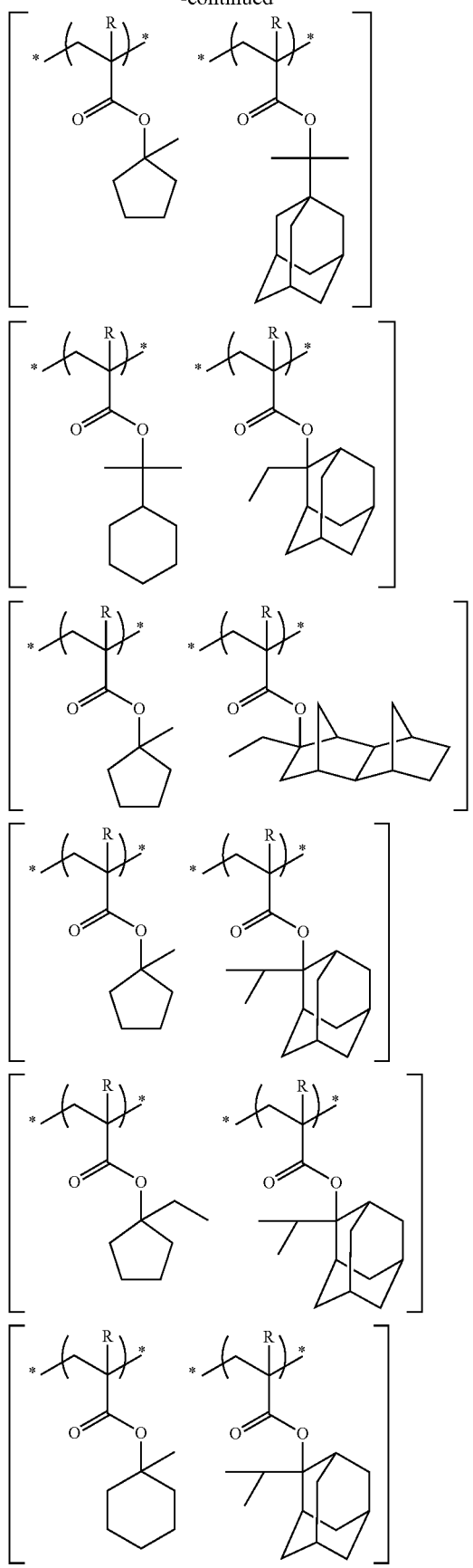

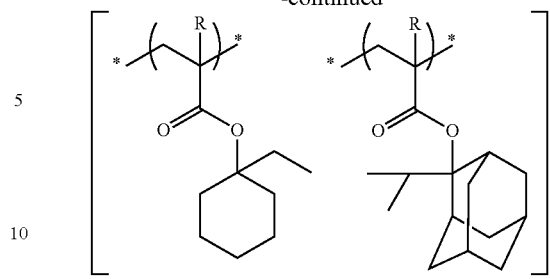

In one aspect, it is preferable that the resin (A) contains a repeating unit having a cyclic carbonic acid ester structure. This cyclic carbonic acid ester structure is a structure having a ring including a bond represented by —O—C(=O)—O— as an atomic group constituting the ring. The ring including a bond represented by —O—C(=O)—O— as an atomic group constituting the ring is preferably a 5- to 7-membered ring, and most preferably a 5-membered ring. Such a ring may be fused with another ring to form a fused ring.

It is preferable that the resin (A) contains a repeating unit having a lactone structure or a sultone (cyclic sulfonic acid ester) structure.

As the lactone group or the sultone group, any group may be used as long as it has a lactone structure or a sultone structure, but the structure is preferably a 5- to 7-membered ring lactone structure or sultone structure, and more preferably a 5- to 7-membered ring lactone structure or sultone structure to which another ring structure is fused in the form of forming a bicyclo structure or a spiro structure. The resin (A) still more preferably has a repeating unit having a lactone structure or a sultone structure represented by any one of the following General Formulae (LC1-1) to (LC1-17), (SL1-1), and (SL1-2). Further, the lactone structure or the sultone structure may be bonded directly to the main chain. The lactone structures or the sultone structures are preferably (LC1-1), (LC1-4), (LC1-5), and (LC1-8), and more preferably (LC1-4). By using such a specific lactone structure or sultone structure, LWR and development defects are relieved.

LC1-1

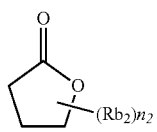

LC1-2

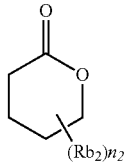

LC1-3

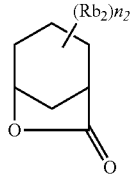

LC1-4 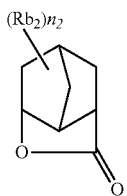

LC1-5 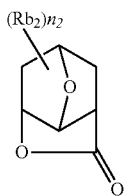

LC1-6 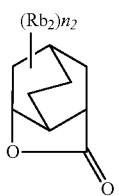

LC1-7 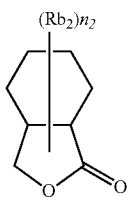

LC1-8 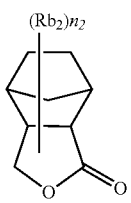

LC1-9 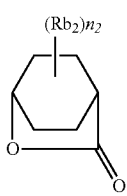

LC1-10 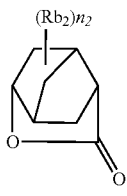

LC1-11 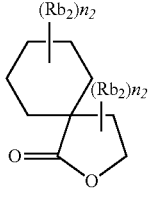

LC1-12 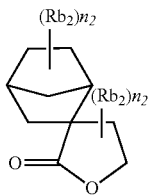

LC1-13 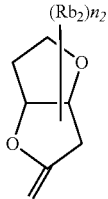

LC1-14 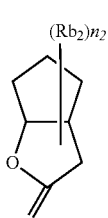

LC1-15 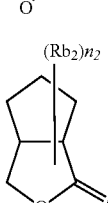

LC1-16 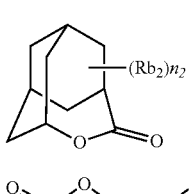

LC1-17 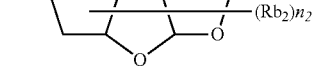

SL1-1 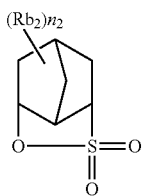

SL1-2 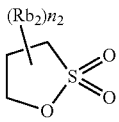

The lactone structure moiety or the sultone structure moiety may or may not have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, and an acid-decomposable group. Among these, an alkyl group having 1 to 4 carbon atoms, a cyano group, and an acid-decomposable group are more preferable. $n_2$ represents an integer of 0 to 4. When $n_2$ is 2 or more, the substituents ($Rb_2$) which are present in plural numbers may be the same as or different from each other, and further, the substituents ($Rb_2$) which are present in plural numbers may be bonded to each other to form a ring.

It is preferable that the resin (A) contains a repeating unit having a lactone structure or a sultone structure, represented by the following General Formula (III).

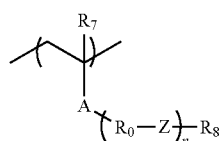
(III)

In Formula (III),

A represents an ester bond (a group represented by —COO—) or an amide bond (a group represented by —CONH—).

In the case where $R_0$'s are present in plural numbers, they each independently represent an alkylene group, a cycloalkylene group, or a combination thereof.

In the case where Z's are present in plural numbers, they each independently represent a single bond, an ether bond, an ester bond, an amide bond, a urethane bond, a group represented by:

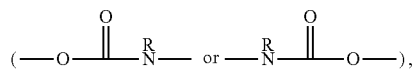

an urea bond, or a group represented by:

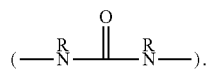

Here, R's each independently represent a hydrogen atom, an alkyl group, a cycloalkyl group, or an aryl group.

$R_8$ represents a monovalent organic group having a lactone structure or a sultone structure.

n is the repetition number of the structure represented by —$R_0$—Z—, and represents an integer of 0 to 2.

$R_7$ represents a hydrogen atom, a halogen atom, or an alkyl group.

The alkylene group and the cycloalkylene group of $R_0$ may have a substituent.

Z is preferably an ether bond or an ester bond, and particularly preferably an ester bond.

The alkyl group of $R_7$ is preferably an alkyl group having 1 to 4 carbon atoms, more preferably a methyl group or an ethyl group, and particularly preferably a methyl group. The alkylene group and the cycloalkylene group of $R_0$, and the alkyl group in $R_7$ may be each substituted, and examples of the substituent include a halogen atom such as a fluorine atom, a chlorine atom, and a bromine atom, an alkoxy group such as a mercapto group, a hydroxy group, a methoxy group, an ethoxy group, an isopropoxy group, a t-butoxy group, and a benzyloxy group, and an acetoxy group such as an acetyloxy group and a propionyloxy group. $R_7$ is preferably a hydrogen atom, a methyl group, a trifluoromethyl group, or a hydroxymethyl group.

The preferred chained alkylene group in $R_0$ is a chained alkylene group, preferably having 1 to 10 carbon atoms, and more preferably having 1 to 5 carbon atoms, and examples thereof include a methylene group, an ethylene group, and a propylene group. Preferred examples of the cycloalkylene group include a cycloalkylene group having 3 to 20 carbon atoms, and examples thereof include a cyclohexylene group, a cyclopentylene group, a norbornylene group, and an adamantylene group. In order to express the effects of the present invention, a chained alkylene group is more preferable, and a methylene group is particularly preferable.

The monovalent organic group having a lactone structure or sultone structure represented by $R_8$ is not limited as long as it has the lactone structure or sultone structure, specific examples thereof include the above-mentioned lactone structures or sultone structures represented by General Formula (LC1-1) to (LC1-17), (SL1-1), and (SL1-2), and among these, the structure represented by (LC1-4) is particularly preferable. Further, $n_2$ in (LC1-1) to (LC1-17), (SL1-1), and (SL1-2) is more preferably 2 or less.

Furthermore, $R_8$ is preferably a monovalent organic group having an unsubstituted lactone structure or sultone structure, or a monovalent organic group having a lactone structure or a sultone structure having a methyl group, a cyano group, or an alkoxycarbonyl group as a substituent, and more preferably a monovalent organic group having a lactone structure having a cyano group as a substituent (cyanolactone) or a sultone structure having a cyano group as a substituent (cyanosultone).

In General Formula (III), n is preferably 0 or 1.

As the repeating unit having a lactone structure or a sultone structure, a repeating unit represented by the following General Formula (III-1) or (III-1') is more preferable.

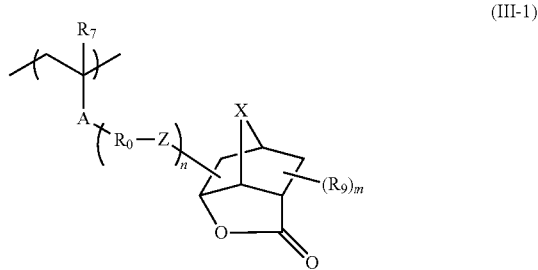
(III-1)

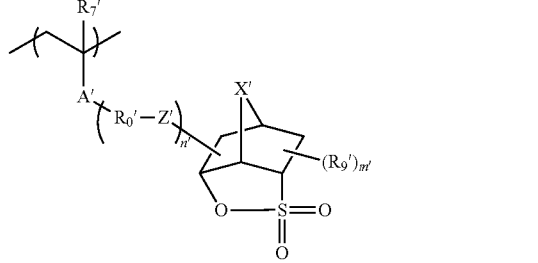
(III-1')

In General Formulae (III-1) and (III-1'), $R_7$, A, $R_0$, Z, and n have the same definitions as in General Formula (III).

$R_7'$, A', $R_0'$, Z', and n' have the same definitions $R_7$, A, $R_0$, Z, and n, respectively, in General Formula (III).

In the case where $R_9$ are in plural numbers, they each independently represent an alkyl group, a cycloalkyl group, an alkoxycarbonyl group, a cyano group, a hydroxyl group, or an alkoxy group, and in the case where they are in plural numbers, two $R_9$'s may be bonded to each other to form a ring.

In the case where $R_9$'s are in plural numbers, they each independently represent an alkyl group, a cycloalkyl group, an alkoxycarbonyl group, a cyano group, a hydroxyl group, or an alkoxy group, and in the case where they are in plural numbers, two $R_9$'s may be bonded to each other to form a ring.

X and X' each independently represent an alkylene group, an oxygen atom, or a sulfur atom.

m and m' are each the number of substituents, and each independently represent an integer of 0 to 5. m and m' are each independently preferably 0 or 1.

As the alkyl group of $R_9$ and $R_9'$, an alkyl group having 1 to 4 carbon atoms is preferable, a methyl group and an ethyl group are more preferable, and a methyl group is most preferable. Examples of the cycloalkyl group include a cyclopropyl group, a cyclobutyl group, a cyclopentyl group, and a cyclohexyl group. Examples of the alkoxycarbonyl group include a methoxycarbonyl group, an ethoxycarbonyl group, an n-butoxycarbonyl group, and a t-butoxycarbonyl group. Examples of the alkoxy group include a methoxy group, an ethoxy group, a propoxy group, an isopropoxy group, and a butoxy group. These groups may have a substituent, and examples of the substituent include an alkoxy group such as a hydroxy group, a methoxy group, and an ethoxy group, a cyano group, and a halogen atom such as a fluorine atom. $R_9$ and $R_9'$ are each more preferably a methyl group, a cyano group, or an alkoxycarbonyl group, and still more preferably a cyano group.

Examples of the alkylene group of X and X' include a methylene group and an ethylene group. X and X' are preferably an oxygen atom or a methylene group, and more preferably a methylene group.

In the case where m and m' are 1 or more, at least one of $R_9$ or $R_9'$ are preferably substituted at the α- or β-position of the carbonyl group of the lactone, and particularly preferably at the α-position.

Specific examples of the group having a lactone structure or the repeating unit having a sultone structure, represented by General Formula (III-1) or (III-1') include the structures described in paragraphs [0150] to [0151] of JP2013-178370A.

In the case where the repeating units are present in plural kinds, the content of the repeating units represented by General Formula (III) is preferably 15% to 60% by mole, more preferably 20% to 60% by mole, and still more preferably 30% to 50% by mole, with respect to all the repeating units in the resin (A).

The resin (A) may further contain the aforementioned repeating unit having a lactone structure or a sultone structure, in addition to the unit represented by General Formula (III).

The repeating unit having a lactone group or a sultone group usually has an optical isomer, and any optical isomer may be used. Further, one kind of optical isomer may be used alone or a plurality of optical isomers may be mixed and used. In the case of mainly using one kind of optical isomer, the optical purity (ee) thereof is preferably 90% or more, and more preferably 95% or more.

The content of the repeating units having a lactone structure or a sultone structure, other than the repeating units represented by General Formula (III), is preferably 15% to 60% by mole, more preferably 20% to 50% by mole, and still more preferably 30% to 50% by mole, with respect to all the repeating units in the resin in the case where the repeating units are contained in plural kinds.

In order to enhance the effects of the present invention, it is also possible to use two or more kinds of the repeating units having a lactone structure or a sultone structure selected from General Formula (III) in combination. In the case of using them in combination, it is preferable to use two or more selected from the lactone or sultone repeating units of General Formula (III) in which n is 0 in combination.

It is preferable that the resin (A) has repeating units having a hydroxyl group or a cyano group, in addition to General Formulae (AI) and (III). With the repeating units, the adhesiveness to a substrate and the developer affinity are enhanced. The repeating unit having a hydroxyl group or a cyano group is preferably a repeating unit having an alicyclic hydrocarbon structure substituted with a hydroxyl group or a cyano group, and preferably has no acid-decomposable group. An alicyclic hydrocarbon structure, in which the alicyclic hydrocarbon structure is substituted with a hydroxyl group or a cyano group, is preferably an adamantyl group, a diamantyl group, or a norbornane group. The alicyclic hydrocarbon structures which are substituted with a hydroxyl group or a cyano group are preferably partial structures represented by the following General Formulae (VIIa) to (VIId).

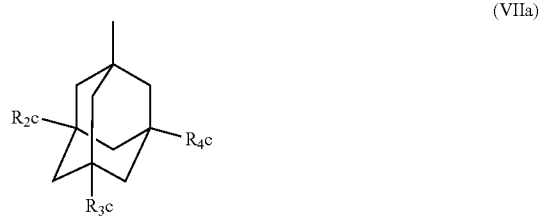

(VIIa)

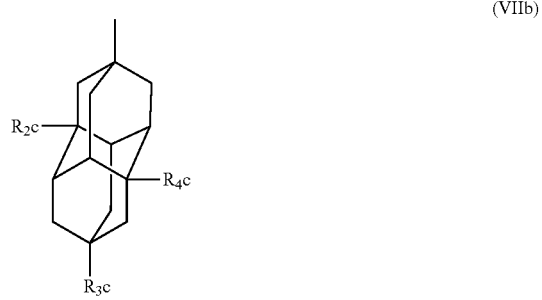

(VIIb)

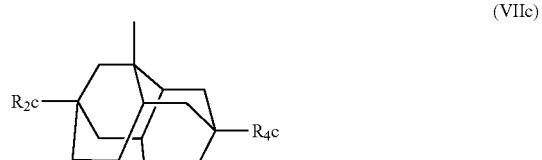

(VIIc)

(VIId)

In General Formulae (VIIa) to (VIIc), $R_2c$ to $R_4c$ each independently represent a hydrogen atom, a hydroxyl group, or a cyano group, provided that at least one of $R_2c, \ldots,$ or $R_4c$ represents a hydroxyl group or a cyano group. It is preferable that one or two members out of $R_2c$ to $R_4c$ are a hydroxyl group and the remainders are a hydrogen atom. In General Formula (VIIa), it is more preferable that two members out of $R_2c$ to $R_4c$ are hydroxyl groups and the remainder is a hydrogen atom.

Examples of the repeating unit having a partial structure represented by General Formulae (VIIa) to (VIId) include repeating units represented by the following General Formulae (AIIa) to (AIId).

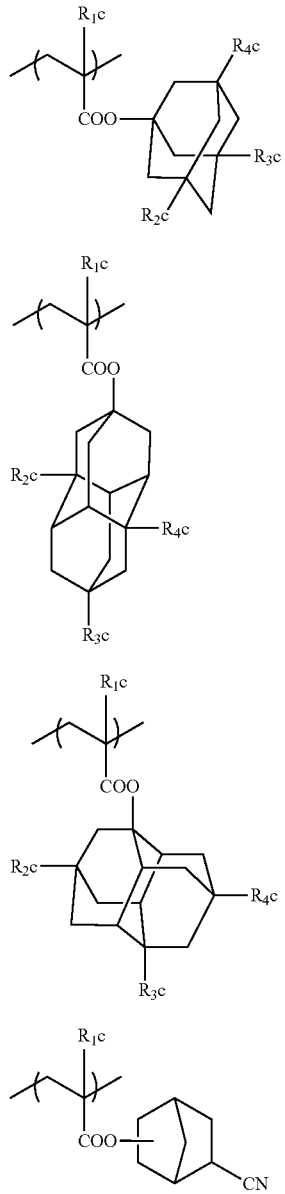

In General Formulae (AIIa) to (AIId), $R_1c$ represents a hydrogen atom, a methyl group, a trifluoromethyl group, or a hydroxymethyl group.

$R_2c$ to $R_4c$ have the same meanings as $R_2c$ to $R_4c$ in General Formulae (VIIa) to (VIIc).

The content of the repeating units having a hydroxyl group or a cyano group is preferably 5% to 40% by mole, more preferably 5% to 30% by mole, and still more preferably 10% to 25% by mole, with respect to all the repeating units in the resin (A).

Specific examples of the repeating unit having a hydroxyl group or a cyano group are shown below, but the present invention is not limited thereto.

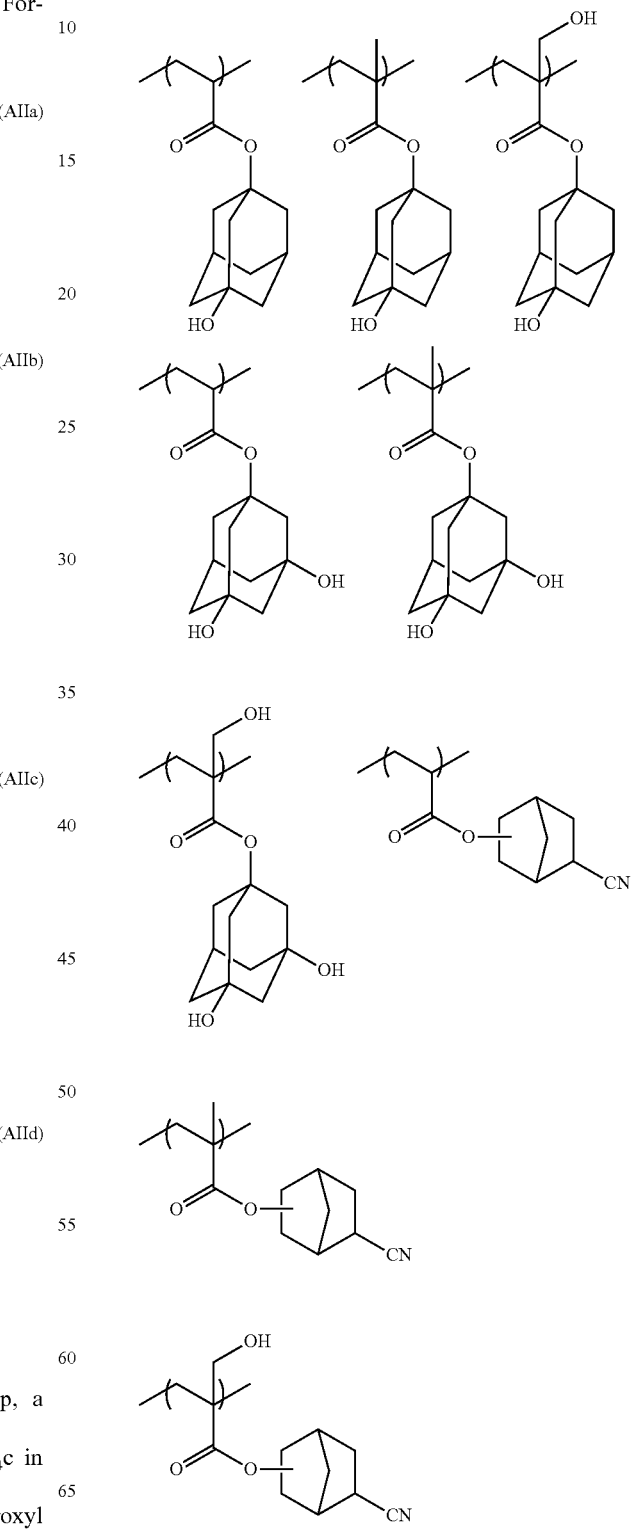

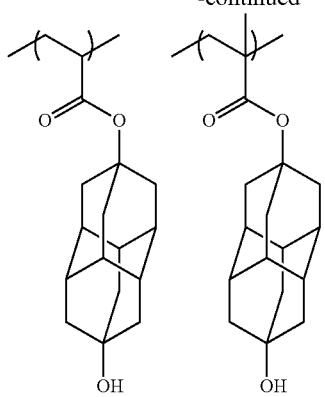

The resin (A) used in the composition of the present invention may have a repeating unit having an alkali-soluble group. Examples of the alkali-soluble group include a carboxyl group, a sulfonamide group, a sulfonylimide group, a bisulfonylimide group, and an aliphatic alcohol group with the α-position being substituted with an electron-withdrawing group (for example, a hexafluoroisopropanol group). The resin (A) more preferably has a repeating unit having a carboxyl group. By virtue of containing a repeating unit having an alkali-soluble group, the resolution increases in the usage of forming contact holes. As the repeating unit having an alkali-soluble group, all of a repeating unit in which an alkali-soluble group is directly bonded to the main chain of the resin, such as a repeating unit by an acrylic acid or a methacrylic acid, a repeating unit in which an alkali-soluble group is bonded to the main chain of the resin through a linking group, and a repeating unit in which an alkali-soluble group is introduced into the polymer chain terminal by using a polymerization initiator having an alkali-soluble group, or a chain transfer agent at the polymerization, are preferable. The linking group may have a monocyclic or polycyclic hydrocarbon structure. A repeating unit by an acrylic acid or a methacrylic acid is particularly preferable.

The content of the repeating units having an alkali-soluble group is preferably 0% to 20% by mole, more preferably 3% to 15% by mole, and still more preferably 5% to 10% by mole, with respect to all the repeating units in the resin (A).

Specific examples of the repeating unit having an alkali-soluble group are shown below, but the present invention is not limited thereto.

In the specific examples, Rx represents H, $CH_3$, $CH_2OH$, or $CF_3$.

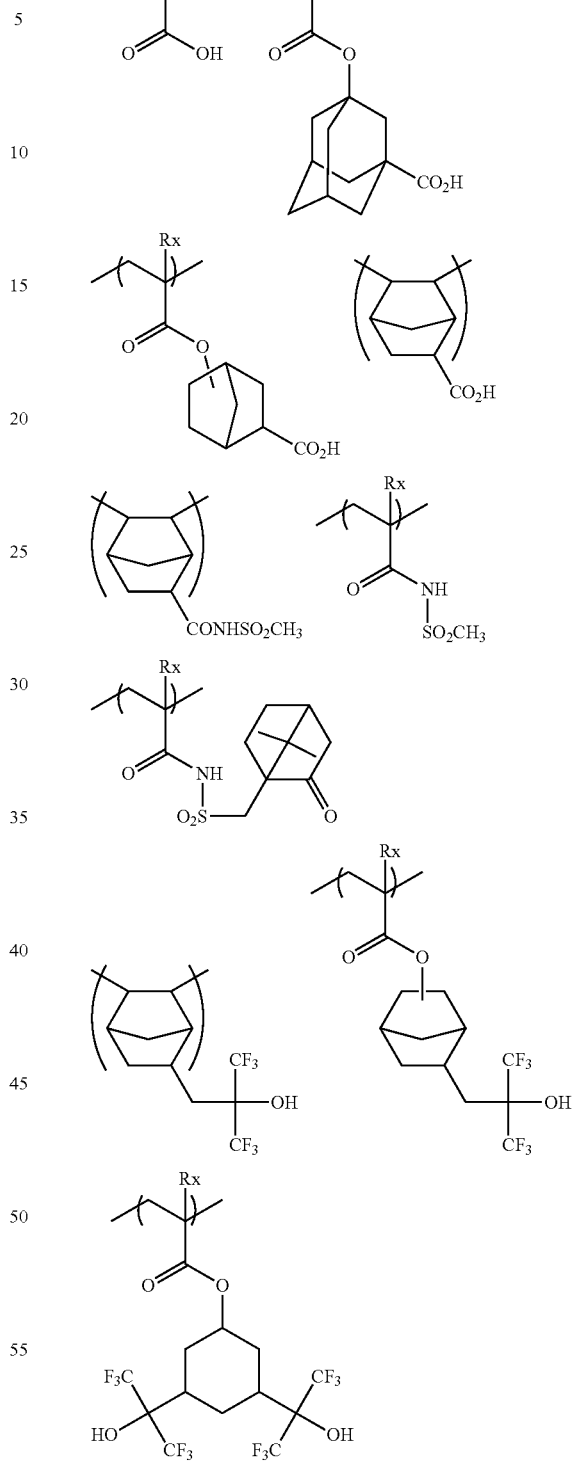

The resin (A) may further have a repeating unit which has an alicyclic hydrocarbon structure not having a polar group (for example, an alkali-soluble group, a hydroxyl group, and a cyano group) and does not exhibit acid decomposability. Examples of such a repeating unit include a repeating unit represented by General Formula (IV).

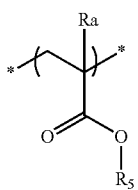

(IV)

In General Formula (IV), $R_5$ represents a hydrocarbon group having at least one cyclic structure and not having a polar group.

Ra represents a hydrogen atom, an alkyl group, or a —$CH_2$—O—$Ra_2$ group. In the formula, $Ra_2$ represents a hydrogen atom, an alkyl group, or an acyl group. $Ra_2$ is preferably a hydrogen atom, a methyl group, a hydroxymethyl group, or a trifluoromethyl group, and particularly preferably a hydrogen atom or a methyl group.

The cyclic structure contained in $R_5$ includes a monocyclic hydrocarbon group and a polycyclic hydrocarbon group. Examples of the monocyclic hydrocarbon group include a cycloalkyl group having 3 to 12 carbon atoms, such as a cyclopentyl group, a cyclohexyl group, a cycloheptyl group, and a cyclooctyl group, and a cycloalkenyl group having 3 to 12 carbon atoms, such as a cyclohexenyl group. A preferred monocyclic hydrocarbon group is a monocyclic hydrocarbon group having 3 to 7 carbon atoms, and more preferred examples thereof include a cyclopentyl group and a cyclohexyl group.

Examples of the polycyclic hydrocarbon group include a ring-assembly hydrocarbon group and a crosslinked cyclic hydrocarbon group. Examples of the ring-assembly hydrocarbon group include a bicyclohexyl group and a perhydronaphthalenyl group, and examples of the crosslinked cyclic hydrocarbon ring include bicyclic hydrocarbon rings such as a pinane ring, a bornane ring, a norpinane ring, a norbornane ring, and a bicyclooctane ring (a bicyclo[2.2.2]octane ring, a bicyclo[3.2.1]octane ring, or the like); tricyclic hydrocarbon rings such as a homobledane ring, an adamantine ring, a tricyclo[5.2.1.0$^{2,6}$]decane ring, and a tricyclo[4.3.1.1$^{2,5}$]undecane ring; and tetracyclic hydrocarbon rings such as a tetracyclo[4.4.0.1$^{2,5}$.1$^{7,10}$]dodecane ring and a perhydro-1,4-methano-5,8-methanonaphthalene ring. Other examples of the crosslinked cyclic hydrocarbon ring include fused cyclic hydrocarbon rings, and more specifically fused rings formed by fusing a plurality of 5- to 8-membered cycloalkane rings, such as a perhydronaphthalene (decalin) ring, a perhydroanthracene ring, a perhydrophenanthrene ring, a perhydroacenaphthene ring, a perhydrofluorenone ring, a perhydroindene ring, and a perhydrophenalene ring.

Preferred examples of the crosslinked cyclic hydrocarbon ring include a norbornyl group, an adamantyl group, a bicyclooctanyl group, and a tricyclo[5.2.1.0$^{2,6}$]decanyl group. More preferred examples of the crosslinked cyclic hydrocarbon rings include a norbornyl group and an adamantyl group.

These alicyclic hydrocarbon groups may have a substituent, and preferred examples of the substituent include a halogen atom, an alkyl group, a hydroxyl group with a hydrogen atom being substituted, and an amino group with a hydrogen atom being substituted. Preferred examples of the halogen atom include a bromine atom, a chlorine atom, and a fluorine atom, and preferred examples of the alkyl group include a methyl group, an ethyl group, a butyl group, and a t-butyl group. The alkyl group may further have a substituent, and examples of the substituent, which the alkyl group may further have, may include a halogen atom, an alkyl group, a hydroxyl group in which a hydrogen atom is substituted, and an amino group in which a hydrogen atom is substituted.

Examples of the group with a hydrogen atom being substituted include an alkyl group, a cycloalkyl group, an aralkyl group, a substituted methyl group, a substituted ethyl group, an alkoxycarbonyl group, and an aralkyloxycarbonyl group. Preferred examples of the alkyl group include an alkyl group having 1 to 4 carbon atoms, preferred examples of the substituted methyl group include a methoxymethyl group, a methoxythiomethyl group, a benzyloxymethyl group, a t-butoxymethyl group, and a 2-methoxyethoxymethyl group, examples of the substituted ethyl group include a 1-ethoxy ethyl group and a 1-methyl-1-methoxyethyl group, preferred examples of the acyl group include an aliphatic acyl group having 1 to 6 carbon atoms, such as a formyl group, an acetyl group, a propionyl group, a butyryl group, an isobutyryl group, a valeryl group, and a pivaloyl group, and preferred examples of the alkoxycarbonyl group include an alkoxycarbonyl group having 1 to 4 carbon atoms.

The resin (A) may or may not contain a repeating unit which has an alicyclic hydrocarbon structure having no polar group and does not exhibit acid decomposability, but when the resin (A) contains the repeating unit, the content of the repeating unit is preferably 1% to 40% by mole, and more preferably 2% to 20% by mole, with respect to all the repeating units in the resin (A).

Specific examples of the repeating unit, which has an alicyclic hydrocarbon structure not having a polar group and does not exhibit acid decomposability, are shown below, but the present invention is not limited thereto. In the formulae, Ra represents H, $CH_3$, $CH_2OH$, or $CF_3$.

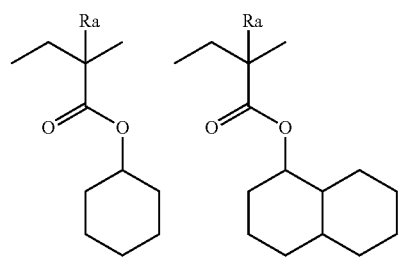

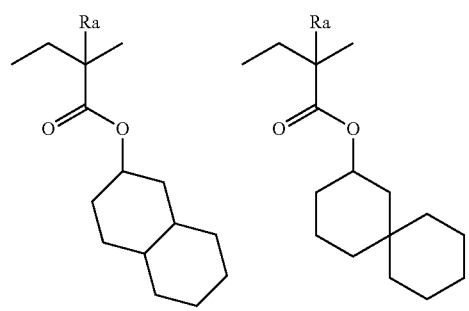

-continued

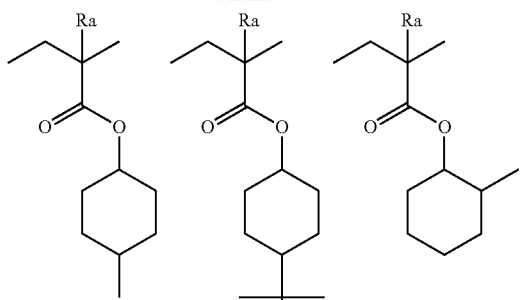
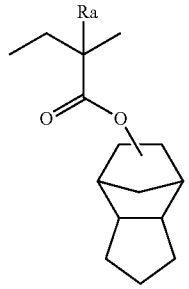
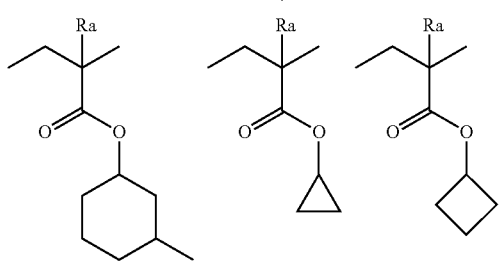
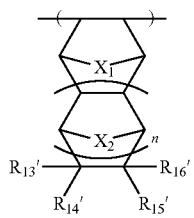
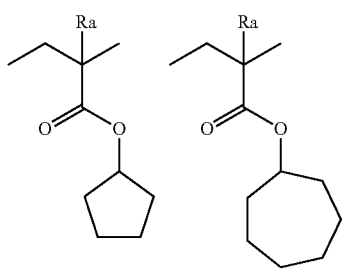
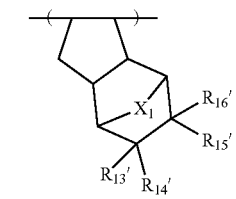
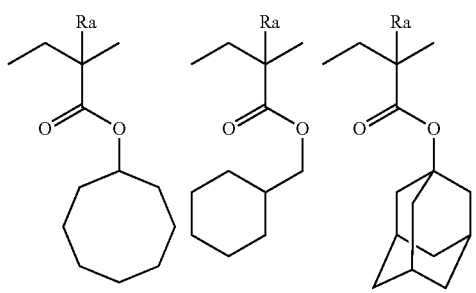
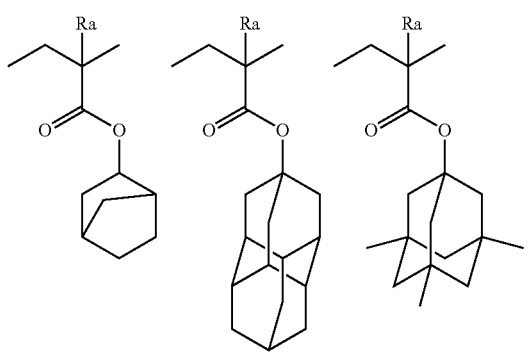

The resin (A) may contain a repeating unit represented by the following General Formula (nI) or (nII).

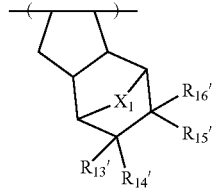

In General Formulae (nI) and (nII), $R_{13}'$ to $R_{16}'$ each independently represent a hydrogen atom, a halogen atom, a cyano group, a hydroxyl group, a carboxyl group, an alkyl group, a cycloalkyl group, an alkoxy group, an alkoxycarbonyl group, an alkylcarbonyl group, a group having a lactone structure, or a group having an acid-decomposable group.

$X_1$ and $X_2$ each independently represent a methylene group, an ethylene group, an oxygen atom, or a sulfur atom.

n represents an integer of 0 to 2.

Examples of the acid-decomposable group having an acid-decomposable group as $R_{13}'$ to $R_{16}'$ include a cumyl ester group, an enol ester group, an acetal ester group, and a tertiary alkyl ester group, and the acid-decomposable group is preferably a tertiary alkyl ester group represented by —C(=O)—O—$R_0$.

In the formula, $R_0$ represents a tertiary alkyl group such as a t-butyl group and a t-amyl group, an isobornyl group, a 1-alkoxyethyl group such as a 1-ethoxyethyl group, a 1-butoxyethyl group, a 1-isobutoxyethyl group, and a 1-cyclohexyloxyethyl group, an alkoxymethyl group such as a 1-methoxymethyl group and a 1-ethoxymethyl group, a 3-oxoalkyl group, a tetrahydropyranyl group, a tetrahydrofuranyl group, a trialkylsilyl ester group, a 3-oxocyclohexyl ester group, a 2-methyl-2-adamantyl group, and a mevalonic lactone residue.

At least one of $R_{13}'$, . . . , or $R_{16}'$ is preferably a group having an acid-decomposable group.

Examples of the halogen atom in $R_{13}'$ to $R_{16}'$ include a chlorine atom, a bromine atom, a fluorine atom, and an iodine atom.

The alkyl group of $R_{13}'$ to $R_{16}'$ is more preferably a group represented by the following General Formula (F1).

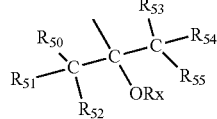
(F1)

In General Formula (F1), $R_{50}$ to $R_{55}$ each independently represent a hydrogen atom, a fluorine atom, or an alkyl group. However, at least one of $R_{50}, \ldots,$ or $R_{55}$ represents a fluorine atom or an alkyl group having at least one hydrogen atom substituted with a fluorine atom; and Rx represents a hydrogen atom or an organic group (preferably an acid-decomposable protecting group, an alkyl group, a cycloalkyl group, an acyl group, or an alkoxycarbonyl group), and preferably a hydrogen atom.

It is preferable that all of $R_{50}$ to $R_{55}$ are fluorine atoms.

Examples of the repeating unit represented by General Formula (nI) or General Formula (nII) include the following specific examples, but the present invention is not limited to these compounds. Among those, repeating units represented by (II-f-16) to (II-f-19) are preferable.

(II-a-1)
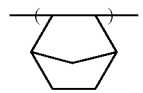

(II-a-2)
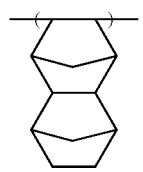

(II-a-3)
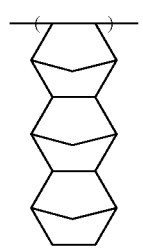

(II-a-4)
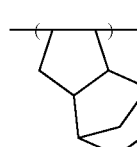

(II-a-5)
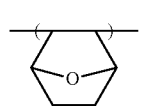

(II-a-6)
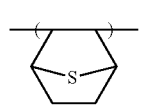

(II-a-7)
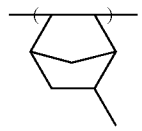

(II-a-8)
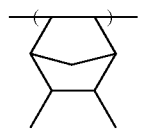

(II-a-9)
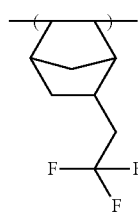

(II-a-10)
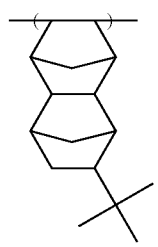

(II-a-11)
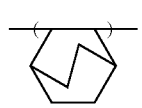

(II-a-12)
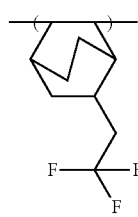

(II-a-13)
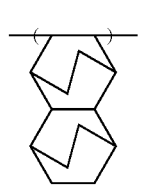

(II-a-14)
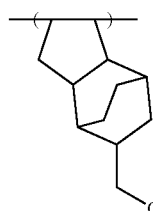

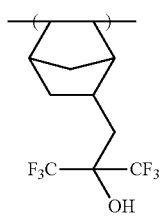
(II-b-1)
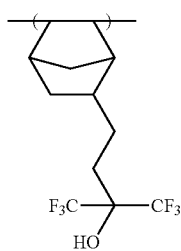
(II-b-2)
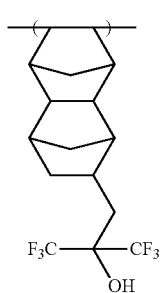
(II-b-3)
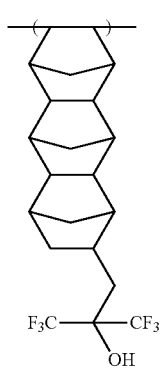
(II-b-4)
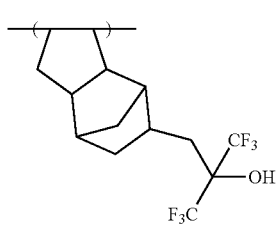
(II-b-5)
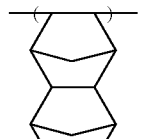
(II-b-6)
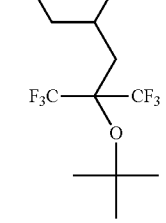
(II-b-7)
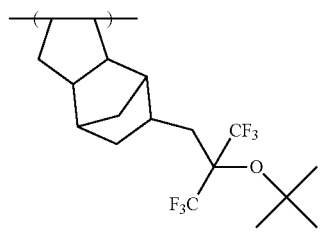
(II-b-8)
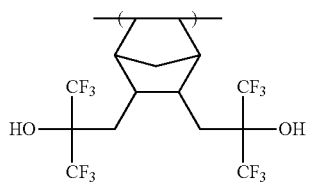
(II-b-9)
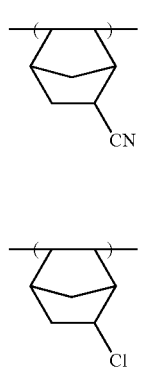
(II-c-1)
(II-c-2)
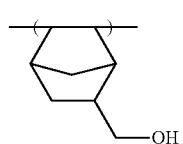
(II-c-3)

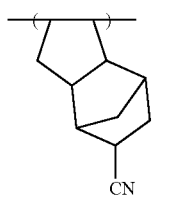
(II-c-4)
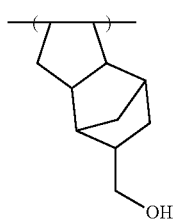
(II-c-5)
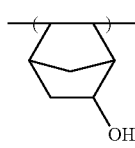
(II-c-6)
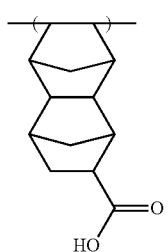
(II-c-7)
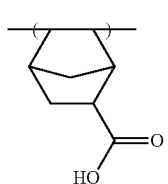
(II-c-8)
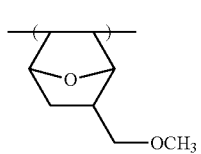
(II-c-9)
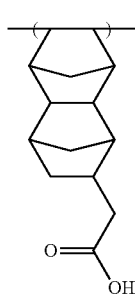
(II-c-10)
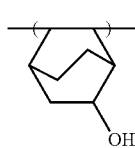
(II-c-11)
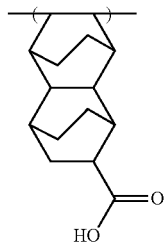
(II-c-12)
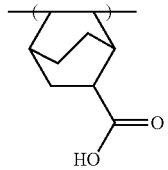
(II-c-13)
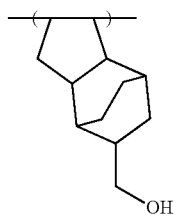
(II-c-14)
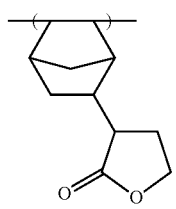
(II-d-1)
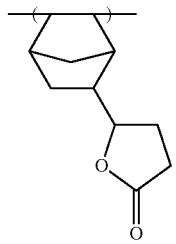
(II-d-2)
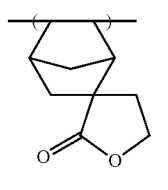
(II-d-3)
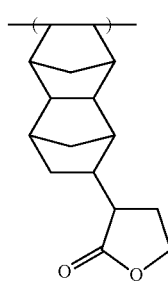
(II-d-4)

(II-d-5)
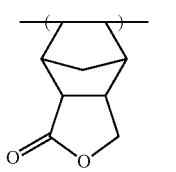
(II-d-6)
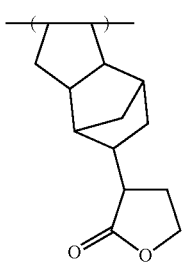
(II-d-7)
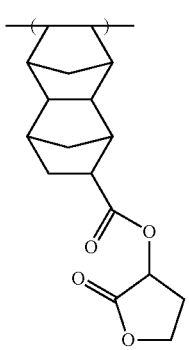
(II-d-8)
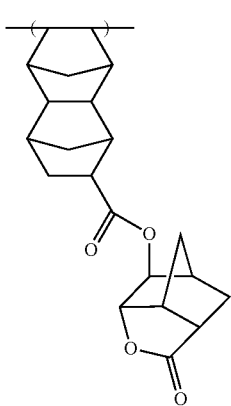
(II-d-9)
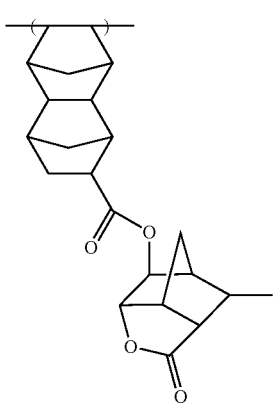
(II-e-1)
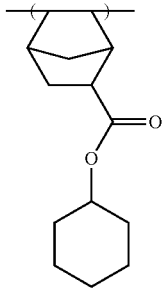
(II-e-2)
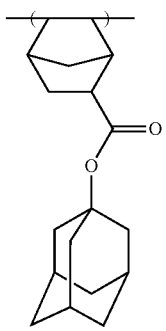
(II-e-3)
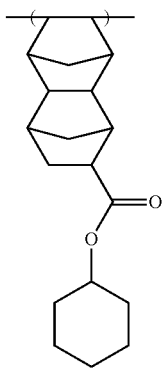
(II-e-4)
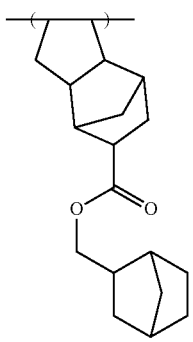

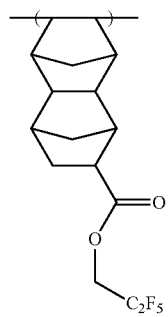 (II-e-5)
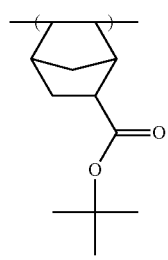 (II-f-1)
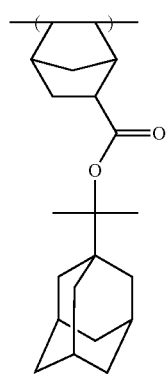 (II-f-2)
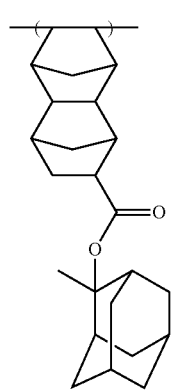 (II-f-3)
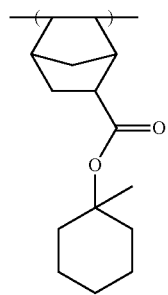 (II-f-4)
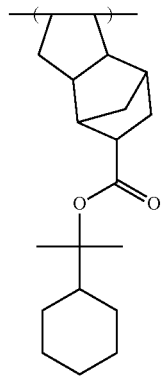 (II-f-5)
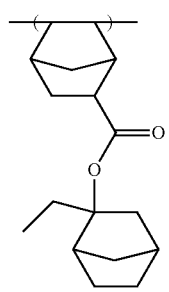 (II-f-6)
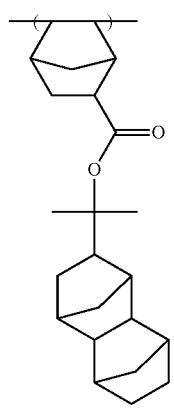 (II-f-7)
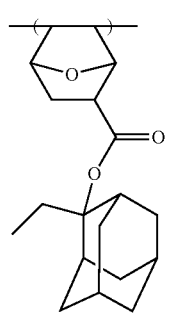 (II-f-8)

(II-f-9)
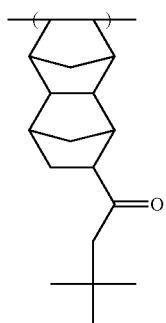
(II-f-10)
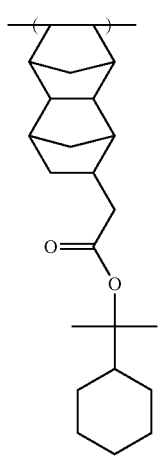
(II-f-11)
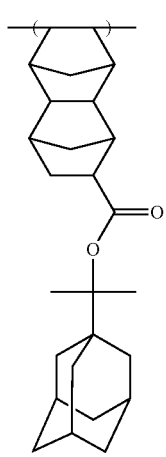
(II-f-12)
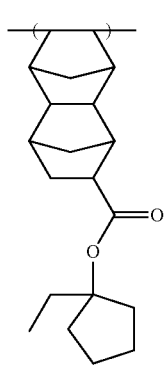
(II-f-13)
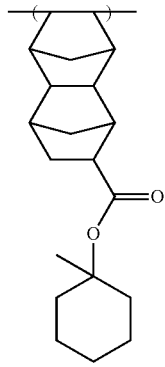
(II-f-14)
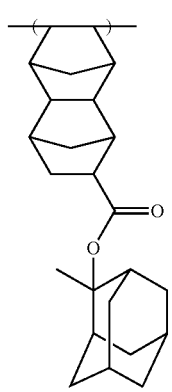
(II-f-15)
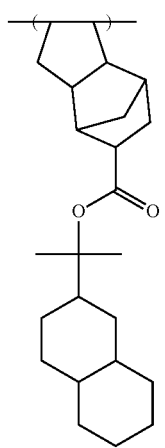
(II-f-16)
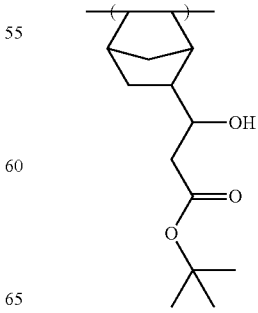

-continued

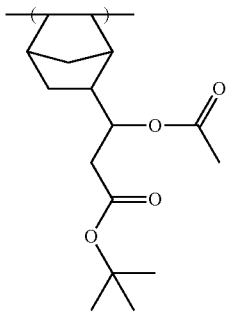
(II-f-17)

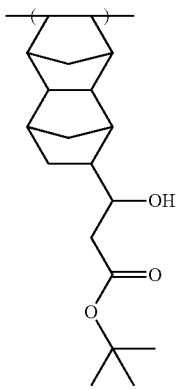
(II-f-18)

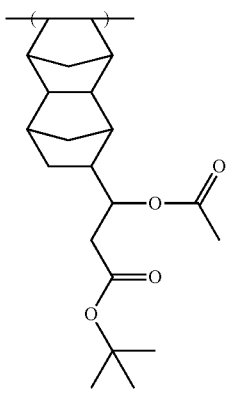
(II-f-19)

In addition to the repeating structural units, the resin (A) used in the composition of the present invention can have a variety of repeating structural units for the purpose of adjusting dry etching resistance, suitability for a standard developer, adhesiveness to a substrate, and a resist profile, and in addition, resolving power, heat resistance, sensitivity, and the like, which are characteristics generally required for the resist. Examples of such repeating structural units include, but are not limited to, repeating structural units corresponding to the following monomers.

Thus, it becomes possible to perform fine adjustments to performance required for the resin used in the composition of the present invention, in particular, (1) solubility with respect to a coating solvent, (2) film-forming properties (glass transition point), (3) alkali developability, (4) film reduction (selection of hydrophilic, hydrophobic, or alkali-soluble groups), (5) adhesiveness of an unexposed area to a substrate, (6) dry etching resistance, and the like.

Examples of such a monomer include a compound having one addition-polymerizable unsaturated bond selected from acrylic esters, methacrylic esters, acrylamides, a methacrylamides, allyl compounds, vinyl ethers, and vinyl esters.

In addition to these, an addition-polymerizable unsaturated compound that is copolymerizable with the monomers corresponding to various repeating structural units as described above may be copolymerized.

In the resin (A) used in the composition of the present invention, the molar ratio of each repeating structural unit content is appropriately set in order to adjust dry etching resistance, suitability for a standard developer, adhesiveness to a substrate, and a resist profile of the resist, and in addition, resolving power, heat resistance, sensitivity, and the like, each of which is performance generally required for the resist.

When the composition of the present invention is for ArF exposure, it is preferable that the resin (A) used in the composition of the present invention has substantially no aromatic groups in terms of transparency to ArF light. More specifically, the proportion of repeating units having an aromatic group in all the repeating units of the resin (A) is preferably 5% by mole or less, more preferably 3% by mole or less, and ideally 0% by mole of all the repeating units, that is, the resin (A) does not have a repeating unit having an aromatic group. Further, it is preferable that the resin (A) has a monocyclic or polycyclic alicyclic hydrocarbon structure.

In the case of irradiating the composition of the present invention with KrF excimer laser light, electron beams, X-rays, or high-energy beams at a wavelength of 50 nm or less (for example, EUV), it is preferable that the resin (A) contains a hydroxystyrene repeating unit. The resin (A) is more preferably a copolymer of hydroxystyrene with hydroxystyrene protected with a group capable of leaving by the action of an acid, or a copolymer of hydroxystyrene with a tertiary alkyl (meth)acrylate ester.

Specific examples of such a resin include a resin having a repeating unit represented by the following General Formula (A).

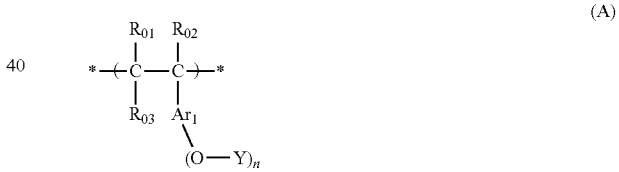
(A)

In the formula, $R_{01}$, $R_{02}$, and $R_{03}$ each independently represent a for example, a hydrogen atom, an alkyl group, a cycloalkyl group, a halogen atom, a cyano group, or an alkoxycarbonyl group. $Ar_1$ represents, for example, an aromatic ring group. Further, $R_{03}$ and $Ar_1$ are each an alkylene group, and they both may be bonded to each other, together with a —C—C— chain, to form a 5- or 6-membered ring.

Y's in the number of n each independently represent a hydrogen atom or a group capable of leaving by an action of an acid, provided that at least one of Y's represents a group capable of leaving by an action of an acid.

n represents an integer of 1 to 4, and is preferably 1 or 2, and more preferably 1.

The alkyl group as $R_{01}$ to $R_{03}$ is, for example, preferably an alkyl group having 20 or less carbon atoms, preferably a methyl group, an ethyl group, a propyl group, an isopropyl group, an n-butyl group, a sec-butyl group, a hexyl group, a 2-ethylhexyl group, an octyl group, or a dodecyl group, and more preferably an alkyl group having 8 or less carbon atoms. Further, these alkyl groups may have substituents.

The alkyl group included in the alkoxycarbonyl group is preferably the same as the alkyl group in $R_{01}$ to $R_{03}$.

The cycloalkyl group may be a monocyclic cycloalkyl group or a polycyclic cycloalkyl group. Preferred examples thereof include a monocyclic cycloalkyl group having 3 to 8 carbon atoms, such as a cyclopropyl group, a cyclopentyl group, and a cyclohexyl group. Further, these cycloalkyl groups may have a substituent.

Examples of the halogen atom include a fluorine atom, a chlorine atom, a bromine atom, and an iodine atom, and a fluorine atom is more preferable.

In the case where $R_{03}$ represents an alkylene group, preferred examples of the alkylene group include ones having 1 to 8 carbon atoms, such as a methylene group, an ethylene group, a propylene group, a butylene group, a hexylene group, and an octylene group.

The aromatic ring as $Ar_1$ is preferably one having 6 to 14 carbon atoms, and examples thereof include a benzene ring, a toluene ring, and a naphthalene ring. Here, these aromatic ring groups may have a substituent.

Examples of the group Y capable of leaving by an action of an acid include a group represented by —C($R_{36}$)($R_{37}$)($R_{38}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$), or —CH($R_{36}$)(Ar).

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring structure.

$R_{01}$ and $R_{02}$ each independently represent a hydrogen atom, an alkyl group, a cycloalkyl group, an aryl group, an aralkyl group, or an alkenyl group.

Ar represents an aryl group.

As the alkyl group as $R_{36}$ to $R_{39}$, $R_{01}$, or $R_{02}$, an alkyl group having 1 to 8 carbon atoms is preferable, and examples thereof include a methyl group, an ethyl group, a propyl group, an n-butyl group, a sec-butyl group, a hexyl group, and an octyl group.

The cycloalkyl group as $R_{36}$ to $R_{39}$, $R_{01}$, or $R_{02}$ may be a monocyclic cycloalkyl group or a polycyclic cycloalkyl group. As the monocyclic cycloalkyl group, a cycloalkyl group having 3 to 8 carbon atoms is preferable, and examples thereof include a cyclopropyl group, a cyclobutyl group, a cyclopentyl group, a cyclohexyl group, and cyclooctyl group. As the polycyclic cycloalkyl group, a cycloalkyl group having 6 to 20 carbon atoms is preferable, and examples thereof include an adamantyl group, a norbornyl group, an isobornyl group, a camphonyl group, a dicyclopentyl group, an α-pinanyl group, a tricyclodecanyl group, a tetracyclododecyl group, and an androstanyl group. Further, some of the carbon atoms in the cycloalkyl group may be substituted with hetero atoms such as an oxygen atom.

The aryl group as $R_{36}$ to $R_{39}$, $R_{01}$, $R_{02}$, or Ar is preferably an aryl group with 6 to 10 carbon atoms and examples thereof include a phenyl group, a naphthyl group, and an anthryl group.

The aralkyl group as $R_{36}$ to $R_{39}$, $R_{01}$, or $R_{02}$ is preferably an aralkyl group with 7 to 12 carbon atoms and for example, a benzyl group, a phenethyl group, and a naphthylmethyl group are preferable.

The alkenyl group as $R_{36}$ to $R_{39}$, $R_{01}$, or $R_{02}$ is preferably an alkenyl group with 2 to 8 carbon atoms and examples thereof include a vinyl group, an allyl group, a butenyl group, and a cyclohexenyl group.

A ring which can be formed by the mutual bonding of $R_{36}$ and $R_{37}$ may be monocyclic or may be polycyclic. As the monocyclic ring, a cycloalkane structure having 3 to 8 carbon atoms is preferable, and examples thereof include a cyclopropane structure, a cyclobutane structure, a cyclopentane structure, a cyclohexane structure, a cycloheptane structure, and a cyclooctane structure. As the polycyclic ring, a cycloalkane structure having 6 to 20 carbon atoms is preferable, and examples thereof include an adamantane structure, a norbornane structure, a dicyclopentane structure, a tricyclodecane structure, and a tetracyclododecane structure. Further, a part of the carbon atoms in the ring structure may be substituted with hetero atoms such as an oxygen atom.

The respective groups described above may have a substituent. Examples of the substituent include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. These substituents preferably have 8 or less carbon atoms.

As the group Y capable of leaving by an action of an acid, a structure represented by the following General Formula (B) is more preferable.

(B)

In the formula, $L_1$ and $L_2$ each independently represent a hydrogen atom, an alkyl group, a cycloalkyl group, an aryl group, or an aralkyl group.

M represents a single bond or a divalent linking group.

Q represents an alkyl group, a cycloalkyl group, a cyclic aliphatic group, an aromatic ring group, an amino group, an ammonium group, a mercapto group, a cyano group, or an aldehyde group. Further, these cyclic aliphatic groups and aromatic ring groups may include hetero atoms.

Furthermore, at least two members out of Q, M, and $L_1$ may be bonded to each other to form a 5- or 6-membered ring.

The alkyl group as $L_1$ and $L_2$ is, for example, an alkyl group having 1 to 8 carbon atoms, and specific examples thereof include a methyl group, an ethyl group, a propyl group, an n-butyl group, a sec-butyl group, a hexyl group, and an octyl group.

The cycloalkyl group as $L_1$ and $L_2$ is, for example, a cycloalkyl group having 3 to 15 carbon atoms, and specific examples thereof include a cyclopentyl group, a cyclohexyl group, a norbornyl group, and an adamantyl group.

The aryl group as $L_1$ and $L_2$ is, for example, an aryl group with 6 to 15 carbon atoms, and specific examples thereof include a phenyl group, a tolyl group, a naphthyl group, and an anthryl group.

The aralkyl group as $L_1$ and $L_2$ is, for example, an aralkyl group having 6 to 20 carbon atoms, and specific examples thereof include a benzyl group and a phenethyl group.

The divalent linking group as M is, for example, an alkylene group (for example, a methylene group, an ethylene group, a propylene group, a butylene group, a hexylene group, or an octylene group), a cycloalkylene group (for example, a cyclopentylene group or a cyclohexylene group), an alkenylene group (for example, an ethylene group, a propenylene group, or a butenylene group), an arylene group (for example, a phenylene group, a tolylene group, or a naphthylene group), —S—, —O—, —CO—, —SO$_2$—, —N($R_0$)—, and a combination of two or more thereof. Here, R₀ is a hydrogen atom or an alkyl group. The alkyl group as R₀ is, for example, an alkyl group having a number of carbon atoms of 1 to 8, and specific examples thereof include a methyl group, an ethyl group, a propyl group, an n-butyl group, a sec-butyl group, a hexyl group, and an octyl group.

The alkyl group and the cycloalkyl group as Q are the same as the respective groups as $L_1$ and $L_2$ described above.

Examples of the cyclic aliphatic group or the aromatic ring group as Q include the cycloalkyl group and the aryl group as $L_1$ and $L_2$ described above. The cycloalkyl group and the aryl group are preferably groups having 3 to 15 carbon atoms.

Examples of the cyclic aliphatic group or the aromatic ring group, containing a hetero atom, as Q include groups such as thiirane, cyclothiolane, thiophene, furan, pyrrole, benzothiophene, benzofuran, benzopyrrole, triazine, imidazole, benzimidazole, triazole, thiadiazole, thiazole, pyrrolidone, and the like which have a heterocyclic structure. However, the cyclic aliphatic group or the aromatic ring group is not limited thereto as long as it is a ring which is formed by carbon and hetero atoms or a ring which is formed by only hetero atoms.

Examples of a ring structure which at least two members out of Q, M, and $L_1$ may form by being bonded to each other include a 5- or 6-membered ring structure which is formed by these forming a propylene group or a butylene group. Here, the 5- or 6-membered ring structure contains an oxygen atom.

Each of the groups represented by $L_1$, $L_2$, M, and Q in General Formula (B) may have a substituent. Examples of the substituent include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. The substituents preferably have 8 or less carbon atoms.

As the group represented by -(M-Q), a group having 1 to 20 carbon atoms is preferable, a group having 1 to 10 carbon atoms is more preferable, and a group having 1 to 8 carbon atoms is still more preferable.

Specific examples of the resin (A) having hydroxystyrene repeating units are shown below, but the present invention is not limited thereto.

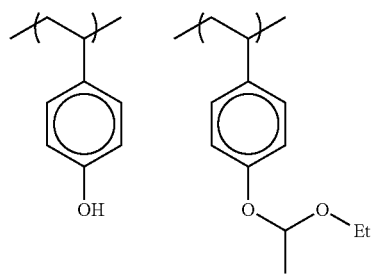
(R-1)

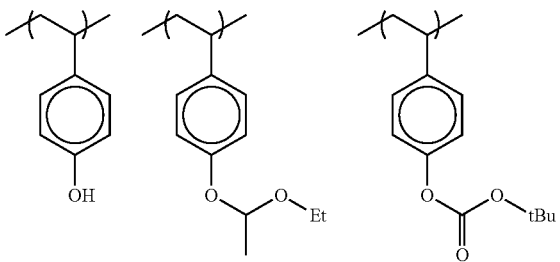
(R-2)

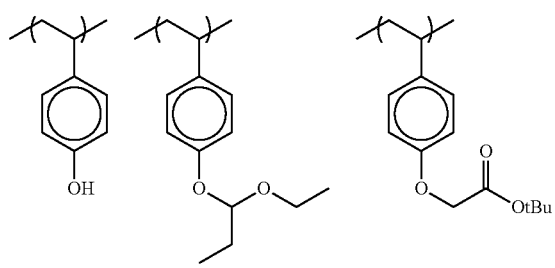
(R-3)

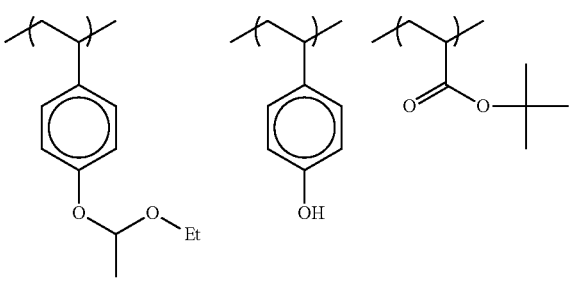
(R-4)

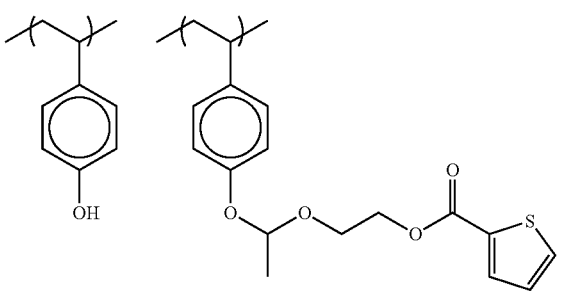
(R-5)

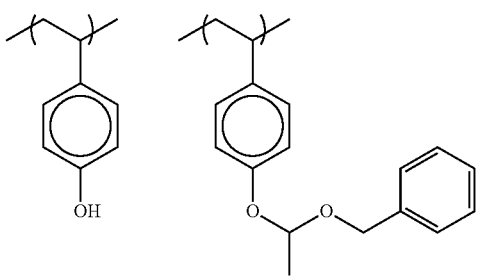
(R-6)

(R-7)
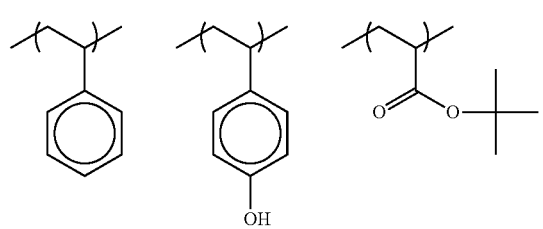
(R-8)
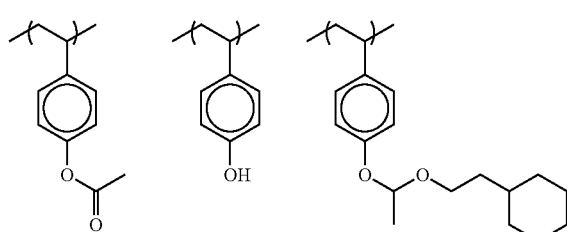
(R-9)
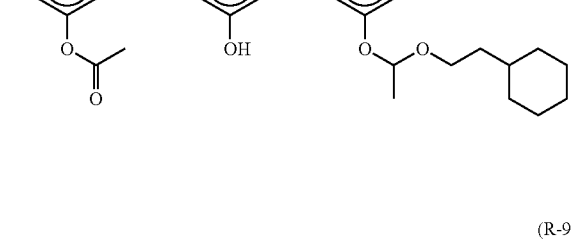
(R-10)
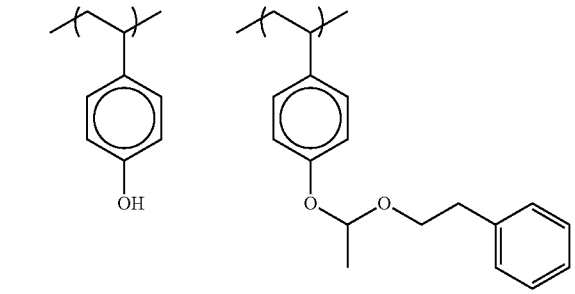
(R-11)
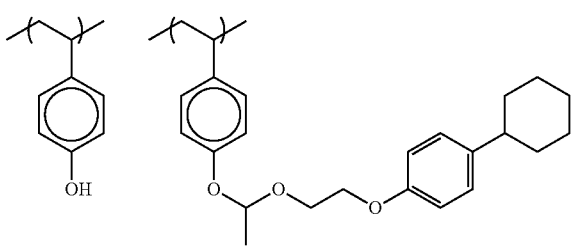
(R-12)
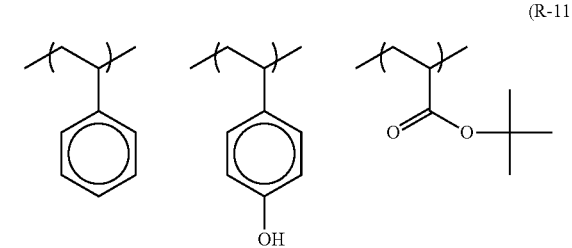
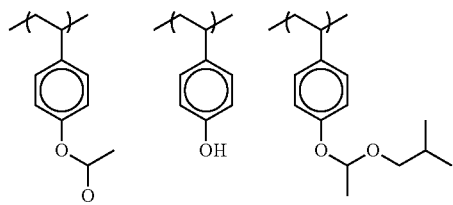
(R-13)
(R-14)
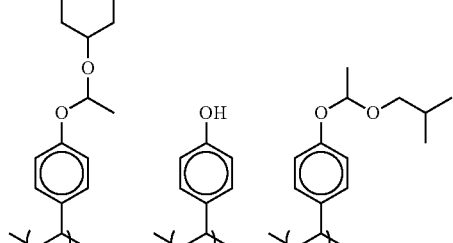
(R-15)
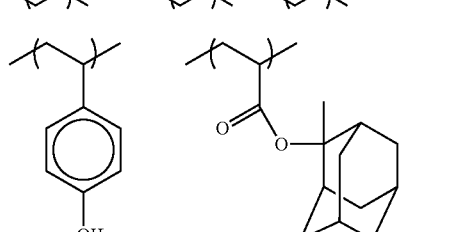
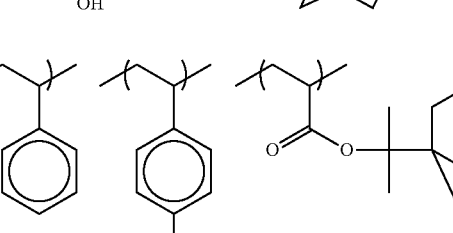
(R-16)
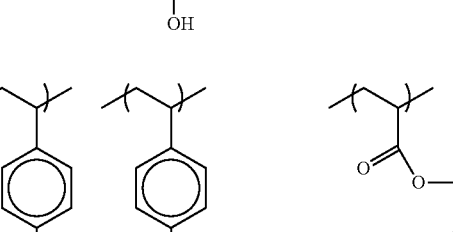
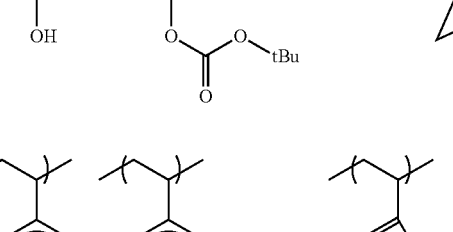
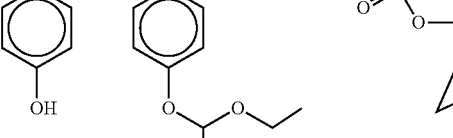

(R-17)
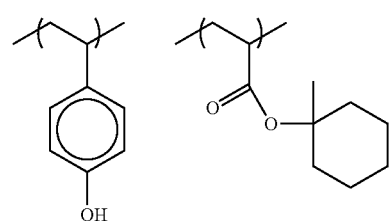
R-22
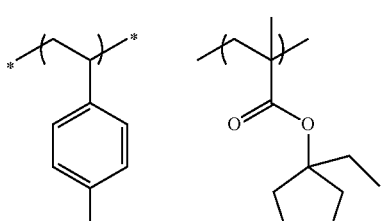
(R-18)
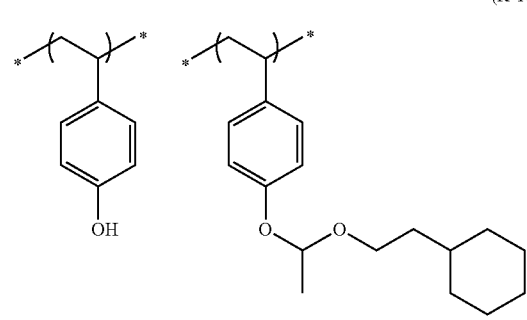
R-23
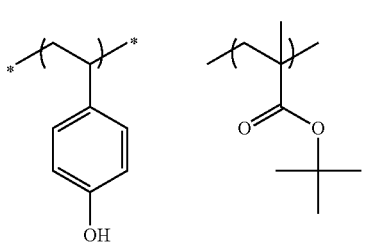
(R-19)
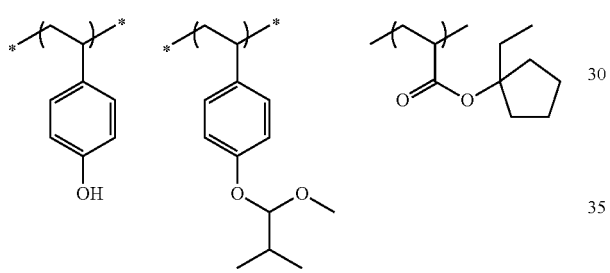
R-24
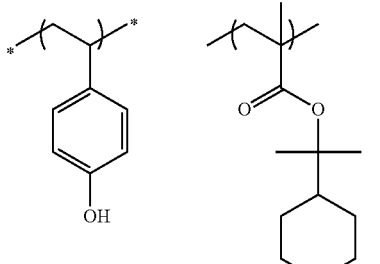
(R-20)
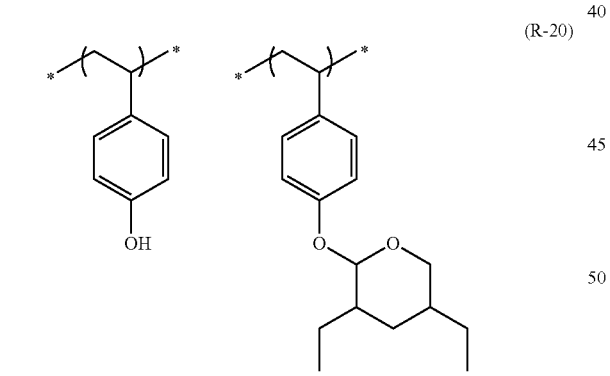
R-25
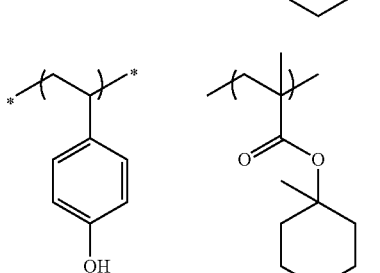
R-26
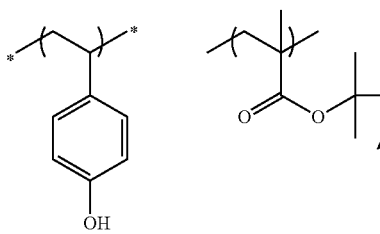
R-21
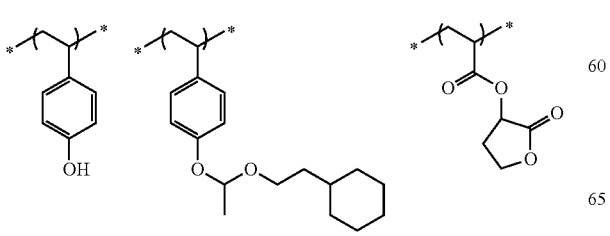
R-27
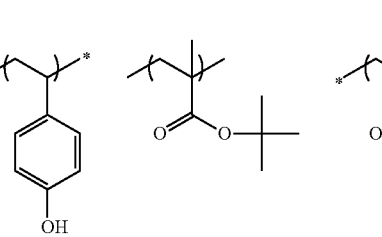

-continued

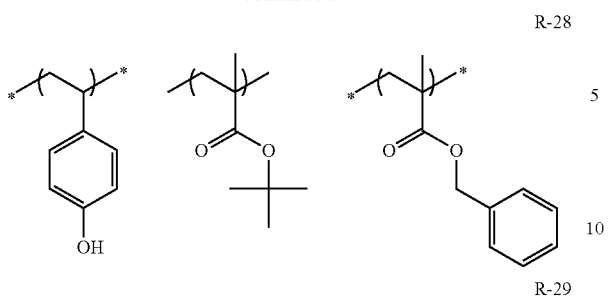
R-28

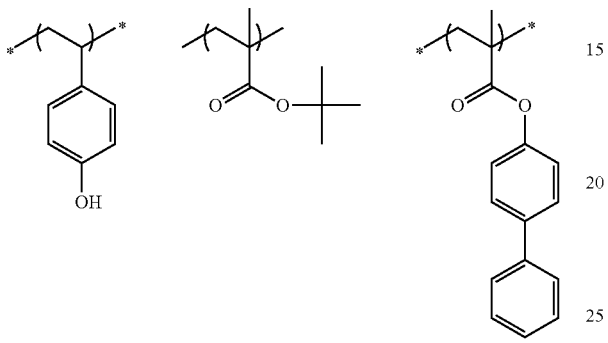
R-29

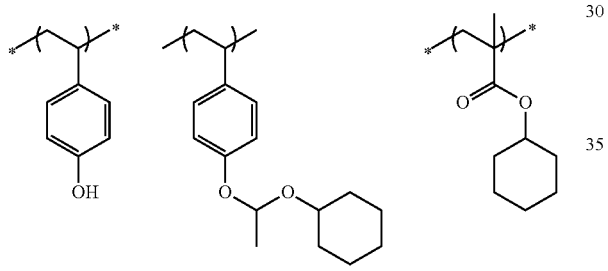
R-30

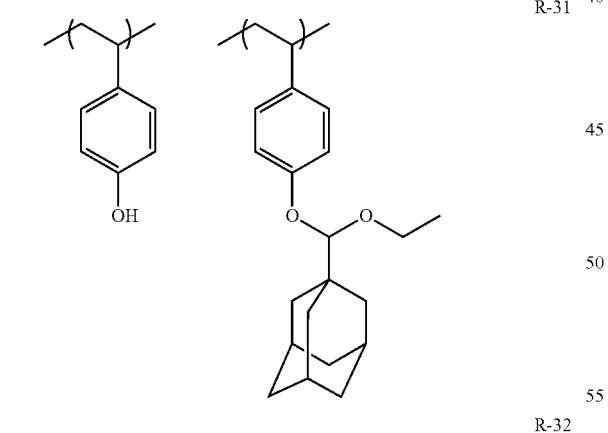
R-31

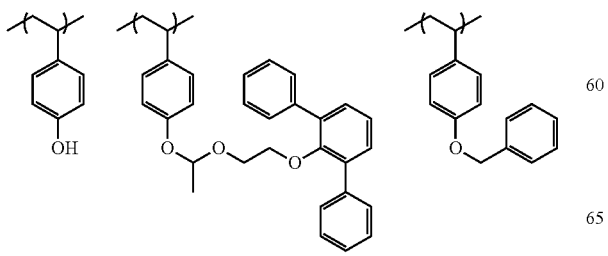
R-32

-continued

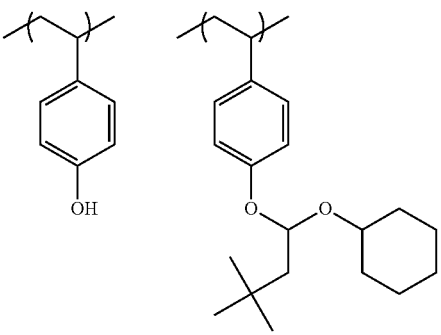
R-33

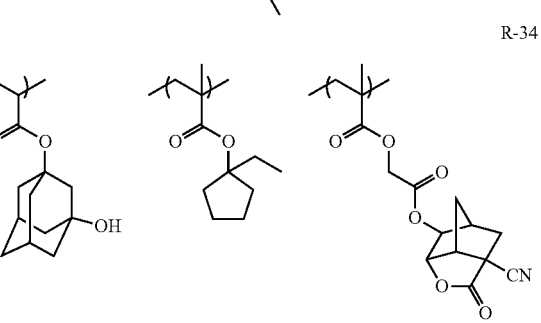
R-34

In these specific examples, tBu represents a t-butyl group.

Furthermore, it is preferable that the resin (A) contains neither a fluorine atom nor a silicon atom from the viewpoint of compatibility with a hydrophobic resin which will be described later.

The resin (A) used in composition of the present invention is preferably a resin in which all the repeating units are composed of (meth)acrylate-based repeating units. In this case, all the repeating units may be methacrylate-based repeating units, all the repeating units may be acrylate-based repeating units, or all the repeating units may be composed of methacrylate-based repeating units and acrylate-based repeating units, but the acrylate-based repeating units preferably accounts for 50% by mole or less with respect to all the repeating units. Further, a copolymerization polymer including 20% to 50% by mole a (meth)acrylate-based repeating unit having an acid-decomposable group, 20% to 50% by mole of a (meth)acrylate-based repeating unit having a lactone group, and 5% to 30% by mole of a (meth)acrylate-based repeating unit having an alicyclic hydrocarbon structure substituted with a hydroxyl group or cyano group, and in addition to these, 0% to 20% by mole of other (meth)acrylate-based repeating units are also preferable.

The resin (A) in the present invention can be synthesized in accordance with an ordinary method (for example, radical polymerization). Examples of the general synthesis method include a bulk polymerization method in which polymerization is carried out by dissolving monomer species and an initiator in a solvent and heating the solution, a dropwise addition polymerization method in which a solution of monomer species and an initiator is added dropwise to a heating solvent for 1 to 10 hours, with the dropwise addition polymerization method being preferable. Examples of the reaction solvent include ethers such as tetrahydrofuran, 1,4-dioxane, and diisopropyl ether, ketones such as methyl ethyl ketone and methyl isobutyl ketone, ester solvents such as ethyl acetate, amide solvents such as dimethyl formamide and dimethyl acetamide, and a solvent which dissolves the composition of the present invention, such as propylene glycol monomethyl ether acetate, propylene glycol monomethyl ether, and cyclohexanone, which will be described later. It is more preferable to perform polymerization using the same solvent as the solvent used in the composition of the present invention. Thus, generation of the particles during storage can be inhibited.

It is preferable that the polymerization reaction is carried out in an inert gas atmosphere such as nitrogen and argon. As the polymerization initiator, commercially available radical initiators (an azo-based initiator, peroxide, or the like) are used to initiate the polymerization. As the radical initiator, an azo-based initiator is preferable, and the azo-based initiator having an ester group, a cyano group, or a carboxyl group is preferable. Preferable initiators include azobisisobutyronitrile, azobisdimethylvaleronitrile, dimethyl 2,2'-azobis(2-methyl propionate), or the like. The initiator is added or added in portionwise, as desired, a desired polymer is recovered after the reaction is completed, the reaction mixture is poured into a solvent, and then a method such as powder or solid recovery is used. The concentration of the reactant is 5% to 50% by mass and preferably 10% to 30% by mass. The reaction temperature is normally 10° C. to 150° C., preferably 30° C. to 120° C., and more preferably 60° C. to 100° C.

The weight-average molecular weight of the resin (A) in the present invention is preferably 1,000 to 200,000, more preferably 2,000 to 20,000, still more preferably 3,000 to 15,000, and particularly preferably 3,000 to 11,000 in terms of polystyrene by means of a GPC method. By setting the weight-average molecular weight to 1,000 to 200,000, it is possible to prevent the deterioration of heat resistance or dry-etching resistance, and also prevent the deterioration of film forming properties due to deterioration of developability or increased viscosity.

The dispersity (molecular weight distribution) is usually 1.0 to 3.0, preferably in the range of 1.0 to 2.6, more preferably in the range of 1.0 to 2.0, and particularly preferably in the range of 1.1 to 2.0. The smaller the molecular weight distribution is, the better the resolution and the resist shape are, the smoother the side wall of the resist pattern is, and the better roughness is.

The content of the resin (A) in the total composition is preferably 30% to 99% by mass, and more preferably 50% to 95% by mass, with respect to the total solid contents.

In addition, the resin (A) may be used alone or in combination of two or more kinds thereof.

<Hydrophobic Resin>

The composition of the present invention may contain a hydrophobic resin. Further, the hydrophobic resin is preferably different from the resin (A).

Although the hydrophobic resin is preferably designed to be unevenly localized on an interface as described above, it does not necessarily have to have a hydrophilic group in its molecule as different from the surfactant, and does not need to contribute to uniform mixing of polar/nonpolar materials.

Examples of the effect of addition of the hydrophobic resin include control of the static/dynamic contact angle of the resist film surface with respect to water, improvement of the immersion liquid tracking properties, and inhibition of out gas.

The hydrophobic resin preferably has at least one of a "fluorine atom", a "silicon atom", or a "$CH_3$ partial structure which is contained in a side chain portion of a resin" from the point of view of uneven distribution on the film surface layer, and more preferably has two or more kinds.

In the case where hydrophobic resin contains a fluorine atom and/or a silicon atom, the fluorine atom and/or the silicon atom in the hydrophobic resin may be contained in the main chain or the side chain of the resin.

In the case where the hydrophobic resin contains a fluorine atom, the resin is preferably a resin which contains an alkyl group having a fluorine atom, a cycloalkyl group having a fluorine atom, or an aryl group having a fluorine atom, as a partial structure having a fluorine atom.

The alkyl group having a fluorine atom (preferably having 1 to 10 carbon atoms, and more preferably having 1 to 4 carbon atoms) is a linear or branched alkyl group in which at least one hydrogen atom is substituted with a fluorine atom, and may further have a substituent other than a fluorine atom.

The cycloalkyl group having a fluorine atom is a monocyclic or polycyclic cycloalkyl group in which at least one hydrogen atom is substituted with a fluorine atom, and may further have a substituent other than a fluorine atom.

The aryl group having a fluorine atom is an aryl group such as a phenyl group and a naphthyl group, in which at least one hydrogen atom is substituted with a fluorine atom, and may further have a substituent other than a fluorine atom.

Preferred examples of the alkyl group having a fluorine atom, the cycloalkyl group having a fluorine atom, and the aryl group having a fluorine atom include groups represented by the following General Formulae (F2) to (F4), but the present invention is not limited thereto.

In General Formulae (F2) to (F4), $R_{57}$ to $R_{68}$ each independently represent a hydrogen atom, a fluorine atom, or an (linear or branched) alkyl group, provided that at least one of $R_{57}, \ldots,$ or $R_{61}$, at least one of $R_{62}, \ldots,$ or $R_{64}$, and at least one of $R_{65}, \ldots,$ or $R_{68}$ each independently represent a fluorine atom or an alkyl group (preferably having 1 to 4 carbon atoms) in which at least one hydrogen atom is substituted with a fluorine atom.

It is preferable that all of $R_{57}$ to $R_{61}$, and $R_{65}$ to $R_{67}$ are fluorine atoms. $R_{62}$, $R_{63}$, and $R_{68}$ are each preferably an alkyl group (preferably having 1 to 4 carbon atoms) in which at least one hydrogen atom is substituted with a fluorine atom, and more preferably a perfluoroalkyl group having 1 to 4 carbon atoms. $R_{62}$ and $R_{63}$ may be linked to each other to form a ring.

Specific examples of the group represented by General Formula (F2) include a p-fluorophenyl group, a pentafluorophenyl group, and a 3,5-di(trifluoromethyl)phenyl group.

Specific examples of the group represented by General Formula (F3) include those exemplified in [0500] of US2012/0251948A1.

Specific examples of the group represented by General Formula (F4) include —C(CF$_3$)$_2$OH, —C(C$_2$F$_5$)$_2$OH, —C(CF$_3$)(CH$_3$)OH, and —CH(CF$_3$)OH, with —C(CF$_3$)$_2$OH being preferable.

The partial structure having a fluorine atom may be bonded directly to the main chain or may be bonded to the main chain through a group selected from the group consisting of an alkylene group, a phenylene group, an ether bond, a thioether bond, a carbonyl group, an ester bond, an amide bond, a urethane bond, and a ureylene bond, or a group formed by combination of two or more thereof.

The hydrophobic resin may contain a silicon atom. The resin preferably has, as the partial structure having a silicon atom, an alkylsilyl structure (preferably a trialkylsilyl group) or a cyclic siloxane structure.

Examples of the alkylsilyl structure or the cyclic siloxane structure include the partial structures described in paragraphs [0304] to [0307] of JP2013-178370A.

Examples of the repeating unit having a fluorine atom or a silicon atom include those exemplified in [0519] of US2012/0251948A1.

Furthermore, it is also preferable that the hydrophobic resin contains a CH$_3$ partial structure in the side chain portion as described above.

Here, the CH$_3$ partial structure (hereinafter also simply referred to as a "side chain CH$_3$ partial structure") contained in the side chain portion in the hydrophobic resin includes a CH$_3$ partial structure contained in an ethyl group, a propyl group, and the like.

On the other hand, a methyl group bonded directly to the main chain of the hydrophobic resin (for example, an α-methyl group in the repeating unit having a methacrylic acid structure) makes only a small contribution of uneven distribution to the surface of the hydrophobic resin due to the effect of the main chain, and it is therefore not included in the CH$_3$ partial structure in the present invention.

More specifically, in the case where the hydrophobic resin contains a repeating unit derived from a monomer having a polymerizable moiety with a carbon-carbon double bond, such as a repeating unit represented by the following General Formula (M), and in addition, R$_{11}$ to R$_{14}$ are CH$_3$ "themselves", such CH$_3$ is not included in the CH$_3$ partial structure contained in the side chain portion in the present invention.

On the other hand, a CH$_3$ partial structure which is present via a certain atom from a C—C main chain corresponds to the CH$_3$ partial structure in the present invention. For example, in the case where R$_{11}$ is an ethyl group (CH$_2$CH$_3$), the hydrophobic resin has "one" CH$_3$ partial structure in the present invention.

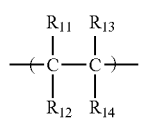

(M)

In General Formula (M),

R$_{11}$ to R$_{14}$ each independently represent a side chain portion.

Examples of R$_{11}$ to R$_{14}$ at the side chain portion include a hydrogen atom and a monovalent organic group.

Examples of the monovalent organic group for R$_{11}$ to R$_{14}$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group, each of which may further have a substituent.

The hydrophobic resin is preferably a resin including a repeating unit having the CH$_3$ partial structure in the side chain portion thereof. Further, the hydrophobic resin preferably has, as such a repeating unit, at least one repeating unit (x) selected from a repeating unit represented by the following General Formula (II) and a repeating unit represented by the following General Formula (III).

Hereinafter, the repeating unit represented by General Formula (II) will be described in detail.

(II)

In General Formula (II), X$_{b1}$ represents a hydrogen atom, an alkyl group, a cyano group, or a halogen atom, and R$_2$ represents an organic group which has one or more CH$_3$ partial structures and is stable against an acid. Here, more specifically, the organic group which is stable against an acid is preferably an organic group which does not have an "acid-decomposable group" described with respect to the resin (A).

The alkyl group of X$_{b1}$ is preferably an alkyl group having 1 to 4 carbon atoms, and examples thereof include a methyl group, an ethyl group, a propyl group, a hydroxymethyl group, and a trifluoromethyl group, with the methyl group being preferable.

X$_{b1}$ is preferably a hydrogen atom or a methyl group.

Examples of R$_2$ include an alkyl group, a cycloalkyl group, an alkenyl group, a cycloalkenyl group, an aryl group, and an aralkyl group, each of which has one or more CH$_3$ partial structures. Each of the cycloalkyl group, the alkenyl group, the cycloalkenyl group, the aryl group and the aralkyl group may further have an alkyl group as a substituent.

R$_2$ is preferably an alkyl group or an alkyl-substituted cycloalkyl group, each of which has one or more CH$_3$ partial structures.

The number of the CH$_3$ partial structures contained in the organic group which has one or more CH$_3$ partial structures and is stable against an acid as R$_2$ is preferably 2 to 10, and more preferably 2 to 8.

Specific preferred examples of the repeating unit represented by General Formula (II) are shown below, but the present invention is not limited thereto.

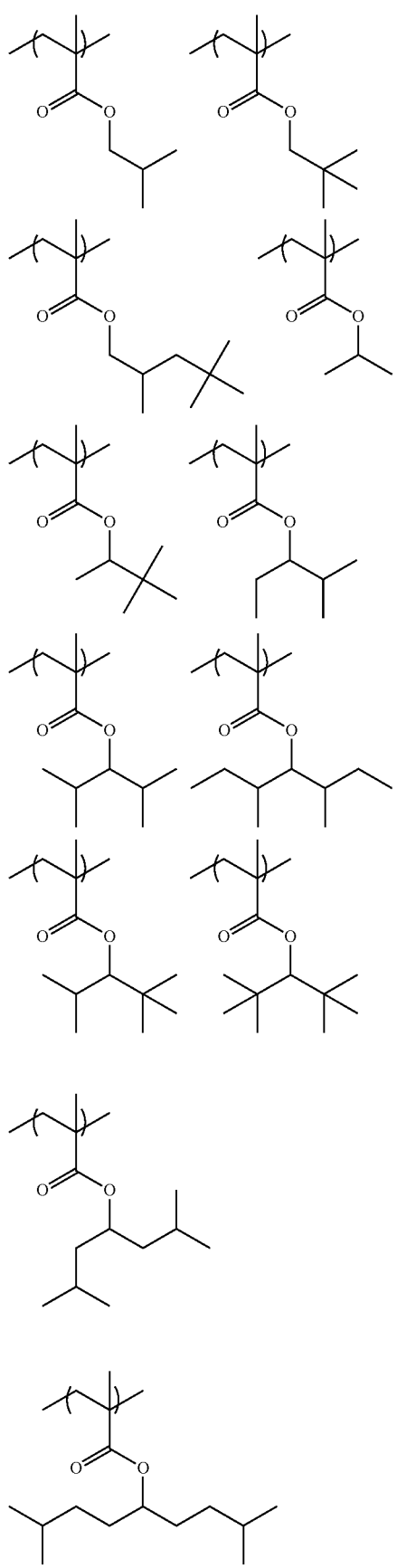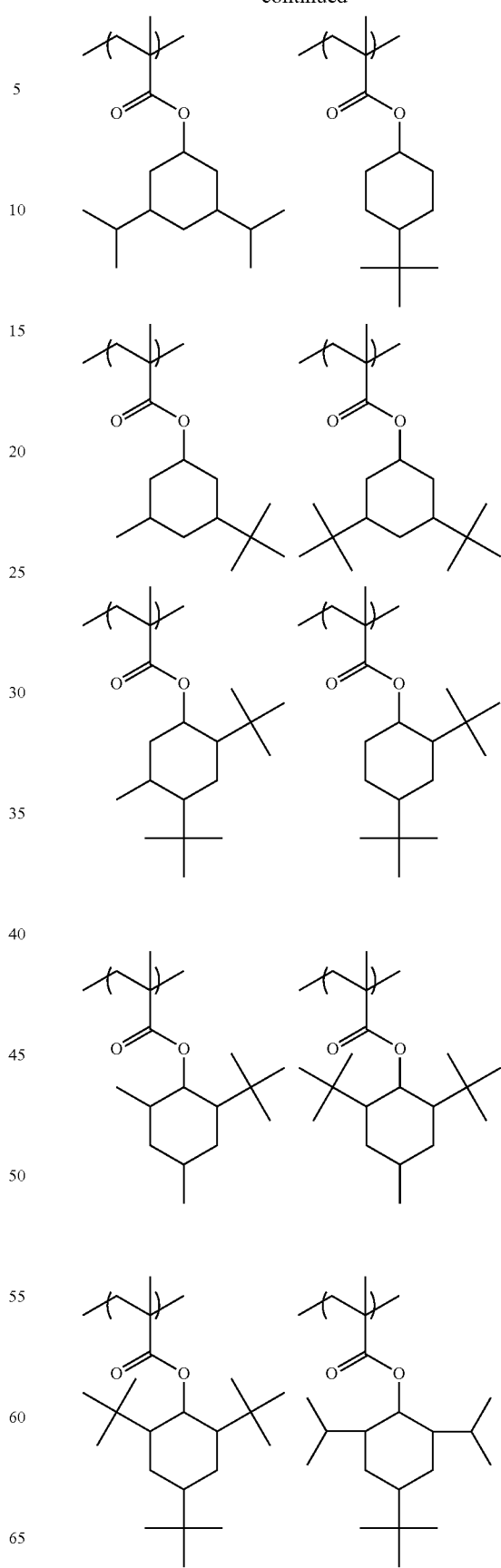

-continued

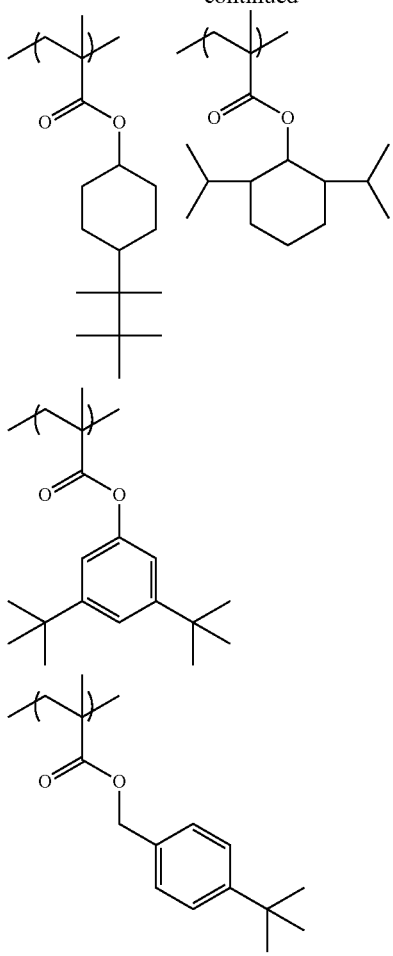

The repeating unit represented by General Formula (II) is preferably a repeating unit which is stable against an acid (acid-indecomposable), and specifically, it is preferably a repeating unit not having a group capable of decomposing by the action of an acid to generate a polar group.

Hereinafter, the repeating unit represented by General Formula (III) will be described in detail.

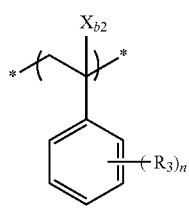

(III)

In General Formula (III), $X_{b2}$ represents a hydrogen atom, an alkyl group, a cyano group, or a halogen atom, $R_3$ represents an organic group which has one or more $CH_3$ partial structures and is stable against an acid, and n represents an integer of 1 to 5.

The alkyl group of $X_{b2}$ is preferably an alkyl group having 1 to 4 carbon atoms, and examples thereof include a methyl group, an ethyl group, a propyl group, a hydroxymethyl group, and a trifluoromethyl group, but a hydrogen atom is preferable.

$X_{b2}$ is preferably a hydrogen atom.

Since $R_3$ is an organic group stable against an acid, more specifically, $R_3$ is preferably an organic group which does not have the "acid-decomposable group" described with respect to the resin (A).

Examples of $R_3$ include an alkyl group having one or more $CH_3$ partial structures.

The number of the $CH_3$ partial structures contained in the organic group which has one or more $CH_3$ partial structures and is stable against an acid as $R_3$ is preferably 1 to 10, more preferably 1 to 8, and still more preferably 1 to 4.

n represents an integer of 1 to 5, preferably 1 to 3, and more preferably 1 or 2.

Specific preferred examples of the repeating unit represented by General Formula (III) are shown below, but the present invention is not limited thereto.

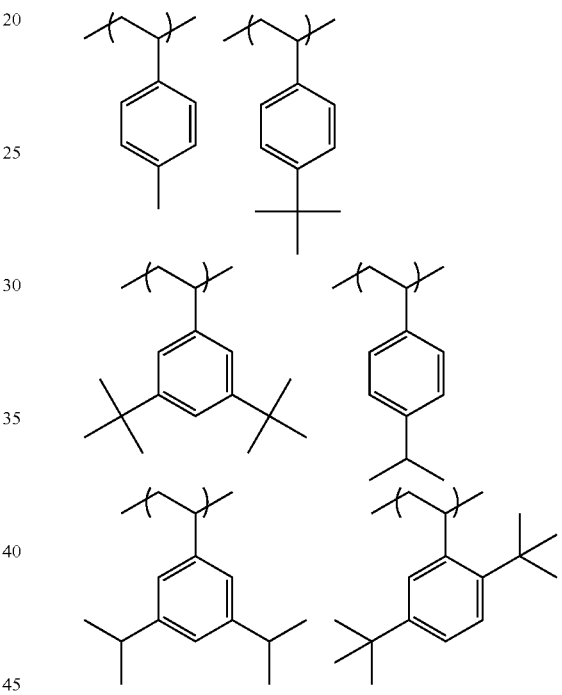

The repeating unit represented by General Formula (III) is preferably a repeating unit which is stable against an acid (acid-indecomposable), and specifically, it is a repeating unit which does not has a group capable of decomposing by the action of an acid to generate a polar group.

In the case where the hydrophobic resin contains a $CH_3$ partial structure in the side chain portion thereof, and in particular, it has neither a fluorine atom nor a silicon atom, the content of at least one repeating unit (x) of the repeating unit represented by General Formula (II) or the repeating unit represented by General Formula (III) is preferably 90% by mole or more, and more preferably 95% by mole or more, with respect to all the repeating units of the hydrophobic resin. Further, the content is usually 100% by mole or less with respect to all the repeating units of the hydrophobic resin.

By incorporating at least one repeating unit (x) of the repeating unit represented by General Formula (II) or the repeating unit represented by General Formula (III) in a proportion of 90% by mole or more with respect to all the repeating units of the hydrophobic resin into the hydrophobic resin, the surface free energy of the hydrophobic resin is increased. As a result, it is difficult for the hydrophobic resin to be unevenly distributed on the surface of the resist film and the static/dynamic contact angle of the resist film with respect to water can be securely increased, thereby enhancing the immersion liquid tracking properties.

In addition, in the case where the hydrophobic resin contains (i) a fluorine atom and/or a silicon atom or (ii) a $CH_3$ partial structure in the side chain moiety, the hydrophobic resin may have at least one group selected from the following groups (x) to (z):

(x) an acid group, (y) a group having a lactone structure, an acid anhydride group, or an acid imido group, and (z) a group capable of decomposing by the action of an acid.

Examples of the acid group (x) include a phenolic hydroxyl group, a carboxylic acid group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group.

Preferred examples of the acid group include a fluorinated alcohol group (preferably a hexafluoroisopropanol group), a sulfonimido group, and a bis(alkylcarbonyl)methylene group.

Examples of the repeating unit containing an acid group (x) include a repeating unit in which the acid group is directly bonded to the main chain of the resin, such as a repeating unit by an acrylic acid or a methacrylic acid, and a repeating unit in which the acid group is bonded to the main chain of the resin through a linking group, and the acid group may also be introduced into the polymer chain terminal by using a polymerization initiator or chain transfer agent containing an acid group during the polymerization. All of these cases are preferable. The repeating unit having an acid group (x) may have at least one of a fluorine atom or a silicon atom.

The content of the repeating units containing an acid group (x) is preferably 1% to 50% by mole, more preferably 3% to 35% by mole, and still more preferably 5% to 20% by mole, with respect to all the repeating units in the hydrophobic resin.

Specific preferred examples of the repeating unit containing an acid group (x) are shown below, but the present invention is not limited thereto. In the formulae, Rx represents a hydrogen atom, $CH_3$, $CF_3$, or $CH_2OH$.

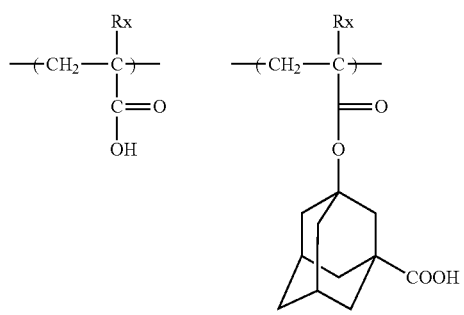

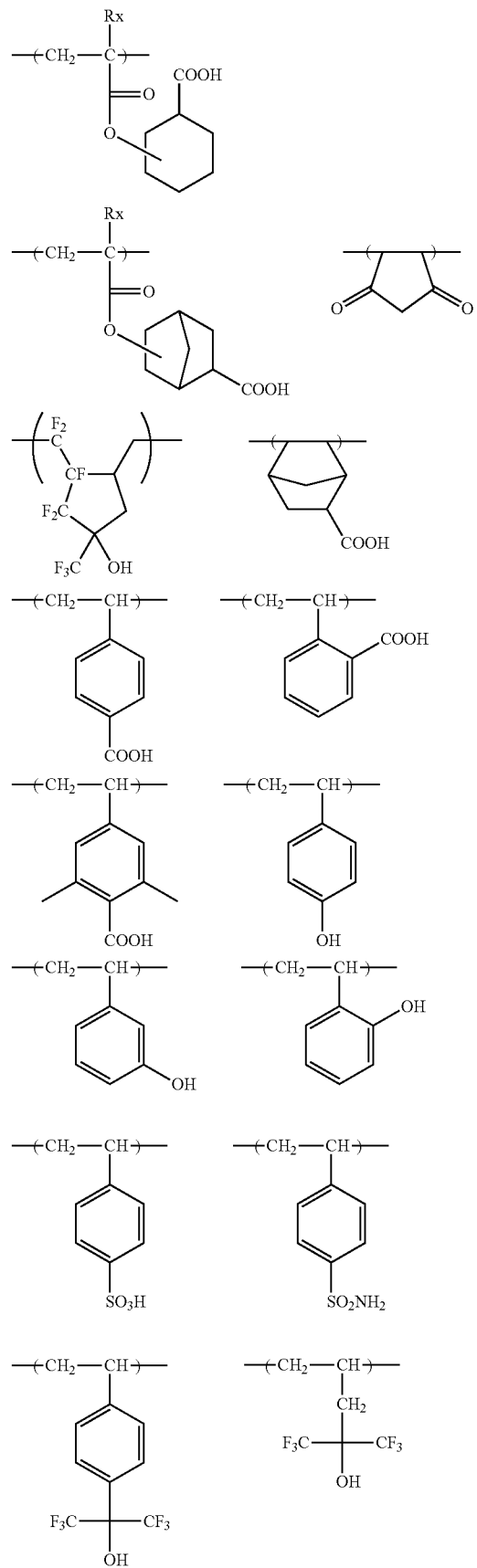

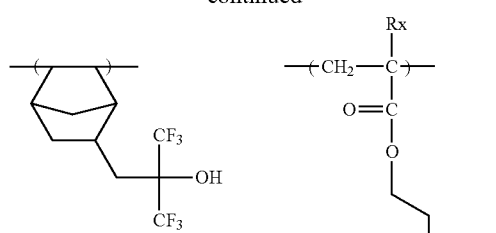
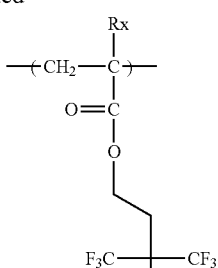
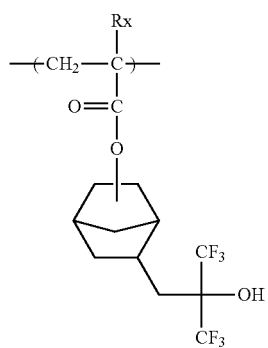
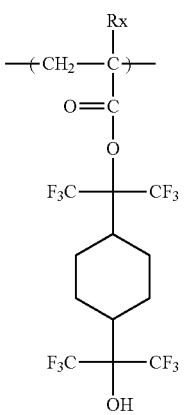
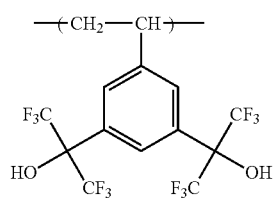
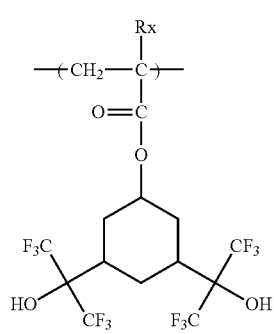
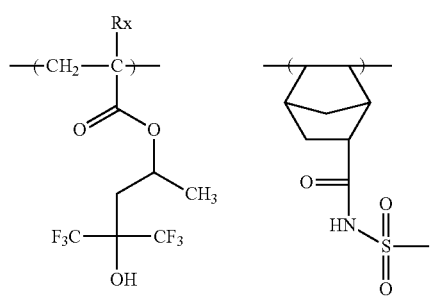

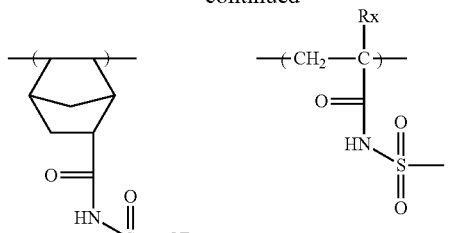
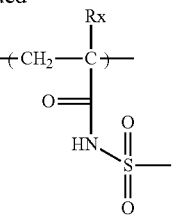
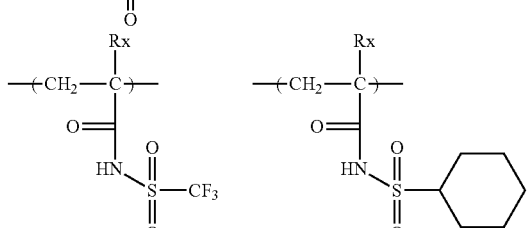
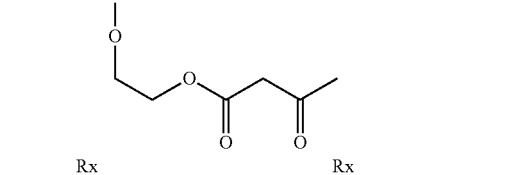
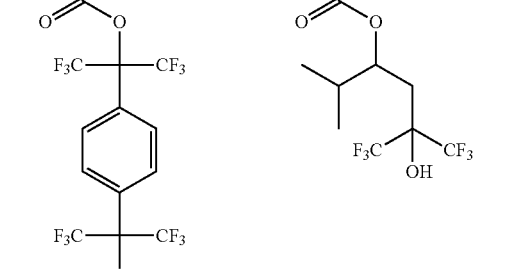
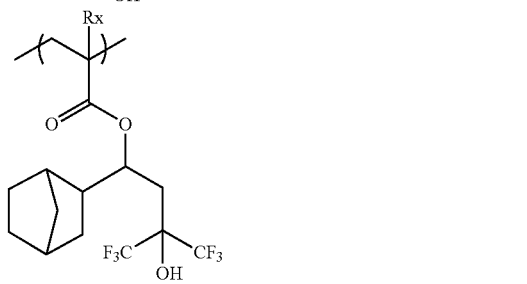

As the group having a lactone structure, the acid anhydride group, or the acid imido group (y), a group having a lactone structure is particularly preferable.

The repeating unit containing such a group is, for example, a repeating unit in which the group is directly bonded to the main chain of the resin, such as a repeating unit by an acrylic ester or a methacrylic ester. This repeating unit may be a repeating unit in which the group is bonded to the main chain of the resin through a linking group. Alternatively this repeating unit may be introduced into the terminal of the resin by using a polymerization initiator or chain transfer agent containing the group during the polymerization.

Examples of the repeating unit containing a group having a lactone structure include the same ones as the repeating unit having a lactone structure as described earlier in the section of the resin (A).

The content of the repeating units having a group having a lactone structure, an acid anhydride group, or an acid imido group is preferably 1% to 100% by mole, more preferably 3% to 98% by mole, and still more preferably 5% to 95% by mole, with respect to all the repeating units in the hydrophobic resin.

With respect to the hydrophobic resin, examples of the repeating unit having a group (z) capable of decomposing by the action of an acid include the same ones as the repeating units having an acid-decomposable group, as mentioned with respect to the resin (A). The repeating unit having a group (z) capable of decomposing by the action of an acid may have at least one of a fluorine atom or a silicon atom. With respect to the hydrophobic resin, the content of the repeating units having a group (z) capable of decomposing by the action of an acid is preferably 1% to 80% by mole, more preferably 10% to 80% by mole, and still more preferably 20% to 60% by mole, with respect to all the repeating units in the hydrophobic resin.

The hydrophobic resin may further have a repeating unit represented by the following General Formula (III).

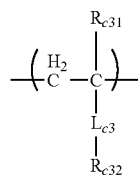

(III)

In General Formula $R_{c31}$ represents a hydrogen atom, an alkyl group (which may be substituted with a fluorine atom or the like), a cyano group, or a —CH$_2$—O—$R_{ac2}$ group, in which $Rac_2$ represents a hydrogen atom, an alkyl group, or an acyl group, and $R_{c31}$ is preferably a hydrogen atom, a methyl group, a hydroxymethyl group, or a trifluoromethyl group, and particularly preferably a hydrogen atom or a methyl group.

$R_{c32}$ represents a group having an alkyl group, a cycloalkyl group, an alkenyl group, a cycloalkenyl group, or an aryl group, each of which may be substituted with a group containing a fluorine atom or a silicon atom.

$L_{c3}$ represents a single bond or a divalent linking group.

In General Formula (III), the alkyl group of $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably an aryl group having 6 to 20 carbon atoms, and more preferably a phenyl group or a naphthyl group, and these groups may have a substituent.

$R_{c32}$ is preferably an unsubstituted alkyl group or an alkyl group substituted with a fluorine atom.

The divalent linking group of $L_{c3}$ is preferably an alkylene group (preferably having 1 to 5 carbon atoms), an ether bond, a phenylene group, or an ester bond (a group represented by —COO—).

The content of the repeating units represented by formula (III) is preferably 1% to 100% by mole, more preferably 10% to 90% by mole, and still more preferably 30% to 70% by mole, with respect to all the repeating units in the hydrophobic resin.

It is also preferable that the hydrophobic resin further has a repeating unit represented by the following General Formula (CII-AB).

(CII-AB)

In Formula (CII-AB), $R_{c11}'$ and $R_{c12}'$ each independently represent a hydrogen atom, a cyano group, a halogen atom, or an alkyl group.

$Z_c'$ represents an atomic group for forming an alicyclic structure containing two carbon atoms (C—C) to which $Z_c'$ is bonded.

The content of the repeating units represented by General Formula (CII-AB) is preferably 1% to 100% by mole, more preferably 10% to 90% by mole, and still more preferably 30% to 70% by mole, with respect to all the repeating units in the hydrophobic resin.

Specific examples of the repeating units represented by General Formulae (III) and (CII-AB) are shown below, but the present invention is not limited thereto. In the formulae, Ra represents H, CH$_3$, CH$_2$OH, CF$_3$, or CN.

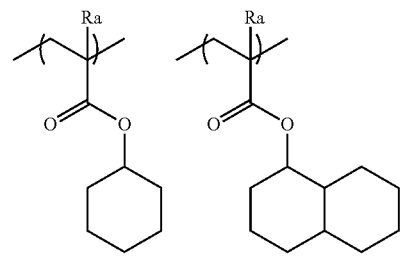

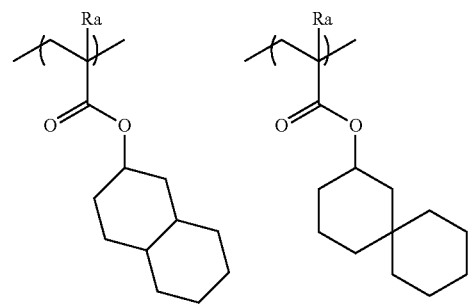

-continued

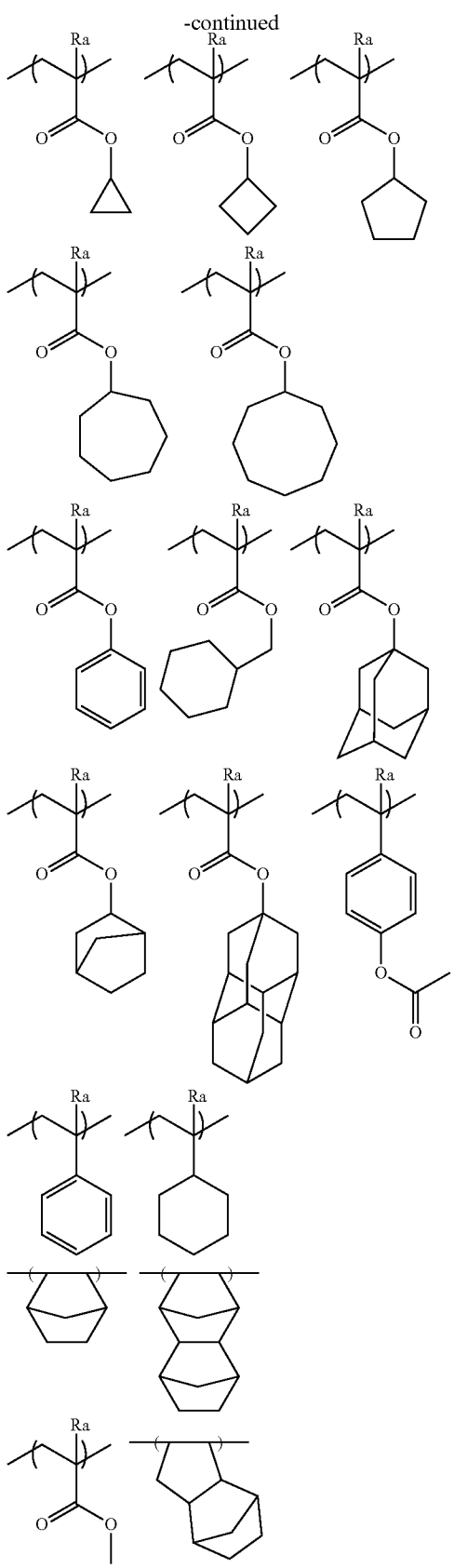

In the case where the hydrophobic resin has a fluorine atom, the content of the fluorine atom is preferably 5% to 80% by mass, and more preferably 10% to 80% by mass, with respect to the weight-average molecular weight of the hydrophobic resin. Further, the proportion of the repeating units containing a fluorine atom is preferably 10% to 100% by mole, and more preferably 30% to 100% by mole, with respect to all the repeating units included in the hydrophobic resin.

In the case where the hydrophobic resin has a silicon atom, the content of the silicon atom is preferably 2% to 50% by mass, and more preferably 2% to 30% by mass, with respect to the weight-average molecular weight of the hydrophobic resin. Further, the proportion of the repeating unit containing a silicon atom is preferably 10% to 100% by mole, and more preferably 20% to 100% by mole, with respect to all the repeating units included in the hydrophobic resin.

On the other hand, in particular, in the case where the hydrophobic resin contains a $CH_3$ partial structure in the side chain portion thereof, it is also preferable that the hydrophobic resin has a form having substantially neither a fluorine atom nor a silicon atom. In this case, specifically the content of the repeating units containing a fluorine atom or a silicon atom is preferably 5% by mole or less, more preferably 3% by mole or less, still more preferably 1% by mole or less, and ideally 0% by mole, that is, containing neither a fluorine atom nor a silicon atom, with respect to all the repeating units in the hydrophobic resin. In addition, it is preferable that the hydrophobic resin is composed substantially of only a repeating unit constituted with only an atom selected from the group consisting of a carbon atom, an oxygen atom, a hydrogen atom, a nitrogen atom, and a sulfur atom. More specifically the proportion of the repeating unit constituted with only an atom selected from the group consisting of a carbon atom, an oxygen atom, a hydrogen atom, a nitrogen atom, and a sulfur atom is preferably 95% by mole or more, more preferably 97% by mole or more, still more preferably 99% by mole or more, and ideally 100% by mole, of all the repeating units in the hydrophobic resin.

The weight-average molecular weight of the hydrophobic resin in terms of standard polystyrene is preferably 1,000 to 100,000, more preferably 1,000 to 50,000, and still more preferably 2,000 to 15,000.

Furthermore, the hydrophobic resins may be used alone or in combination of plural kinds thereof.

The content of the hydrophobic resins in the composition is preferably 0.01% to 10% by mass, more preferably 0.05% to 8% by mass, and still more preferably 0.1% to 7% by mass, with respect to the total solid content of the composition of the present invention.

In the hydrophobic resin, it is certain that the content of impurities such as metal is small, but the content of residual monomers or oligomer components is also preferably 0.01% to 5% by mass, more preferably 0.01% to 3% by mass, and still more preferably 0.05% to 1% by mass. Within these ranges, a composition free from in-liquid extraneous materials and a change in sensitivity or the like with aging can be obtained. Further, from the viewpoints of a resolution, a resist profile, the side wall of a resist pattern, a roughness, and the like, the molecular weight distribution (Mw/Mn, also referred to as a dispersity) is preferably in the range of 1 to 5, more preferably in the range of 1 to 3, and still more preferably in the range of 1 to 2.

As the hydrophobic resin, various commercial products may be used, or the resin may be synthesized by an ordinary method (for example, radical polymerization). Examples of the general synthesis method include a batch polymerization method of dissolving monomer species and an initiator in a solvent and heating the solution, thereby carrying out the polymerization, and a dropping polymerization method of adding dropwise a solution containing monomer species and an initiator to a heated solvent for 1 to 10 hours, with the dropping polymerization method being preferable.

The reaction solvent, the polymerization initiator, the reaction conditions (a temperature, a concentration, and the like) and the method for purification after reaction are the same as ones described for the resin (A), but in the synthesis of the hydrophobic resin the concentration of the reactant is preferably 30% to 50% by mass.

Specific examples of the hydrophobic resin are shown below. Further, the molar ratio of the repeating units (corresponding to the respective repeating units in order from the left side), the weight-average molecular weight, and the dispersity with respect to the respective resins are shown in Tables below.

(B-1)
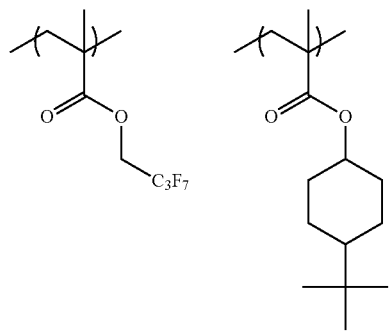

(B-2)
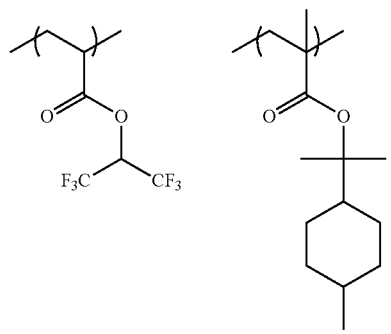

(B-3)
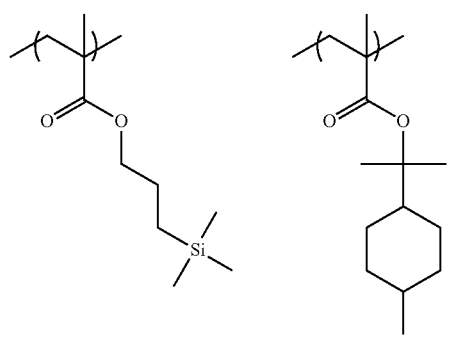

(B-4)
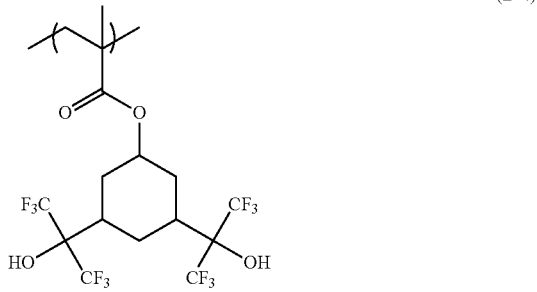

(B-5)
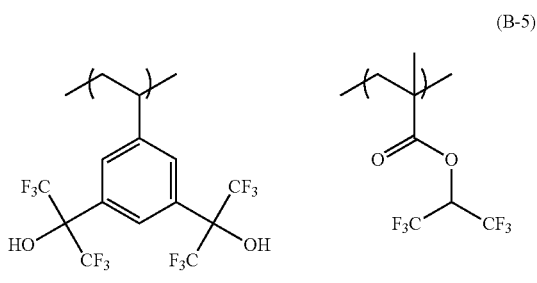

(B-6)
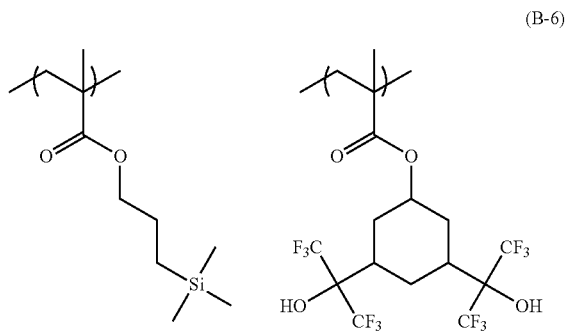
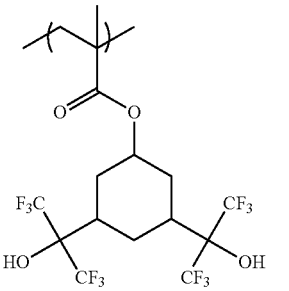

(B-7)

(B-8)
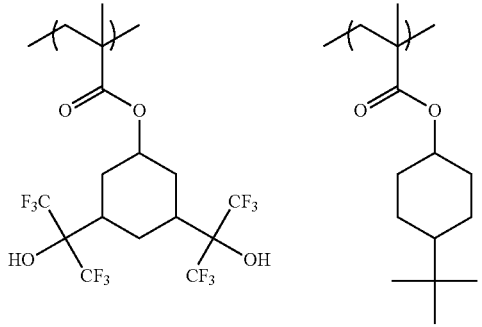

(B-9)
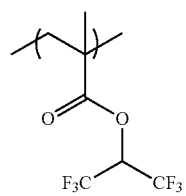 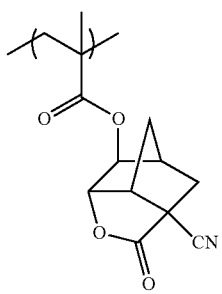
(B-10)
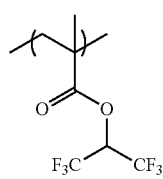 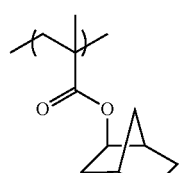 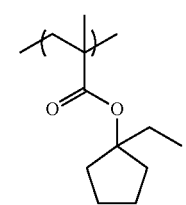
(B-11)
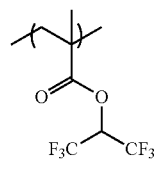 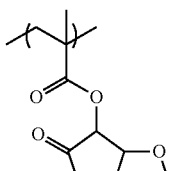 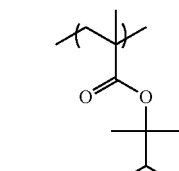
(B-12)
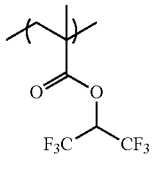 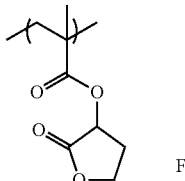 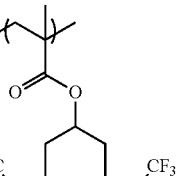
(B-13)
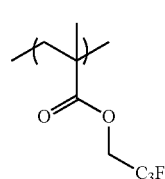 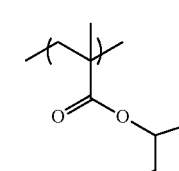
(B-14)
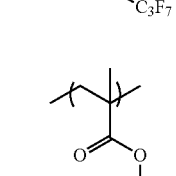 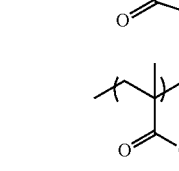
(B-15)
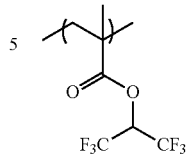 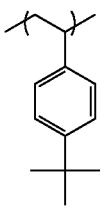 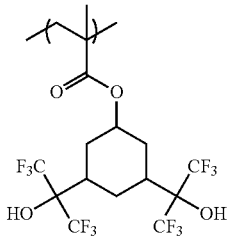
(B-16)
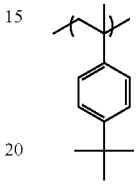 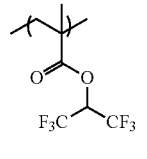 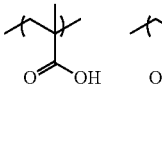 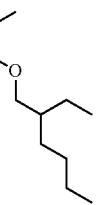
(B-17)
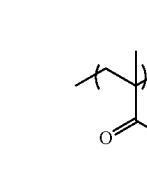 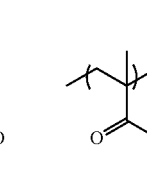 
(B-18)
 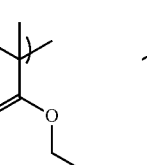 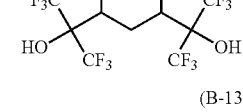
(B-19)
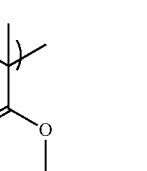 

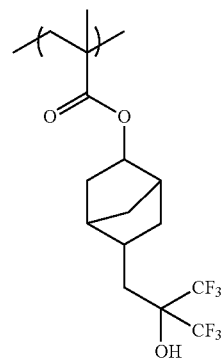 (B-20)
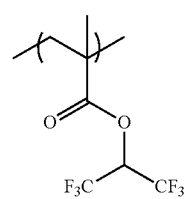 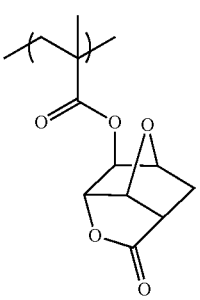 (B-21)
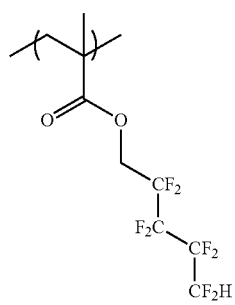 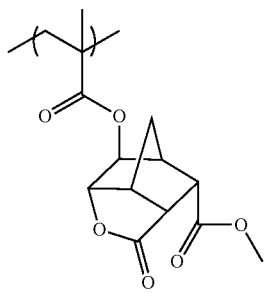 (B-22)
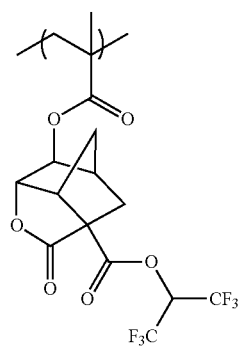 (B-23)
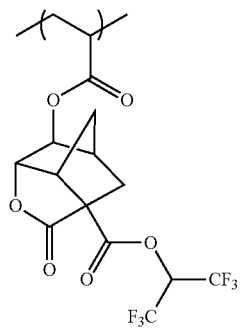 (B-24)
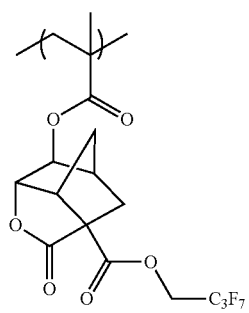 (B-25)
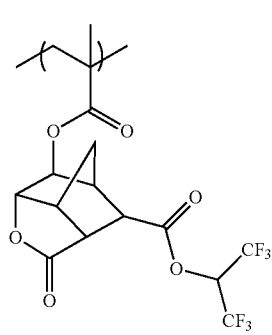 (B-26)
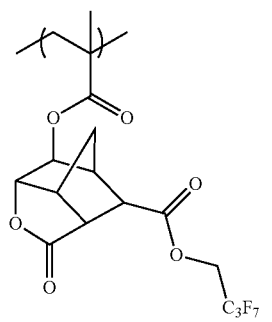 (B-27)
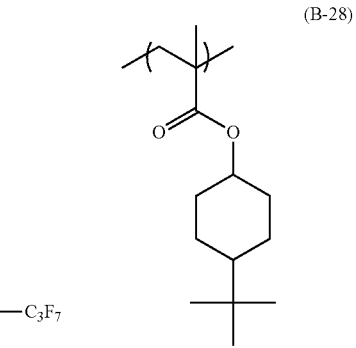 (B-28)

(B-29)
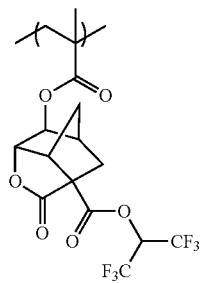 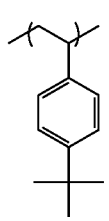 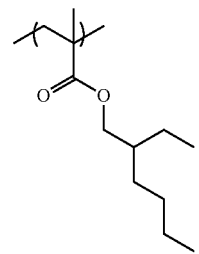
(B-30)
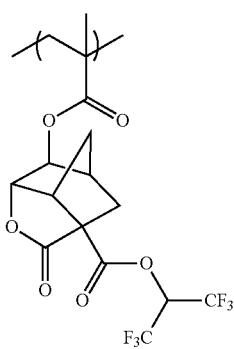 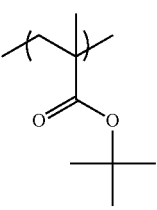
(B-31)
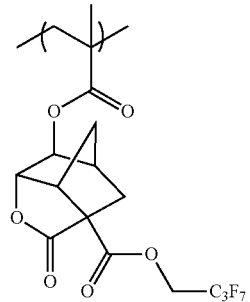 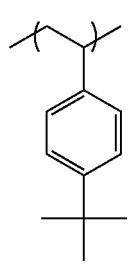
(B-32)
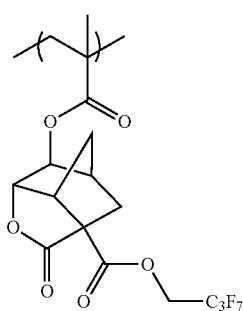 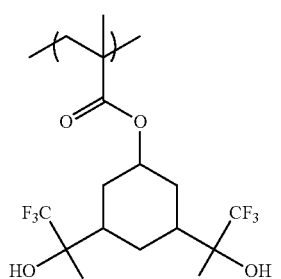
(B-33)
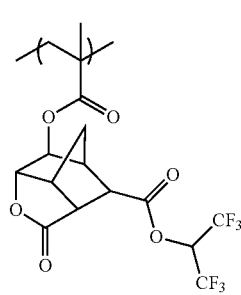 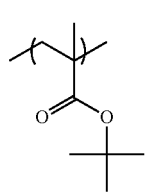 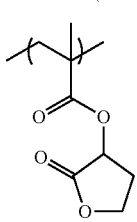
(B-34)
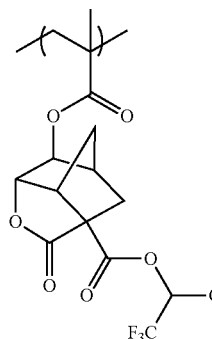 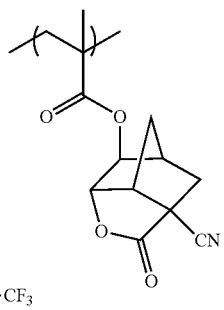
(B-35)
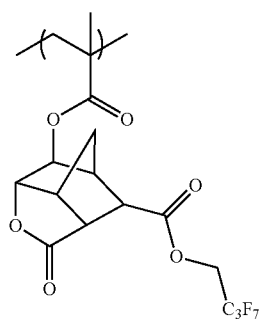 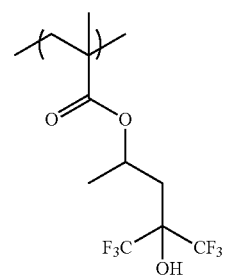
(B-36)
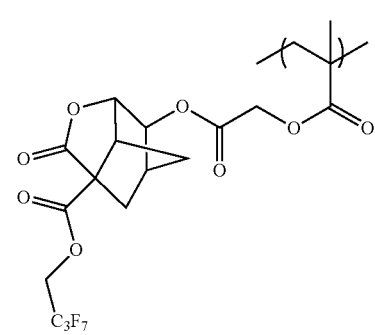
(B-37)
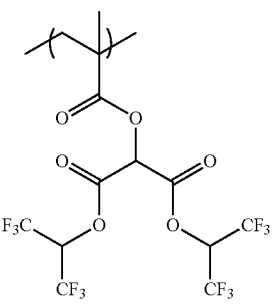 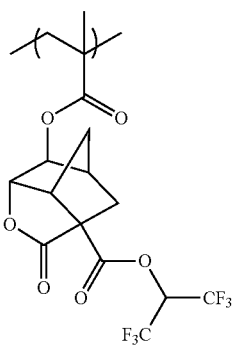

(B-38)
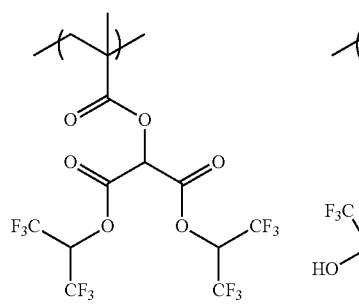
(B-39)
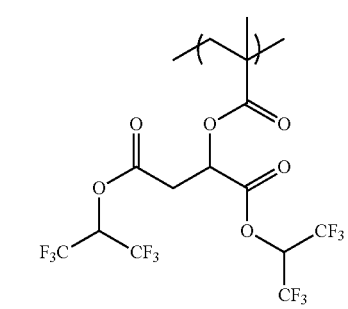
(B-40)
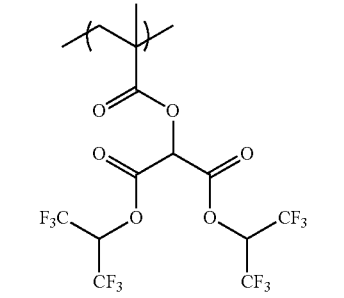
(B-41)
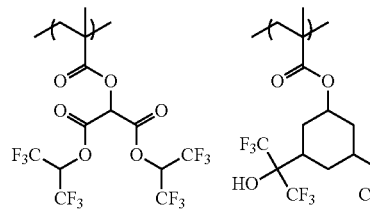
(B-42)
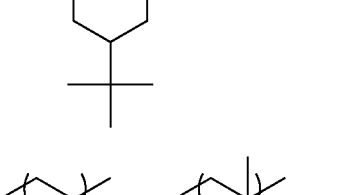
TABLE 1
| Resin | Compositional ratio | Molecular weight | Dispersity |
|---|---|---|---|
| B-1 | 50/50 | 4,800 | 1.4 |
| B-2 | 50/50 | 5,100 | 2.1 |
| B-3 | 40/60 | 6,600 | 1.8 |
| B-4 | 100 | 5,500 | 1.7 |
| B-5 | 45/55 | 4,400 | 1.6 |
| B-6 | 50/50 | 6,000 | 1.5 |
| B-7 | 40/10/50 | 6,200 | 1.6 |
| B-8 | 50/50 | 5,800 | 1.5 |
| B-9 | 80/20 | 4,800 | 1.8 |
| B-10 | 50/20/30 | 4,900 | 1.9 |
| B-11 | 50/10/40 | 5,300 | 2.0 |
| B-12 | 40/20/40 | 5,500 | 1.4 |
| B-13 | 60/40 | 5,900 | 1.3 |
| B-14 | 50/50 | 6,200 | 1.5 |
| B-15 | 40/15/45 | 6,100 | 1.8 |
| B-16 | 57/39/2/2 | 6,000 | 1.6 |
| B-17 | 45/20/35 | 6,600 | 1.6 |
| B-18 | 40/30/30 | 5,500 | 1.7 |
| B-19 | 100 | 4,900 | 1.6 |
| B-20 | 100 | 4,400 | 1.8 |
| B-21 | 60/40 | 4,500 | 1.9 |
| B-22 | 55/45 | 6,200 | 1.3 |
| B-23 | 100 | 5,700 | 1.5 |
| B-24 | 100 | 5,800 | 2.0 |
| B-25 | 100 | 6,000 | 1.5 |
| B-26 | 100 | 6,000 | 1.6 |
| B-27 | 100 | 6,200 | 1.8 |
| B-28 | 50/50 | 6,500 | 1.7 |
| B-29 | 90/8/2 | 6,500 | 1.5 |
| B-30 | 90/10 | 6,900 | 1.7 |
| B-31 | 95/5 | 4,900 | 1.8 |
| B-32 | 80/20 | 5,200 | 1.9 |
| B-33 | 75/15/10 | 5,900 | 1.6 |
| B-34 | 75/25 | 6,000 | 1.5 |
| B-35 | 80/20 | 5,700 | 1.4 |
| B-36 | 100 | 5,300 | 1.7 |
| B-37 | 20/80 | 5,400 | 1.6 |
| B-38 | 50/50 | 4,800 | 1.6 |
| B-39 | 70/30 | 4,500 | 1.6 |
| B-40 | 100 | 5,500 | 1.5 |
| B-41 | 40/40/20 | 5,800 | 1.5 |
| B-42 | 35/35/30 | 6,200 | 1.4 |
(C-1)
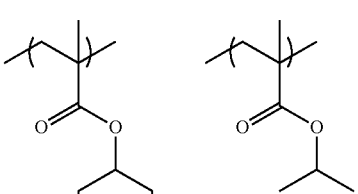
(C-2)
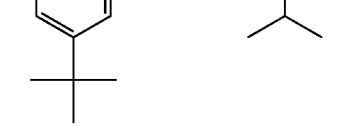

(C-3) 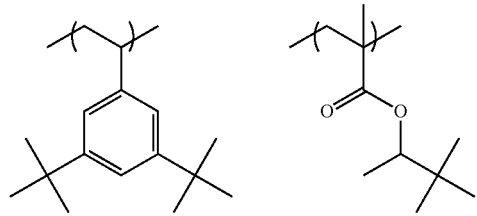
(C-4) 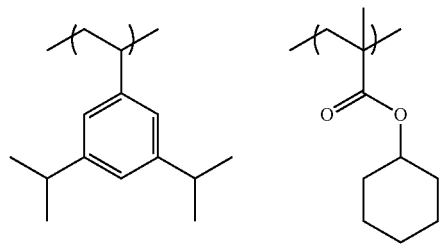
(C-5) 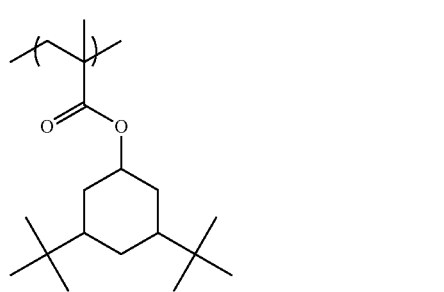
(C-6) 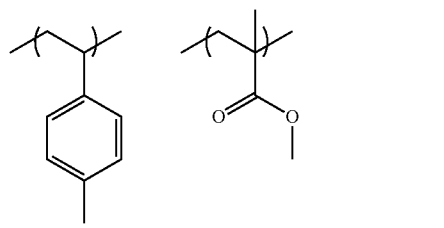
(C-7) 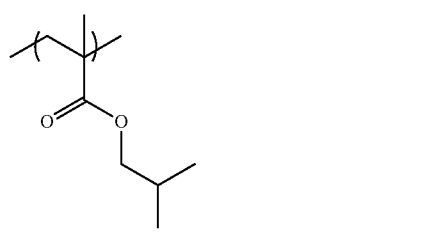
(C-8) 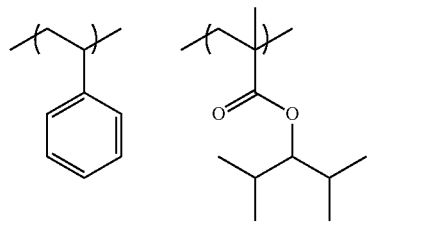
(C-9) 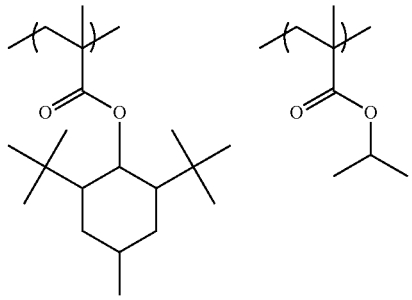
(C-10) 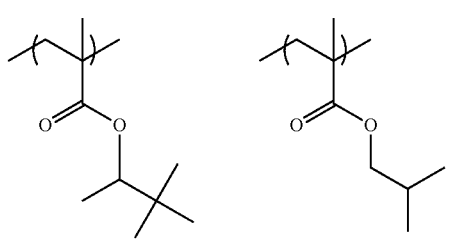
(C-11) 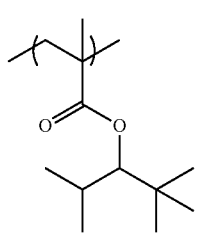
(C-12) 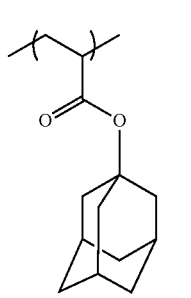
(C-13) 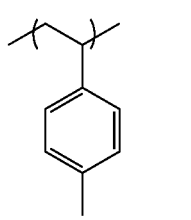
(C-14) 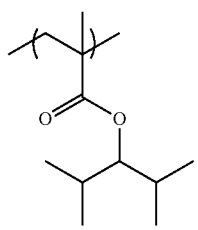

(C-15) 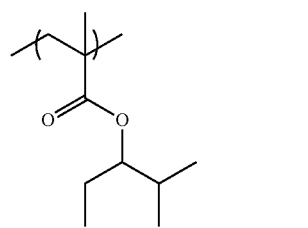
(C-16) 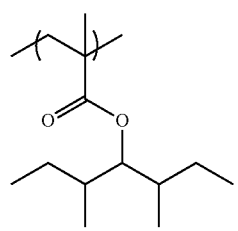
(C-17) 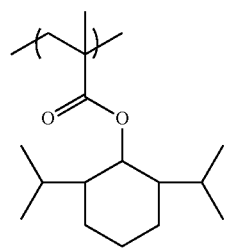
(C-18) 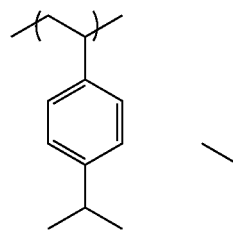
(C-19) 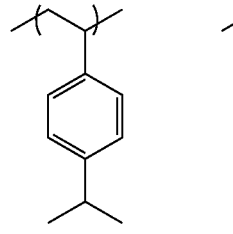
(C-20) 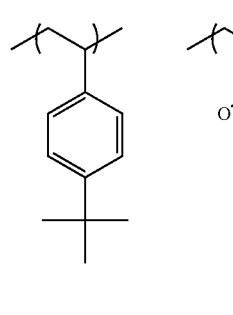
(C-21) 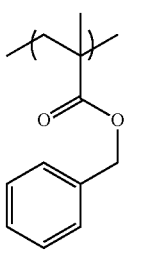 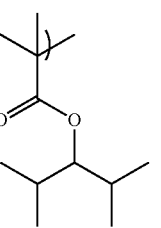
(C-22) 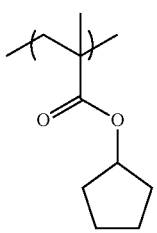 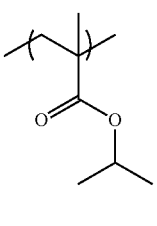
(C-23) 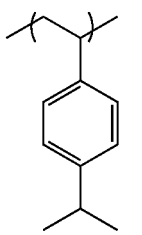 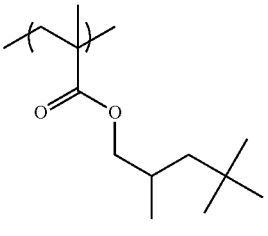
(C-24) 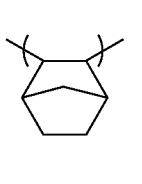 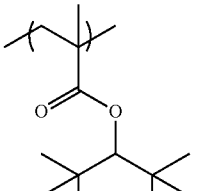
(C-25) 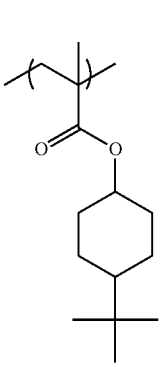 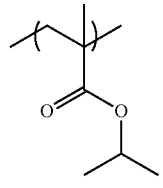 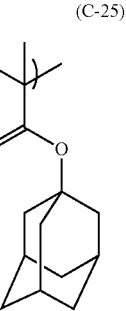
(C-26) 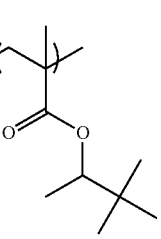 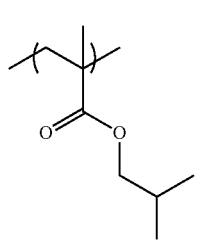 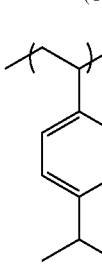

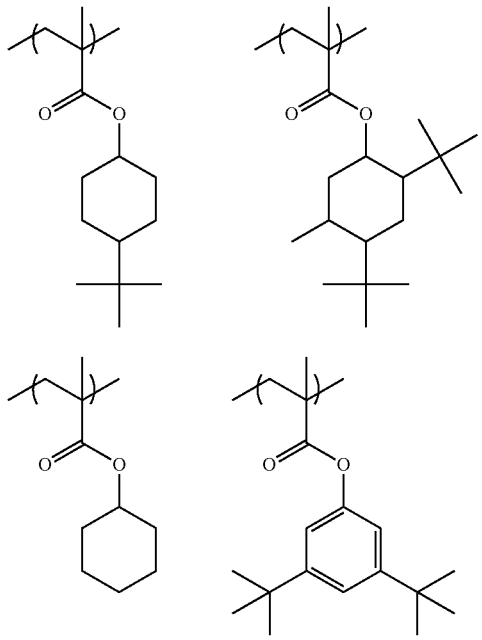

(C-27)

(C-28)

TABLE 2

| Resin | Composition | Mw | Mw/Mn |
|---|---|---|---|
| C-1 | 50/50 | 9,600 | 1.74 |
| C-2 | 60/40 | 34,500 | 1.43 |
| C-3 | 30/70 | 19,300 | 1.69 |
| C-4 | 90/10 | 26,400 | 1.41 |
| C-5 | 100 | 27,600 | 1.87 |
| C-6 | 80/20 | 4,400 | 1.96 |
| C-7 | 100 | 16,300 | 1.83 |
| C-8 | 5/95 | 24,500 | 1.79 |
| C-9 | 20/80 | 15,400 | 1.68 |
| C-10 | 50/50 | 23,800 | 1.46 |
| C-11 | 100 | 22,400 | 1.57 |
| C-12 | 10/90 | 21,600 | 1.52 |
| C-13 | 100 | 28,400 | 1.58 |
| C-14 | 50/50 | 16,700 | 1.82 |
| C-15 | 100 | 23,400 | 1.73 |
| C-16 | 60/40 | 18,600 | 1.44 |
| C-17 | 80/20 | 12,300 | 1.78 |
| C-18 | 40/60 | 18,400 | 1.58 |
| C-19 | 70/30 | 12,400 | 1.49 |
| C-20 | 50/50 | 23,500 | 1.94 |
| C-21 | 10/90 | 7,600 | 1.75 |
| C-22 | 5/95 | 14,100 | 1.39 |
| C-23 | 50/50 | 17,900 | 1.61 |
| C-24 | 10/90 | 24,600 | 1.72 |
| C-25 | 50/40/10 | 23,500 | 1.65 |
| C-26 | 60/30/10 | 13,100 | 1.51 |
| C-27 | 50/50 | 21,200 | 1.84 |
| C-28 | 10/90 | 19,500 | 1.66 |

<Acid Diffusion Control Agent (D)>

The composition of the present invention preferably contains an acid diffusion control agent (D). The acid diffusion control agent (D) acts as a quencher that inhibits a reaction of the acid-decomposable resin in the unexposed area by excessive generated acids by trapping the acids generated from an acid generator or the like upon exposure. As the acid diffusion control agent (D), a basic compound having a nitrogen atom, a low-molecular compound having a nitrogen atom and a group capable of leaving by the action of an acid, a basic compound whose basicity is reduced or lost upon irradiation with active light or radiation, or an onium salt which becomes a relatively weak acid with respect to an acid generator can be used.

Preferred examples of the basic compound having a nitrogen atom include compounds having structures represented by the following Formulae (A) to (E).

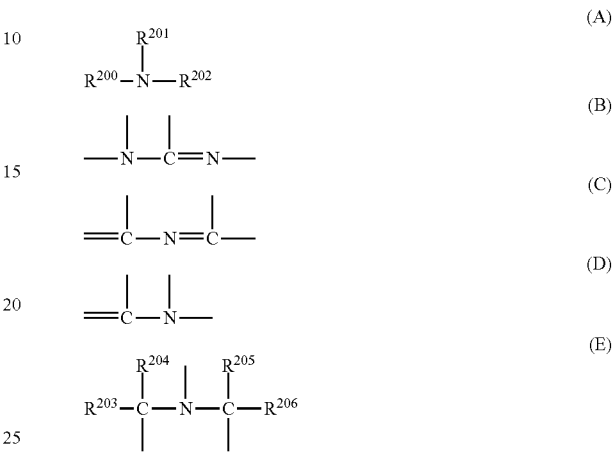

In General Formulae (A) to (E), $R^{200}$, $R^{201}$, and $R^{202}$ may be the same as or different from each other, represent a hydrogen atom, an alkyl group (preferably having 1 to 20 carbon atoms), a cycloalkyl group (preferably having 3 to 20 carbon atoms) or an aryl group (6 to 20 carbon atoms), and $R^{201}$ and $R^{202}$ may be bonded to each other to form a ring.

$R^{203}$, $R^{204}$, $R^{205}$, and $R^{206}$ may be the same as or different from each other, and represent an alkyl group having 1 to 20 carbon atoms.

As for the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl group in General Formulae (A) to (E) is more preferably unsubstituted.

Preferred examples of the compound include guanidine, aminopyrrolidine, pyrazole, pyrazoline, piperazine, aminomorpholine, aminoalkylmorpholine and piperidine. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Specific examples of the preferred compound include the compounds exemplified in [0379] of US2012/0219913A1.

Preferred examples of the basic compounds include a phenoxy group-containing amine compound, a phenoxy group-containing ammonium salt compound, a sulfonic acid ester group-containing amine compound, and a sulfonic acid ester group-containing ammonium salt compound.

As the amine compound, a primary, secondary, or tertiary amine compound can be used, and an amine compound in which at least one alkyl group is bonded to a nitrogen atom is preferable. The amine compound is more preferably a tertiary amine compound. Any amine compound is available as long as at least one alkyl group (preferably having 1 to 20 carbon atoms) is bonded to a nitrogen atom, and a cycloalkyl group (preferably having 3 to 20 carbon atoms) or an aryl group (preferably having 6 to 12 carbon atoms) may be bonded to the nitrogen atom, in addition to the alkyl group. The amine compound preferably has an oxygen atom in the alkyl chain to form an oxyalkylene group. The number of the oxyalkylene groups within the molecule is 1 or more, preferably 3 to 9, and more preferably 4 to 6. Among the oxyalkylene groups, an oxyethylene group (—$CH_2CH_2O$—) or an oxypropylene group (—$CH(CH_3)CH_2O$— or —$CH_2CH_2CH_2O$—) is preferable, and an oxyethylene group is more preferable.

As the ammonium salt compound, a primary, secondary, tertiary, or quaternary ammonium salt compound can be used, and an ammonium salt compound in which at least one alkyl group is bonded to a nitrogen atom is preferable. Any ammonium salt compound is available as long as at least one alkyl group (preferably having 1 to 20 carbon atoms) is bonded to a nitrogen atom, and a cycloalkyl group (preferably having 3 to 20 carbon atoms) or an aryl group (preferably having 6 to 12 carbon atoms) may be bonded to the nitrogen atom, in addition to the alkyl group. The ammonium salt compound preferably has an oxygen atom in the alkyl chain to form an oxyalkylene group. The number of the oxyalkylene groups within the molecule is 1 or more, preferably 3 to 9, and more preferably 4 to 6. Among the oxyalkylene groups, an oxyethylene group (—$CH_2CH_2O$—) or an oxypropylene group (—$CH(CH_3)CH_2O$— or —$CH_2CH_2CH_2O$—) is preferable, and an oxyethylene group is more preferable.

Examples of the anion of the ammonium salt compound include a halogen atom, sulfonate, borate, and phosphate, and among these, the halogen atom and sulfonate are preferable.

Incidentally, the following compounds are also preferable as the basic compound.

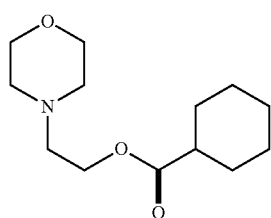
(MO-1)

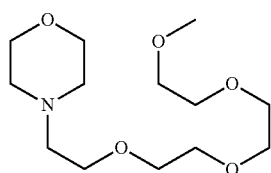
(MO-2)

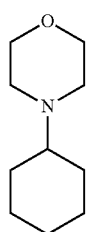
(MO-3)

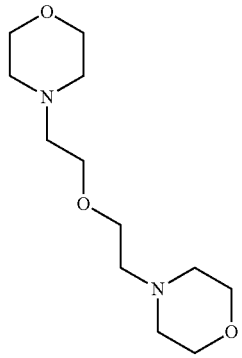
(MO-4)

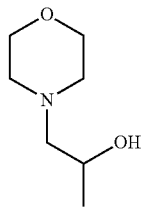
(MO-5)

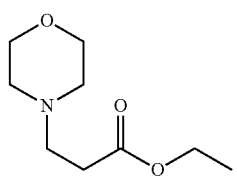
(MO-6)

In addition to the compounds as described above, as the basic compound, the compounds described in [0180] to [0225] of JP2011-22560A, [0218] and [0219] of JP2012-137735A, and [0416] to [0438] of WO2011/158687A1, and the like can also be used.

These basic compounds may be used alone or in combination of two or more kinds thereof.

The composition of the present invention may or may not contain the basic compound, but in the case where it contains the basic compound, the content of the basic compound is usually 0.001% to 10% by mass, and preferably 0.01% to 5% by mass, with respect to the solid content of the composition.

The ratio between the acid generator (including the acid generator (A')) and the basic compound used in the composition is preferably acid generator/basic compound (molar ratio)=2.5 to 300. That is, the molar ratio is preferably 2.5 or more in view of sensitivity and resolution, and is preferably 300 or less in view of suppressing the reduction in resolution due to thickening of the resist pattern with aging after exposure until the heat treatment. The acid generator/basic compound (molar ratio) is more preferably 5.0 to 200, and still more preferably 7.0 to 150.

The low-molecular compound (hereinafter referred to as a "compound (D-1)") which has a nitrogen atom and a group capable of leaving by the action of an acid is preferably an amine derivative having a group capable of leaving by the action of an acid on a nitrogen atom.

As the group capable of leaving by the action of an acid, an acetal group, a carbonate group, a carbamate group, a tertiary ester group, a tertiary hydroxyl group, or a hemiaminal ether group are preferable, and a carbamate group or a hemiaminal ether group is particularly preferable.

The molecular weight of the compound (D-1) is preferably 100 to 1,000, more preferably 100 to 700, and particularly preferably 100 to 500.

The compound (D-1) may contain a carbamate group having a protecting group on a nitrogen atom. The protecting group constituting the carbamate group can be represented by the following General Formula (d-1).

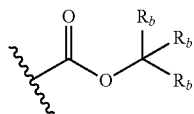

(d-1)

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably having 1 to 10 carbon atoms). $R_b$'s may be linked to each other to form a ring.

The alkyl group, the cycloalkyl group, the aryl group, or the aralkyl group represented by $R_b$ may be substituted with a functional group such as a hydroxyl group, a cyano group, an amino group, a pyrrolidino group, a piperidino group, a morpholino group, and an oxo group, an alkoxy group, or a halogen atom. This shall apply to the alkoxyalkyl group represented by $R_b$.

$R_b$ is preferably a linear or branched alkyl group, a cycloalkyl group, or an aryl group, and more preferably a linear or branched alkyl group, or a cycloalkyl group.

Examples of the ring formed by the mutual linking of two $R_b$'s include an alicyclic hydrocarbon group, an aromatic hydrocarbon group, a heterocyclic hydrocarbon group, and derivatives thereof.

Examples of the specific structure of the group represented by General Formula (d-1) include, but are not limited to, structures disclosed in paragraph [0466] of US2012/0135348A1.

It is particularly preferable that the compound (D-1) has a structure of the following General Formula (6).

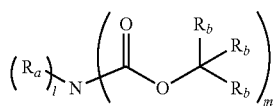

(6)

In General Formula (6), $R_a$ represents a hydrogen atom, an alkyl group, a cycloalkyl group, an aryl group, or an aralkyl group. When l is 2, two $R_a$'s may be the same as or different from each other. Two $R_a$'s may be linked to each other to form a heterocycle together with the nitrogen atom in the formula. The heterocycle may contain a hetero atom other than the nitrogen atom in the formula.

$R_b$ has the same meaning as $R_b$ in General Formula (d-1), and preferred examples are also the same.

l represents an integer of 0 to 2, and m represents an integer of 1 to 3, satisfying l+m=3.

In General Formula (6), the alkyl group, the cycloalkyl group, the aryl group, and the aralkyl group as $R_a$ may be substituted with the same groups as the group mentioned above as a group which may be substituted in the alkyl group, the cycloalkyl group, the aryl group, and the aralkyl group as $R_b$.

Specific examples of the alkyl group, the cycloalkyl group, the aryl group, and the aralkyl group (such the alkyl group, a cycloalkyl group, aryl group, and aralkyl group may be substituted with the groups as described above) of $R_a$ include the same groups as the specific of examples as described above with respect to $R_b$.

Specific examples of the particularly preferred compound (D-1) in the present invention include, but are not limited to, the compounds disclosed in paragraph [0475] of US2012/0135348A1.

The compounds represented by General Formula (6) can be synthesized in accordance with JP2007-298569A, JP2009-199021A, and the like.

In the present invention, the compound (D-1) may be used alone or in combination of two or more kinds thereof.

The content of the compound (D-1) in the composition of the present invention is preferably 0.001% to 20% by mass, more preferably 0.001% to 10% by mass, and still more preferably 0.01% to 5% by mass, with respect to the total solid content of the composition.

The basic compound whose basicity is reduced or lost upon irradiation with active light or radiation (hereinafter also referred to as a "compound (PA)") is a compound which has a functional group with proton acceptor properties, and decomposes under irradiation with active light or radiation to exhibit deterioration in proton acceptor properties, no proton acceptor properties, or a change from the proton acceptor properties to acid properties.

The functional group with proton acceptor properties refers to a functional group having a group or an electron which is capable of electrostatically interacting with a proton, and for example, means a functional group with a macrocyclic structure, such as a cyclic polyether, or a functional group containing a nitrogen atom having an unshared electron pair not contributing to π-conjugation. The nitrogen atom having an unshared electron pair not contributing to π-conjugation is, for example, a nitrogen atom having a partial structure represented by the following formula.

Preferred examples of the partial structure of the functional group with proton acceptor properties include crown ether, azacrown ether, primary to tertiary amines, pyridine, imidazole, and pyrazine structures.

The compound (PA) decomposes upon irradiation with active light or radiation to generate a compound exhibiting deterioration in proton acceptor properties, no proton acceptor properties, or a change from the proton acceptor properties to acid properties. Here, exhibiting deterioration in proton acceptor properties, no proton acceptor properties, or a change from the proton acceptor properties to acid properties means a change of proton acceptor properties due to the proton being added to the functional group with proton acceptor properties, and specifically a decrease in the equilibrium constant at chemical equilibrium when a proton adduct is generated from the compound (PA) having the functional group with proton acceptor properties and the proton.

The proton acceptor properties can be confirmed by carrying out pH measurement.

In the present invention, the acid dissociation constant pKa of the compound generated by the decomposition of the compound (PA) upon irradiation with active light or radiation preferably satisfies pKa<−1, more preferably −13<pKa<−1, and still more preferably −13<pKa<−3.

In the present invention, the acid dissociation constant pKa indicates an acid dissociation constant pKa in an aqueous solution, and is described, for example, in Chemical Handbook (II) (Revised 4$^{th}$ Edition, 1993, compiled by the Chemical Society of Japan, Maruzen Company, Ltd.), and a lower value thereof indicates higher acid strength. Specifically, the pKa in an aqueous solution may be measured by using an infinite-dilution aqueous solution and measuring the acid dissociation constant at 25° C., or a value based on the Hammett substituent constants and the database of publicly known literature data can also be obtained by computation using the following software package 1. All the values of pKa described in the present specification indicate values determined by computation using this software package.

Software package 1: Advanced Chemistry Development (ACD/Labs) Software V 8.14 for Solaris (1994-2007 ACD/Labs).

The compound (PA) generates a compound represented by the following General Formula (PA-1), for example, as the proton adduct generated by decomposition upon irradiation with active light or radiation. The compound represented by General Formula (PA-1) is a compound exhibiting deterioration in proton acceptor properties, no proton acceptor properties, or a change from the proton acceptor properties to acid properties since the compound has a functional group with proton acceptor properties as well as an acidic group, as compared with the compound (PA).

Q-A-(X)$_n$—B—R    (PA-1)

In General Formula (PA-1),

Q represents —SO$_3$H, —CO$_2$H, or —W$_1$NHW$_2$R$_f$, in which R$_f$ represents an alkyl group (preferably having 1 to 20 carbon atoms), a cycloalkyl group (preferably having 3 to 20 carbon atoms), or an aryl group (preferably having 6 to 30 carbon atoms), and W$_1$ and W$_2$ each independently represent —SO$_2$— or —CO—.

A represents a single bond or a divalent linking group.

X represents —SO$_2$— or —CO—.

n is 0 or 1.

B represents a single bond, an oxygen atom, or —N(R$_x$)R$_y$—, in which R$_x$ represents a hydrogen atom or a monovalent organic group, and R$_y$ represents a single bond or a divalent organic group, provided that R$_x$ may be bonded to R$_y$ to form a ring or may be bonded to R to form a ring.

R represents a monovalent organic group having a functional group with proton acceptor properties.

General Formula (PA-1) will be described in more detail.

The divalent linking group in A is preferably a divalent linking group having 2 to 12 carbon atoms, such as and examples thereof include an alkylene group and a phenylene group. The divalent linking group is more preferably an alkylene group having at least one fluorine atom, preferably having 2 to 6 carbon atoms, and more preferably having 2 to 4 carbon atoms. The alkylene chain may contain a linking group such as an oxygen atom and a sulfur atom. In particular, the alkylene group is preferably an alkylene group in which 30% to 100% by number of the hydrogen atoms are substituted with fluorine atoms, and more preferably, the carbon atom bonded to the Q site has a fluorine atom. The alkylene group is still more preferably a perfluoroalkylene group, and even still more preferably a perfluoroethylene group, a perfluoropropylene group, or a perfluorobutylene group.

The monovalent organic group in R$_x$ is preferably an organic group having 1 to 30 carbon atoms, and examples thereof include an alkyl group, a cycloalkyl group, an aryl group, an aralkyl group, and an alkenyl group. These groups may further have a substituent.

The alkyl group in R$_x$ may have a substituent, is preferably a linear and branched alkyl group having 1 to 20 carbon atoms, and may have an oxygen atom, a sulfur atom, or a nitrogen atom in the alkyl chain.

The cycloalkyl group in R$_x$ may have a substituent, is preferably a monocyclic cycloalkyl or polycyclic cycloalkyl group having 3 to 20 carbon atoms, and may have an oxygen atom, a sulfur atom, or a nitrogen atom in the ring.

The aryl group in R$_x$ may have a substituent, is preferably an aryl group having 6 to 14 carbon atoms, and examples thereof include a phenyl group and a naphthyl group.

The aralkyl group in R$_x$ may have a substituent, is preferably an aralkyl group having 7 to 20 carbon atoms, and examples thereof include a benzyl group and a phenethyl group.

The alkenyl group in R$_x$ may have a substituent and may be linear or branched. The alkenyl group is preferably an alkenyl group having 3 to 20 carbon atoms. Examples of the alkenyl group include a vinyl group, an allyl group, and a styryl group.

Examples of a substituent in the case where R$_x$ further has a substituent include a halogen atom, a linear, branched, or cyclic alkyl group, an alkenyl group, an alkynyl group, an aryl group, an acyl group, an alkoxycarbonyl group, an aryloxycarbonyl group, a carbamoyl group, a cyano group, a carboxyl group, a hydroxyl group, an alkoxy group, an aryloxy group, an alkylthio group, an arylthio group, a heterocyclic oxy group, an acyloxy group, an amino group, a nitro group, a hydrazino group, and a heterocyclic group.

Preferred examples of the divalent organic group in R$_y$ include an alkylene group.

Examples of the ring structure which may be formed by the mutual bonding of R$_x$ and R$_y$ include a 5- to 10-membered ring, and particularly preferably a 6-membered ring, each containing a nitrogen atom.

The functional group with proton acceptor properties in R is the same as above, and examples thereof include groups having a heterocyclic aromatic structure including nitrogen, azacrown ether, primary to tertiary amines, pyridine, and imidazole.

The organic group having such a structure is preferably an organic group having 4 to 30 carbon atoms, and examples thereof include an alkyl group, a cycloalkyl group, an aryl group, an aralkyl group, and an alkenyl group.

In the alkyl group, the cycloalkyl group, the aryl group, the aralkyl group, or the alkenyl group containing a functional group with proton acceptor properties or an ammonium group in R, the alkyl group, the cycloalkyl group, the aryl group, the aralkyl group, or the alkenyl group is the same as the alkyl group, the cycloalkyl group, the aryl group, the aralkyl group, or the alkenyl group as mentioned as R$_x$, respectively.

When B is —N(R$_x$)R$_y$—, it is preferable that R and R$_x$ are bonded to each other to form a ring. The formation of a ring structure improves the stability and enhances the storage stability of a composition using the same. The number of carbon atoms which form a ring is preferably 4 to 20, the ring may be monocyclic or polycyclic, and an oxygen atom, and a sulfur atom, or a nitrogen atom may be contained in the ring.

Examples of the monocyclic structure include a 4-membered ring, a 5-membered ring, a 6-membered ring, a 7-membered ring, and a 8-membered ring, each containing a nitrogen atom, or the like. Examples of the polycyclic structure include structures formed by a combination of two, or three or more monocyclic structures.

$R_f$ of —$W_1NHW_2R_f$ represented by Q is preferably an alkyl group having 1 to 6 carbon atoms, which may have a fluorine atom, and more preferably a perfluoroalkyl group having 1 to 6 carbon atoms. Further, it is preferable that at least one of $W_1$ or $W_2$ is —$SO_2$—, with a case where both $W_1$ and $W_2$ are —$SO_2$— being more preferable.

Q is particularly preferably —$SO_3H$ or —$CO_2H$ from the viewpoint of the hydrophilicity of an acid group.

The compound represented by General Formula (PA-1) in which Q site is sulfonic acid can be synthesized by a common sulfonamidation reaction. For example, the compound can be synthesized by a method in which one sulfonyl halide moiety of a bissulfonyl halide compound is selectively reacted with an amine compound to form a sulfonamide bond, and then the another sulfonyl halide moiety thereof is hydrolyzed, or a method in which a cyclic sulfonic acid anhydride is reacted with an amine compound to cause ring opening.

The compound (PA) is preferably an ionic compound. The functional group with proton acceptor properties may be contained in an anion moiety or a cation moiety, and it is preferable that the functional group is contained in an anion moiety.

Preferred examples of the compound (PA) include compounds represented by the following General Formulae (4) to (6).

$R_f$—$W_2$—$N^-$—$W_1$-A-(X)$_n$—B—R[C]$^+$ (4)

R—$SO_3^-$[C]$^+$ (5)

R—$CO_2^-$[C]$^+$ (6)

In General Formulae (4) to (6), A, X, n, B, R, $R_f$, $W_1$, and $W_2$ each have the same definitions as in General Formula (PA-1).

C$^+$ represents a counter cation.

The counter cation is preferably an onium cation. More specifically, more preferred examples thereof include a sulfonium cation described as S$^+$($R_{201}$)($R_{202}$)($R_{203}$) in General Formula (ZI) and an iodonium cation described as I$^+$($R_{204}$)($R_{205}$) in General Formula (ZII) with regard to the acid generator which will be described later.

Specific examples of the compound (PA) include the compounds exemplified in [0280] of US2011/0269072A1.

Furthermore, in the present invention, compounds (PA) other than a compound which generates the compound represented by General Formula (PA-1) can also be appropriately selected. For example, a compound containing a proton acceptor moiety at its cation moiety may be used as an ionic compound. More specific examples thereof include a compound represented by the following General Formula (7).

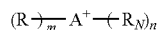

(7)

In the formula, A represents a sulfur atom or an iodine atom.

m represents 1 or 2 and n represents 1 or 2, provided that m+n=3 when A is a sulfur atom and that m+n=2 when A is an iodine atom.

R represents an aryl group.

$R_N$ represents an aryl group substituted with the functional group with proton acceptor properties, and X$^-$ represents a counter anion.

Specific examples of X$^-$ include the same anions as those of the acid generators as described above.

Specific preferred examples of the aryl group of R and $R_N$ include a phenyl group.

Specific examples of the functional group with proton acceptor properties contained in $R_N$ below are the same as those of the functional group with proton acceptor properties as described above in Formula (PA-1).

Specific examples of the ionic compounds having a proton acceptor site at a cationic moiety include the compounds exemplified in [0291] of US2011/0269072A1.

Furthermore, such compounds can be synthesized, for example, with reference to the methods described in JP2007-230913A, JP2009-122623A, and the like.

The compound (PA) may be used alone or in combination of two or more kinds thereof.

The content of the compound (PA) is preferably 0.1% to 10% by mass, and more preferably 1% to 8% by mass, with respect to the total solid content of the composition.

The composition of the present invention can use an onium salt which becomes a relatively weak acid with respect to the acid generator, as an acid diffusion control agent (D).

In the case of mixing the acid generator and the onium salt that generates an acid which is a relatively weak acid (preferably an acid having a pKa of more than −1) with respect to an acid generated from the acid generator and then using the mixture, when the acid generated from the acid generator upon irradiation with active light or radiation collides with an onium salt having an unreacted weak acid anion, a weak acid is discharged by salt exchange, thereby generating an onium salt having a strong acid anion. In this process, the strong acid is exchanged with a weak acid having a lower catalytic ability, and therefore, the acid is deactivated in appearance, and thus, it is possible to carry out the control of acid diffusion.

As the onium salt which becomes a relatively weak acid with respect to the acid generator, compounds represented by the following General Formulae (d1-1) to (d1-3) are preferable.

(d1-1)

(d1-2)

(d1-3)

In the formulae, R$^{51}$ is a hydrocarbon group which may have a substituent, Z$^{2c}$ is a hydrocarbon group (provided that carbon adjacent to S is not substituted with a fluorine atom)

having 1 to 30 carbon atoms, which may have a substituent, $R^{52}$ is an organic group, $Y^3$ is a linear, branched, or cyclic alkylene group or arylene group, Rf is a hydrocarbon group containing a fluorine atom, and $M^+$'s are each independently a sulfonium or iodonium cation.

Preferred examples of the sulfonium cation or the iodonium cation represented by $M^+$ include the sulfonium cations exemplified by an acid generator (ZI) and the iodonium cations exemplified by (ZII).

Preferred examples of the anionic moiety of the compound represented by General Formula (d1-1) include the structures exemplified in paragraph [0198] of JP2012-242799A.

Preferred examples of the anionic moiety of the compound represented by General Formula (d1-2) include the structures exemplified in paragraph [0201] of JP2012-242799A.

Preferred examples of the anionic moiety of the compound represented by General Formula (d1-3) include the structures exemplified in paragraphs [0209] and [0210] of JP2012-242799A.

The onium salt which becomes a relatively weak acid with respect to the acid generator may be a compound having a cationic moiety and an anionic moiety in the same molecule (hereinafter also referred to as a "compound (D-2)"), in which the cationic moiety and the anionic moiety are linked to each other via a covalent bond.

As the compound (D-2), a compound represented by any one of the following General Formulae (C-1) to (C-3) is preferable.

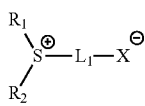

(C-1)

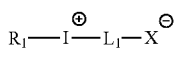

(C-2)

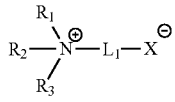

(C-3)

In General Formulae (C-1) to (C-3), $R_1$, $R_2$, and $R_3$ represent a substituent having 1 or more carbon atoms.

$L_1$ represents a divalent linking group that links a cationic moiety with an anionic moiety, or a single bond.

—$X^-$ represents an anionic moiety selected from —COO$^-$, —SO$_3^-$, —SO$_2^-$, and —N$^-$—R$_4$. $R_4$ represents a monovalent substituent having a carbonyl group: —C(=O)—, a sulfonyl group: —S(=O)$_2$—, or a sulfinyl group: —S(=O)— at a site for linking to an adjacent N atom.

$R_1$, $R_2$, $R_3$, $R_4$, and $L_1$ may be bonded to one another to form a ring structure. Further, in (C-3), two members out of $R_1$ to $R_3$ may be combined to form a double bond with an N atom.

Examples of the substituent having 1 or more carbon atoms in $R_1$ to $R_3$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group, and preferably an alkyl group, a cycloalkyl group, and an aryl group.

Examples of $L_1$ as a divalent linking group include a linear or branched alkylene group, a cycloalkylene group, an arylene group, a carbonyl group, an ether bond, ester bond, amide bond, a urethane bond, a urea bond, and a group formed by a combination of two or more kinds of these groups. $L_1$ is more preferably alkylene group, an arylene group, an ether bond, ester bond, and a group formed by a combination of two or more kinds of these groups.

Preferred examples thereof the compound represented by General Formula (C-1) include the compounds exemplified in paragraphs [0037] to [0039] of JP2013-6827A and paragraphs [0027] to [0029] of JP2013-8020A.

Preferred examples thereof the compound represented by General Formula (C-2) include the compounds exemplified in paragraphs [0012] to [0013] of JP2012-189977A.

Preferred examples thereof the compound represented by General Formula (C-3) include the compounds exemplified in paragraphs [0029] to [0031] of JP2012-252124A.

The content of the onium salt which becomes a relatively weak acid with respect to the acid generator is preferably 0.5% to 10.0% by mass, more preferably 0.5% to 8.0% by mass, and still more preferably 1.0% to 8.0% by mass, with respect to the solid content of the composition.

<Solvent>

The composition of the present invention usually contains a solvent.

Examples of the solvent which can be used in the preparation of the composition include organic solvents such as alkylene glycol monoalkyl ether carboxylate, alkylene glycol monoalkyl ether, alkyl lactate ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

Specific examples of these solvents include ones described in, for example, [0441] to [0455] of US2008/0187860A.

In the present invention, a mixed solvent obtained by mixing a solvent containing a hydroxyl group and a solvent containing no hydroxyl group in the structure may be used as the organic solvent.

As the solvent containing a hydroxyl group and the solvent containing no hydroxyl group, the aforementioned exemplary compounds can be appropriately selected and used, but as the solvent containing a hydroxyl group, an alkylene glycol monoalkyl ether, alkyl lactate, and the like are preferable, and propylene glycol monomethyl ether (PGME, alternative name: 1-methoxy-2-propanol) and ethyl lactate are more preferable. Further, as the solvent containing no hydroxyl group, alkylene glycol monoalkyl ether acetate, alkyl alkoxy propionate, a monoketone compound which may contain a ring, cyclic lactone, alkyl acetate, and the like are preferable. Among these, propylene glycol monomethyl ether acetate (PGMEA, alternative name: 1-methoxy-2-acetoxypropane), ethyl ethoxypropionate, 2-heptanone, γ-butyrolactone, cyclohexanone, and butyl acetate are particularly preferable, and propylene glycol monomethyl ether acetate, ethyl ethoxypropionate, and 2-heptanone are most preferable.

The mixing ratio (based on mass) of the solvent containing a hydroxyl group and the solvent containing no hydroxyl group is 1/99 to 99/1, preferably 10/90 to 90/10, and more preferably 20/80 to 60/40. A mixed solvent whose proportion of the solvent containing no hydroxyl group is 50% by mass or more is particularly preferable from the viewpoint of coating evenness.

The solvent preferably contains propylene glycol monomethyl ether acetate, and is preferably a solvent composed of propylene glycol monomethyl ether acetate alone or a mixed solvent of two or more kinds of solvents including propylene glycol monomethyl ether acetate.

<Other Additives>

The composition of the present invention may or may not contain an onium carboxylate salt. Examples of such an onium carboxylate salt include those described in [0605] to [0606] of US2008/0187860A.

The onium carboxylate salt can be synthesized by reacting sulfonium hydroxide, iodonium hydroxide, ammonium hydroxide and carboxylic acid with silver oxide in a suitable solvent.

In the case where the composition of the present invention contains the onium carboxylate salt, the content of the salt is generally 0.1% to 20% by mass, preferably 0.5% to 10% by mass, and more preferably 1% to 7% by mass, with respect to the total solid content of the composition.

The composition of the present invention may further contain an acid diffusing agent, a cross-linking agent, a dye, a plasticizer, a light sensitizer, a light absorbent, an alkali-soluble resin, a dissolution inhibitor, a compound promoting solubility in a developer (for example, a phenol compound with a molecular weight of 1,000 or less, an alicyclic or aliphatic compound having a carboxyl group), and the like, if desired.

Such a phenol compound having a molecular weight of 1,000 or less may be easily synthesized by those skilled in the art with reference to the method disclosed in, for example, JP1992-122938A (JP-H04-122938A), JP1990-28531A (JP-H02-28531A), U.S. Pat. No. 4,916,210A, EP219294B, and the like.

Specific examples of the alicyclic compound or aliphatic compound having a carboxyl group include, but not limited to, a carboxylic acid derivative having a steroid structure such as a cholic acid, deoxycholic acid or lithocholic acid, an adamantane carboxylic acid derivative, adamantane dicarboxylic acid, cyclohexane carboxylic acid, and cyclohexane dicarboxylic acid.

The composition of the present invention is preferably a resist film having a film thickness of 80 nm or less from the viewpoint of improving the resolving power. It is possible to set the film thickness by setting the concentration of the solid content in the composition to an appropriate range to have a suitable viscosity and improving a coating property and a film forming property.

The concentration of the solid content of the composition of the present invention is usually 1.0% to 10% by mass, preferably 2.0% to 5.7% by mass, and more preferably 2.0% to 5.3% by mass. By setting the concentration of the solid content to these ranges, it is possible to uniformly coat the resist solution on a substrate and additionally, it is possible to form a resist pattern having excellent line width roughness. The reason is not clear; however, it is considered that, by setting the concentration of the solid content to 10% by mass or less and preferably 5.7% by mass or less, the aggregation of materials, particularly the photoacid generator, in the resist solution is suppressed and, as the result, it is possible to form a uniform resist film.

The concentration of the solid content is the mass percentage of the mass of other the resist components excluding the solvent with respect to the total mass of the composition.

The composition of the present invention is used by dissolving the components in a predetermined organic solvent, and preferably in the mixed solvent, filtering the solution through a filter, and then applying the filtered solution on a predetermined substrate. The filter used for filtration is preferably a polytetrafluoroethylene-, polyethylene- or nylon-made filter having a pore size of 0.1 µm or less, more preferably 0.05 µm or less, and still more preferably 0.03 µm or less. In the filtration through a filter, as described in, for example, JP2002-62667A, circulating filtration may be carried out, or the filtration may be carried out by connecting two or more kinds of filters in series or in parallel. In addition, the composition may be filtered a plurality of times. Furthermore, the composition may be subjected to a deaeration treatment or the like before or after filtration through a filter.

The composition of the present invention is related to an active-light-sensitive or radiation-sensitive resin composition whose properties change by a reaction upon irradiation with active light or radiation. More specifically, the present invention relates to an active-light-sensitive or radiation-sensitive resin composition used in for a step of manufacturing a semiconductor such as an IC, for manufacture of liquid crystals and a circuit board for a thermal head or the like, the manufacture of a mold structure for imprinting, or other photofabrication processes, or used in a lithographic printing plate or an acid-curable composition.

[Pattern Forming Method]

Next, the pattern forming method of the present invention will be described.

The pattern forming method of the present invention includes at least the following steps (i) to (iii):

a step (i) of forming an active-light-sensitive or radiation-sensitive film (hereinafter also simply referred to as a film) on a substrate, using the composition of the present invention, a step (ii) of exposing the active-light-sensitive or radiation-sensitive film (exposing step), and a step (iii) of developing the exposed active-light-sensitive or radiation-sensitive film using a developer to form a pattern (developing step).

The exposure in the step (ii) may be a liquid immersion exposure.

The pattern forming method of the present invention preferably includes a heating step (iv) after the exposing step (ii).

The pattern forming method of the present invention may further include the exposing step (ii) in plural times.

The pattern forming method of the present invention may include the heating step (iv) in plural times.

In the pattern forming method of the present invention, the step of forming the active-light-sensitive or radiation-sensitive film on a substrate, using the composition of the present invention, the step of exposing the active-light-sensitive or radiation-sensitive film, and the developing step can be carried out by a generally known method.

The substrate on which the active-light-sensitive or radiation-sensitive film is formed in the present invention is not particularly limited, and it is possible to use an inorganic substrate such as silicon, $SiO_2$ and SiN, a coating type inorganic substrate such as SOG, or a substrate generally used in a process for manufacturing a semiconductor such as an IC, in a process for manufacture of liquid crystals and a circuit board for a thermal head or the like, and in other lithographic processes of photofabrication. Further, if desired, an antireflection film may be formed between the resist film and the substrate. As the antireflection film, a known organic or inorganic antireflection film can be appropriately used.

It is also preferable that the method includes a pre-heating step (PB; Prebake) after forming a film and before the exposing step.

In addition, it is also preferable that the method includes a step of heating after exposure (PEB: Post Exposure Bake), after the exposing step and before the developing step.

For both of PB and PEB, the heating is preferably carried out at a heating temperature of 70° C. to 130° C., and more preferably 80° C. to 120° C.

The heating time is preferably 30 to 300 seconds, more preferably 30 to 180 seconds, and still more preferably 30 to 90 seconds.

Heating may be carried out using a means installed in an ordinary exposure-and-development machine, or may also be carried out using a hot plate or the like.

Baking accelerates the reaction in the exposed areas, and thus, the sensitivity and the pattern profile are enhanced.

The light source wavelength used in the exposure device in the present invention is not limited, and examples thereof include infrared rays, visible light, ultraviolet rays, far ultraviolet rays, extreme ultraviolet rays, X-rays, and electron beams, for example, far ultraviolet rays at a wavelength of preferably 250 nm or less, more preferably 220 nm or less, and particularly preferably 1 to 200 nm, specifically a KrF excimer laser (248 nm), an ArF excimer laser (193 nm), an $F_2$ excimer laser (157 nm), X-rays, EUV (13 nm), electron beams, and the like, with the KrF excimer laser, the ArF excimer laser, EUV, or the electron beams being preferable, and the ArF excimer laser being more preferable.

Furthermore, a liquid immersion exposure method can be applied to the step of carrying out exposure of the present invention. It is possible to combine the liquid immersion exposure method with super-resolution technology such as a phase shift method and a modified illumination method.

In the case of carrying out the liquid immersion exposure, a step of cleaning the surface of a film with an aqueous chemical liquid may be carried out (1) after forming a film on a substrate and before an exposing step, and/or (2) after a step of subjecting the film to exposure through an immersion liquid and before heating the film.

The immersion liquid is preferably a liquid which is transparent to exposure wavelength and has a minimum temperature coefficient of refractive index so as to minimize the distortion of an optical image projected on the film. In particular, in the case where the exposure light source is an ArF excimer laser (wavelength: 193 nm), water is preferably used in terms of easy availability and easy handling, in addition to the above-described viewpoints.

In the case of using water, an additive (liquid) that decreases the surface tension of water while increasing the interfacial activity may be added at a slight proportion. It is preferable that this additive does not dissolve the resist film on a wafer, and gives a negligible effect on the optical coat at the undersurface of a lens element.

Such an additive is preferably for example, an aliphatic alcohol having a refractive index substantially equal to that of water, and specific examples thereof include methyl alcohol, ethyl alcohol, and isopropyl alcohol. By adding an alcohol having a refractive index substantially equal to that of water, even when the alcohol component in water is evaporated and its content concentration is changed, an advantage in that the change in the refractive index of the liquid as a whole can be advantageously made very small is obtained.

On the other hand, in the case where materials opaque to light at 193 nm or impurities having a great difference in the refractive index from water are incorporated, the distortion of an optical image projected on a resist is caused. Therefore, the water to be used is preferably distilled water. Further, pure water after filtration through an ion exchange filter or the like may also be used.

The electrical resistance of water used as the immersion liquid is preferably 18.3 MΩcm or more, and Total Organic Concentration (TOC) is preferably 20 ppb or less. The water is preferably one which has been subjected to a deaeration treatment.

In addition, the lithography performance can be enhanced by increasing the refractive index of the immersion liquid. From such a viewpoint, an additive for increasing the refractive index may be added to water, or heavy water ($D_2O$) may be used in place of water.

The receding contact angle of the resist film formed using the composition in the present invention is preferably 70° or more at a temperature of 23±3° C. at a humidity of 45±5%, which is suitable in the case of the exposure through a liquid immersion medium. The receding contact angle is preferably 75° or more, and more preferably 75° to 85°.

If the receding contact angle is extremely small, the resist film cannot be appropriately used in the case of the exposure through a liquid immersion medium. Further, it is not possible to sufficiently exhibit the effect of reducing defects due to remaining water (water marks). In order to realize a favorable receding contact angle, it is preferable to incorporate the hydrophobic resin into the composition. Alternatively, a film (hereinafter also referred to as a "top coat") which is sparingly soluble in an immersion liquid, which is formed of the hydrophobic resin, may be formed on the upper layer of the resist film. The functions required for the top coat are coating suitability on the upper layer part of a resist film, and sparing solubility in an immersion liquid. It is preferable that the top coat is not mixed with the composition film and can be uniformly applied onto the upper layer of a composition film.

Specific examples of the top coat include a hydrocarbon polymer, an acrylic acid ester polymer, a polymethacrylic acid, a polyacrylic acid, a polyvinyl ether, a silicon-containing polymer, and a fluorine-containing polymer. From the viewpoint that if impurities are eluted into the immersion liquid from the top coat, an optical lens is contaminated, it is preferable that a smaller amount of residual monomer components of the polymer is included in the top coat.

On releasing the top coat, a developer may be used, or a release agent may be separately used. As the release agent, a solvent which is less likely to permeate the film is preferable. From the viewpoint that this releasing step can be carried out simultaneously with the film developing step, the top coat is preferably releasable with a developer including an organic solvent.

When the difference in the refractive index between the top coat and the immersion liquid is null, the resolving power is improved. In the case where water is used as the immersion liquid, the top coat preferably has a refractive index close to that of the immersion liquid. From the viewpoint of making the refractive index close to that of the immersion liquid, it is preferable that the top coat has a fluorine atom. In addition, from the viewpoints of the transparency and the refractive index, it is preferable that the top coat is a thin film.

It is preferable that the top coat is unmixable with the film and further unmixable also with the immersion liquid. From this viewpoint, in the case where the immersion liquid is water, the solvent used for the top coat is preferably a medium that is sparingly soluble in the solvent used for the composition of the present invention and is water-insoluble.

Furthermore, in the case where the immersion liquid is an organic solvent, the top coat may be either water-soluble or water-insoluble.

Formation of a top coat layer is not limited to a case of the liquid immersion exposure, and may also be carried out in the case of dry exposure (exposure not through an immersion liquid). By forming the top coat layer, for example, generation of out gas can be inhibited.

Hereinafter, the top coat composition used for formation of the top coat layer will be described.

In the top coat composition in the present invention, the solvent is preferably an organic solvent, and more preferably an alcohol-based solvent.

In the case where the solvent is an organic solvent, a solvent incapable of dissolving the active-light-sensitive or radiation-sensitive film is preferable. As the solvent which can be used, an alcohol-based solvent, a fluorine-based solvent, or a hydrocarbon-based solvent is preferably used, and a fluorine-free alcohol-based solvent is more preferably used. The alcohol-based solvent is, from the viewpoint of coatability, preferably a primary alcohol, and more preferably a primary alcohol having 4 to 8 carbon atoms. As the primary alcohol having 4 to 8 carbon atoms, a linear, branched, or cyclic alcohol can be used, and preferred examples thereof include 1-butanol, 1-hexanol, 1-pentanol, 3-methyl-1-butanol, 2-ethylbutanol, and perfluorobutyl tetrahydrofuran.

Furthermore, as the resin for the top coat composition, the resins having an acidic group described in JP2009-134177A and JP2009-91798A can also be preferably used.

The weight-average molecular weight of the water-soluble resin is not particularly limited, but is preferably 2,000 to 1,000,000, more preferably 5,000 to 500,000, and particularly preferably 10,000 to 100,000. Here, the weight-average molecular weight of the resin indicates a molecular weight in terms of polystyrene measured by GPC (carrier: THF or N-methyl-2-pyrrolidone (NMP)).

The pH of the top coat composition is not particularly limited, but is preferably 0 to 10, more preferably 0 to 8, and particularly preferably 1 to 7.

The concentration of the resin in the top coat composition is preferably 0.1% to 10% by mass, more preferably 0.2% to 5% by mass, and particularly preferably 0.3% to 3% by mass.

The top coat material may contain components other than the resin, but the proportion of the resin in the solid content of the top coat composition is preferably 80% to 100% by mass, more preferably 90% to 100% by mass, and particularly preferably 95% to 100% by mass.

The concentration of the solid content of the top coat composition for use in the present invention is preferably 0.1% to 10% by mass, more preferably 0.2% to 6% by mass, and still more preferably 0.3% to 5% by mass. By adjusting the concentration of the solid content to fall in the range above, the top coat composition can be uniformly coated on the resist film.

In the pattern forming method of the present invention, an active-light-sensitive or radiation-sensitive film can be formed on a substrate by using the composition, and a top coat layer can be formed on the film by using the top coat composition. The film thickness of the active-light-sensitive or radiation-sensitive film is preferably 10 to 100 nm, and the film thickness of the top coat layer is preferably 10 to 200 nm, more preferably 20 to 100 nm, and particularly preferably 40 to 80 nm.

The method for coating the composition on a substrate is preferably spin coating, and the rotation speed thereof is preferably 1,000 to 3,000 rpm.

For example, the composition is applied onto such a substrate as used in the production of a precision integrated circuit device (e.g.: a silicon/silicon dioxide-coated substrate) by an appropriate coating method using a spinner, a coater, or the like, and then dried to form a resist film. Incidentally, a known antireflection film may be previously provided by coating. In addition, it is preferable that the active-light-sensitive or radiation-sensitive film is dried before forming a top coat layer.

Subsequently, the top coat composition is applied onto the obtained active-light-sensitive or radiation-sensitive film by the same method as the method for forming the active-light-sensitive or radiation-sensitive film, and dried, whereby a top coat layer can be formed.

The active-light-sensitive or radiation-sensitive film having a top coat layer on the upper layer thereof is irradiated with active light or radiation, usually through a mask, then preferably baked (heated), and further developed, whereby a good pattern can be obtained.

In the liquid immersion exposing step, it is necessary for the immersion liquid to move on a wafer following the movement of an exposure head which scans the wafer at a high speed to form an exposure pattern. Therefore, the contact angle of the immersion liquid for the active-light-sensitive or radiation-sensitive film in a dynamic state is important, and the resist is required to have a performance of allowing the immersion liquid to follow the high-speed scanning of an exposure head with no remaining of a liquid droplet.

The developer used in the step of developing the active-light-sensitive or radiation-sensitive composition film formed using the composition of the present invention is not particularly limited, but an alkali developer or a developer containing an organic solvent (hereinafter also referred to as an organic developer), for example, can be used. Among these, the developer containing an organic solvent is preferably used.

As the alkali developer, for example, an aqueous alkali solution of inorganic alkalis such as sodium hydroxide, potassium hydroxide, sodium carbonate, sodium silicate, sodium metasilicate, and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, tetraalkyl ammonium hydroxide such as tetramethylammonium hydroxide, tetraethylammonium hydroxide, tetrapropylammonium hydroxide, tetrabutylammonium hydroxide, tetrapentyl ammonium hydroxide, tetrahexylammonium hydroxide, tetraoctylammonium hydroxide, ethyltrimethyl ammonium hydroxide, butyltrimethylammonium hydroxide, methyltriamylammonium hydroxide, and dibutyldipentylammonium hydroxide, quaternary ammonium salts such as trimethylphenylammonium hydroxide, trimethylbenzylammonium hydroxide, and triethylbenzylammonium hydroxide, or cyclic amines such as pyrrole and piperidine can be used. Further, it is also possible to use a developer by adding an appropriate amount of alcohols or a surfactant to the aqueous alkali solution. The alkali concentration of alkali developer is usually 0.1% to 20% by mass. The pH of the alkali developer is usually 10.0 to 15.0. The alkali concentration and the pH of the alkali developer may be appropriately adjusted and used. The alkali developer to which a surfactant or an organic solvent has been added may also be used.

Pure water is used as a rinsing liquid in the rinsing treatment which is carried out after the alkali development, and it may also be used after adding an appropriate amount of a surfactant thereto.

Incidentally, after the development treatment or the rinsing treatment, a treatment for removing the developer or the rinsing liquid adhering on the pattern by a supercritical fluid may be carried out.

As the organic developer, a polar solvent such as a ketone-based solvent, an ester-based solvent, an alcohol-based solvent, an amide-based solvent, and an ether-based solvent, or a hydrocarbon-based solvent can be used. Specific examples thereof include the solvents described in paragraph [0507] of JP2013-218223A.

A plurality of solvents may be mixed or the solvents may be used by mixing with solvents other than the solvents described above or water. However, in order to sufficiently exhibit the effects of the present invention, the moisture content for the entirety of the developer is preferably less than 10% by mass, and water is more preferably substantially not contained.

That is, the amount of the organic solvent to be used with respect to the organic developer is preferably 90% by mass to 100% by mass, and more preferably 95% by mass to 100% by mass, with respect to the total amount of the developer.

In particular, the organic developer is preferably a developer containing at least one organic solvent selected from the group consisting of a ketone-based solvent, an ester-based solvent, an alcohol-based solvent, an amide-based solvent, and an ether-based solvent.

The vapor pressure of the organic developer at 20° C. is preferably 5 kPa or less, more preferably 3 kPa or less, and particularly preferably 2 kPa or less. By setting the vapor pressure of the organic developer to 5 kPa or less, the evaporation of the developer on the substrate or in a developing cup is inhibited, the temperature uniformity in the wafer surface is improved, and as a result, the dimensional uniformity within a wafer surface is improved.

It is possible to add an appropriate amount of a surfactant to the organic developer, if necessary.

The surfactant is not particularly limited, but it is possible to use, for example, ionic or non-ionic fluorine-based and/or silicon-based surfactants, or the like. Examples of the fluorine-based and/or the silicon-based surfactant include the surfactants described in JP1987-36663A (JP-S62-36663A), JP1986-226746A (JP-S61-226746A), JP1986-226745A (JP-S61-226745A), JP1987-170950A (JP-S62-170950A), JP1988-34540A (JP-S63-34540A), JP1995-230165A (JP-H7-230165A), JP1996-62834A (JP-H8-62834A), JP1997-54432A (JP-H9-54432A), JP1997-5988A (JP-H9-5988A), U.S. Pat. No. 5,405,720A, U.S. Pat. No. 5,360,692A, U.S. Pat. No. 5,529,881A, U.S. Pat. No. 5,296,330A, U.S. Pat. No. 5,436,098A, U.S. Pat. No. 5,576,143A, U.S. Pat. No. 5,294,511A, and U.S. Pat. No. 5,824,451A, and non-ionic surfactants are preferable. The non-ionic surfactant is not particularly limited, but it is more preferable to use a fluorine-based surfactant or a silicon-based surfactant.

The amount of the surfactant to be used is usually 0.001% to 5% by mass, preferably 0.005% to 2% by mass, and more preferably 0.01% to 0.5% by mass, with respect to the total amount of the developer.

The organic developer may also include a basic compound. Specific and preferred examples of the basic compound which can be included in the organic developer used in the present invention include the same ones as for the basic compound which can be included in the aforementioned composition as the acid diffusion control agent (D).

As the developing method, for example, a method in which a substrate is immersed in a tank filled with a developer for a certain period of time (a dip method), a method in which a developer is heaped up to the surface of a substrate by surface tension and developed by stopping for a certain period of time (a paddle method), a method in which a developer is sprayed on the surface of a substrate (a spray method), a method in which a developer is continuously discharged on a substrate spun at a constant rate while scanning a developer discharging nozzle at a constant rate (a dynamic dispense method), or the like, can be applied.

In the case where the various developing methods include a step of discharging a developer toward a resist film from a development nozzle of a developing device, the discharge pressure of the developer discharged (the flow velocity per unit area of the developer discharged) is preferably 2 mL/sec/mm$^2$ or less, more preferably 1.5 mL/sec/mm$^2$ or less, and still more preferably 1 mL/sec/mm$^2$ or less. The flow velocity has no particular lower limit, but is preferably 0.2 mL/sec/mm$^2$ or more in consideration of a throughput.

By setting the discharge pressure of the discharged developer to the aforementioned range, pattern defects resulting from the resist scum after development may be significantly reduced.

Although details on the mechanism are not clear, it is thought to be due to a fact that the pressure imposed on the resist film by the developer is decreased by setting the discharge pressure to the above range so that the resist film and the resist pattern are inhibited from being inadvertently cut or collapsing.

Furthermore, the discharge pressure (mL/sec/mm$^2$) of the developer is the value at the outlet of the development nozzle in the developing device.

Examples of the method for adjusting the discharge pressure of the developer include a method of adjusting the discharge pressure by a pump or the like, and a method of supplying a developer from a pressurized tank and adjusting the pressure to change the discharge pressure.

In addition, after the step of carrying out development using a developer including an organic solvent, a step of stopping the development while replacing the solvent with another solvent may also be carried out.

In the pattern forming method of the present invention, a step of performing development by using a developer containing an organic solvent (organic solvent developing step) and a step of carrying out development by using an aqueous alkali solution (alkali developing step) may be used in combination. Due to this combination, a finer pattern can be formed.

In the present invention, an area with a low exposure intensity is removed in the organic solvent developing step, and by further carrying out the alkali developing step, an area with a high exposure intensity is also removed. By virtue of a multiple development process in which development is carried out a plurality of times in this way, a pattern can be formed by keeping only a region with an intermediate exposure intensity from being dissolved, so that a finer pattern than usual can be formed (the same mechanism as in [0077] of JP2008-292975A).

In the pattern forming method of the present invention, the order of the alkali developing step and the organic solvent developing step is not particularly limited, but the alkali development may be carried out before the organic solvent developing step, or the organic solvent developing step may be carried out before the alkali developing step.

It is preferable that a step of rinsing using a rinsing liquid is included after the step of carrying out development using a developer including an organic solvent.

The rinsing liquid used in the rinsing step after the step of carrying out development using a developer including an organic solvent is not particularly limited as long as the rinsing liquid does not dissolve the resist pattern, and a solution including a common organic solvent can be used. As the rinsing liquid, a rinsing liquid containing at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent are the same as those described for the developer containing an organic solvent.

After the developing step using a developer including an organic solvent, it is more preferable to carry out a step of cleaning using a rinsing liquid containing at least one organic solvent selected from the group consisting of a ketone-based solvent, an ester-based solvent, an alcohol-based solvent, and an amide-based solvent, it is still more preferable to carry out a step of cleaning using a rinsing liquid containing an alcohol-based solvent or an ester-based solvent, it is particularly preferable to carry out a step of cleaning using a rinsing liquid containing a monohydric alcohol, and it is most preferable to carry out a step of cleaning using a rinsing liquid containing a monohydric alcohol having 5 or more carbon atoms.

Here, examples of the monohydric alcohol used in the rinsing step include a linear, branched, or cyclic monohydric alcohol, and specifically, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol, or the like can be used. Further, 1-hexanol, 2-hexanol, 4-methyl-2-pentanol, 1-pentanol, 3-methyl-1-butanol, or the like can be used as a particularly preferred monohydric alcohol having 5 or more carbon atoms.

The respective components in plural numbers may be mixed, or the components may mixed with an organic solvents other than the above solvents, and used.

The moisture content of the rinsing liquid is preferably 10% by mass or less, more preferably 5% by mass or less, and particularly preferably 3% by mass or less. By setting the moisture content to 10% by mass or less, good development characteristics can be obtained.

The vapor pressure of the rinsing liquid which is used after the step of carrying out development using a developer including an organic solvent is preferably from 0.05 kPa to 5 kPa, more preferably from 0.1 kPa to 5 kPa, and most preferably from 0.12 kPa to 3 kPa, at 20° C. By setting the vapor pressure of the rinsing liquid to a range from 0.05 kPa to 5 kPa, the temperature uniformity within a wafer surface is improved, and further, the dimensional uniformity within a wafer surface is enhanced by inhibition of swelling due to the permeation of the rinsing liquid.

The rinsing liquid can also be used after adding an appropriate amount of a surfactant thereto.

In the rinsing step, the wafer which has been subjected to development using a developer including an organic solvent is subjected to a cleaning treatment using the rinsing liquid including an organic solvent. A method for the cleaning treatment is not particularly limited, and for example, a method in which a rinsing liquid is continuously discharged on a substrate rotated at a constant rate (a rotation application method), a method in which a substrate is immersed in a bath filled with a rinsing liquid for a certain period of time (a dip method), a method in which a rinsing liquid is sprayed on a substrate surface (a spray method), or the like, can be applied. Among these, a method in which a cleaning treatment is carried out using the rotation application method, and a substrate is rotated at a rotation speed of 2,000 rpm to 4,000 rpm after cleaning, thereby removing the rinsing liquid from the substrate, is preferable. Further, it is preferable that a heating step (Post Bake) is included after the rinsing step. The residual developer and the rinsing liquid between and inside the patterns are removed by the baking. The heating step after the rinsing step is carried out at typically 40° C. to 160° C., and preferably at 70° C. to 95° C., and typically for 10 seconds to 3 minutes, and preferably for 30 seconds to 90 seconds.

The pattern forming method of the present invention can be used in formation of a guide pattern (see, for example, ACS Nano Vol. 4 No. 8 Pages 4815-4823) in Directed Self-Assembly (DSA).

Furthermore, the resist pattern formed by the pattern forming method of the present invention can be used as a core material (core) in the spacer process disclosed in, for example, JP1991-270227A (JP-H03-270227A) and JP2013-164509A.

Moreover, the present invention also relates to a method for manufacturing an electronic device, including the pattern forming method of the present invention as described above, and an electronic device manufactured by the manufacturing method.

The electronic device of the present invention is suitably mounted on electric or electronic equipment (home electronics, OA/media-related equipment, optical equipment, telecommunication equipment, and the like).

EXAMPLES

Hereinafter, the present invention will be described with reference to Examples, but the present invention is not limited thereto.

Synthesis Example 1: Synthesis of Compound B1-5

A compound B1-5 was synthesized by the method shown below.

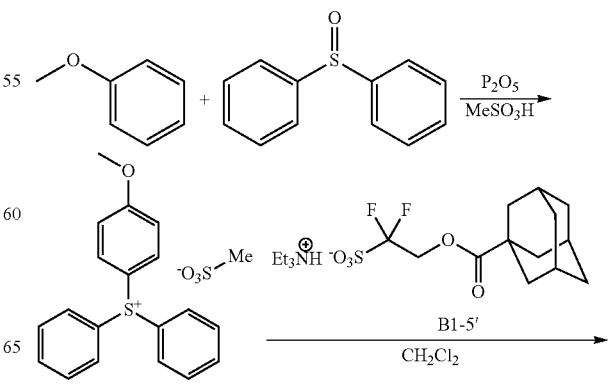

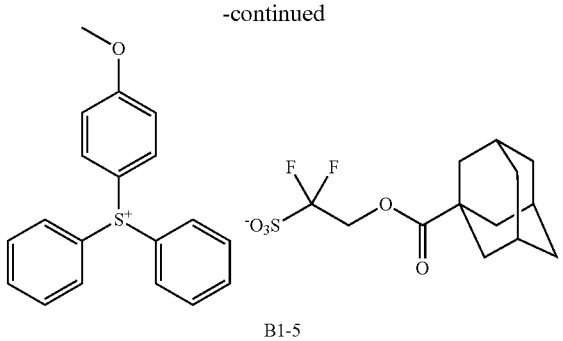

B1-5

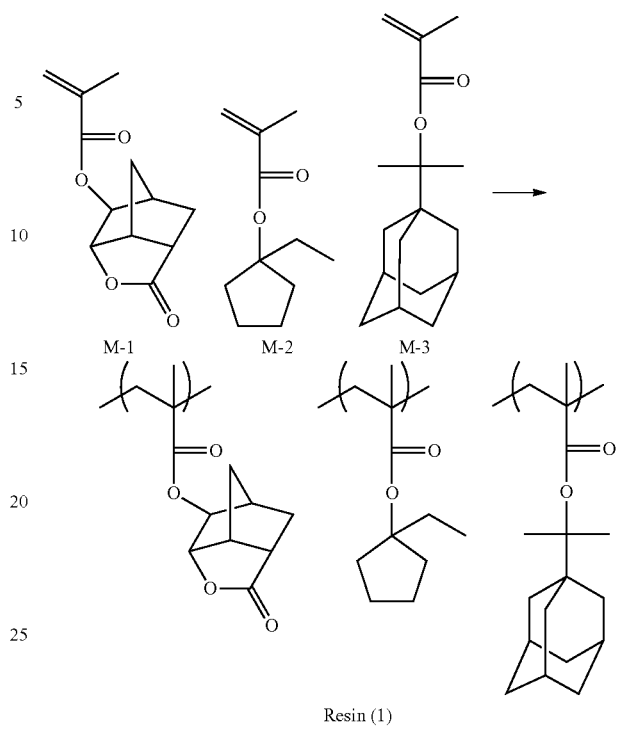

Resin (1)

<<Synthesis>>

8.5 g (42 mmol) of diphenylsulfoxide was added into a three-neck flask and dissolved in 40 g of phosphorus pentoxide-methanesulfonic acid solution (mass ratio of 1:10), and 5 g (46 mmol) of anisole was added dropwise to the reaction liquid at room temperature, using a funnel. During dropwise addition, the internal temperature was adjusted to 30° C. or lower. Further, the mixture was stirred at the internal temperature of 50° C. for 3 hours, the reaction liquid was added into a three-neck flask to which 200 g of iced water had been added, and then the mixture was stirred at room temperature for 10 minutes. Subsequently, 100 g of methylene chloride was added thereto, and then 8.5 g (20 mmol) of B1-5' was added to the mixture. The mixture was stirred at room temperature for 1 hour. The organic layer was separated, washed with 200 g of water, concentrated, and then purified by silica gel chromatography (developing solvent:ethyl acetate:methanol=90:10) to obtain 10.5 g (17 mmol) of a desired compound B1-5.

$^1$H-NMR, 400 MHz, δ (CDCl$_3$) ppm: 1.65-2.05 (15H, m), 3.93 (3H, s), 4.76 (2H, t), 4.37 (2H, brt), 4.44 (2H, td), 7.2 (2H, d), 7.58 (1H, t), 7.65-7.75 (10H, m), 7.78 (2H, d).

By the same synthesis method as the compound B1-5, a compound (B) described below was synthesized.

Synthesis Example 2: Synthesis of Resin (1)

102.3 parts by mass of cyclohexanone was heated at 80° C. under a nitrogen stream. While stirring this liquid, a mixed solution of 22.2 parts by mass of a monomer represented by the following structural formula M-1, 22.8 parts by mass of a monomer represented by the following structural formula M-2, 6.6 parts by mass of a monomer represented by the following structural formula M-3, 189.9 parts by mass of cyclohexanone, and 2.40 parts by mass of dimethyl 2,2'-azobisisobutyrate [V-601, manufactured by Wako Pure Chemical Industries, Ltd.] was added dropwise to the liquid for 5 hours. After completion of the dropwise addition, the mixture was further stirred at 80° C. for 2 hours. After being left to be cooled, the reaction liquid was reprecipitated with a large amount of hexane/ethyl acetate (mass ratio of 9:1) and filtered, and the obtained solid was dried in vacuum to obtain 41.1 parts by mass of an acid-decomposable resin (1).

The weight-average molecular weight (Mw: in terms of polystyrene) of the obtained resin (1), as determined by GPC (carrier: tetrahydrofuran (THF)) was Mw=9,500, and the dispersity was Mw/Mn=1.62. The compositional ratio measured by $^{13}$C-NMR was 40/50/10.

By carrying out the same operation as in Synthesis Example 2, the resins (1) to (12) described below were synthesized as an acid-decomposable resin.

<Manufacture of Resist>

The components shown in Table 3 described below were dissolved in a solvent to prepare a solution with a concentration of the solid content of 4% by mass of each of the components, and this solution was filtered through a polyethylene filter having a pore size of 0.05 μm to prepare an active-light-sensitive or radiation-sensitive resin composition. The active-light-sensitive or radiation-sensitive resin composition was evaluated by the following method and the results are shown in Table 3.

For each of the components in Table 1, the ratio in the case of using a plurality of the components is a mass ratio.

<Pattern Forming Method>

An organic antireflection film, ARC29SR (manufactured by Nissan Chemical Industries, Ltd.), was coated on a silicon wafer and baked at 205° C. for 60 seconds to form an antireflection film having a film thickness of 95 nm. Then, the active-light-sensitive or radiation-sensitive resin composition was coated thereon and baked (PB: Prebake) at 100° C. for 60 seconds to form a resist film having a film thickness of 100 nm.

The obtained wafer was subjected to pattern exposure through a 6% halftone mask having a 1:1 line-and-space pattern with a line width of 48 nm, using an ArF excimer laser liquid immersion scanner (manufactured by ASML; XT1700i, NA 1.20, C-Quad, outer sigma 0.900, inner sigma 0.812, and XY deflection). Further, ultrapure water was used as an immersion liquid. Thereafter, the wafer was heated (PEB: Post Exposure Bake) at 105° C. for 60 seconds. Then, the wafer was subjected to paddle development with a developer including an organic solvent for 30 seconds, and paddled and rinsed with a rinsing liquid [methylisobutyl carbinol (MIBC)] for 30 seconds. As the developer including an organic solvent, methyl amyl ketone was used in Example 16, and butyl acetate was used in Examples except for Example 16, and Comparative Examples. Subsequently, the wafer was rotated at a rotation speed of 4,000 rpm for 30 seconds to form a 1:1 line-and-space pattern with a line width of 48 nm.

<Evaluation> (Depth of Focus (DOF))

In the exposure dose for forming a line pattern with a line width of 50 nm under the exposure/development conditions in <Pattern Forming Method> above, exposure and development were carried out by changing the conditions of the exposure focus at an interval of 10 nm in the focus direction, the space line width (CD) of each of the obtained patterns was measured using a line-width critical dimension scanning electron microscope SEM (S-9380, Hitachi, Ltd.), and the minimum value or the maximum value in a curve obtained by plotting the respective CDs was defined as a best focus. When the focus was changed at a center of the best focus, a variation width of the focus with which a line width of 50 nm±10% was available, that is, a depth (nm) of focus was calculated. A higher value of the depth of focus is more preferable.

(LWR)

The line pattern (line width of 48 nm) with line/space=1/1 obtained in <Pattern Forming Method> above was observed using a line-width critical dimension scanning electron microscope SEM (S-9380, Hitachi, Ltd.). The line width was measured at 50 points in the range of an edge of 2 μm in the longitudinal direction of the line pattern, and the standard deviation for the measured deviation was determined to calculate 3σ. A smaller value thereof indicates better performance.

TABLE 3

| | Photoacid generator (B1) (g) | Photoacid generator (B2) (g) | Photoacid generator (RA) (g) | Resin (A) (10 g) | Basic compound (g) | Hydrophobic resin (0.05 g) | Solvent (mass ratio) | Surfactant (10 mg) | Evaluation item 1 LWR (nm) | Evaluation item 2 DOF (nm) |
|---|---|---|---|---|---|---|---|---|---|---|
| Example 1 | B1-1 (1.4) | B2-1 (1.1) | — | Resin (1) | D-1 (0.61) | 1b | A1/B2 = 80/20 | W-1 | 4.4 | 125 |
| Example 2 | B1-2 (1.1) | B2-2 (1.2) | — | Resin (2) | D-5 (0.31) | 2b | A1/A2 = 70/30 | None | 4.2 | 125 |
| Example 3 | B1-3 (1.2) | B2-3 (1.5) | — | Resin (3) | D-3 (0.30) | 3b | A1 | None | 4.5 | 125 |
| Example 4 | B1-4 (1.2) | B2-4 (1.5) | — | Resin (4) | D-4 (0.30) | 4b | A1 | W-3 | 4.2 | 140 |
| Example 5 | B1-5 (1.2) | B2-5 (1.5) | — | Resin (5) | D-2 (0.70) | 4b | A1/A2 = 70/30 | None | 4.2 | 140 |
| Example 6 | B1-6 (1.0) | B2-6 (1.1) | — | Resin (6) | D-6 (0.30) | 1b | A1/B1 = 80/20 | None | 4.3 | 140 |
| Example 7 | B1-7 (1.1) | B2-7 (1.5) | — | Resin (7) | D-4 (0.30) | 1b | A1/B1 = 90/10 | W-2 | 4.1 | 155 |
| Example 8 | B1-8 (1.2) | B2-8 (1.4) | — | Resin (8) | D-8 (0.30) | 3b | A1/B1 = 80/20 | None | 4.5 | 125 |
| Example 9 | B1-9 (1.2) | B2-9 (1.3) | — | Resin (9) | D-7 (0.30) | 3b | A1/A2 = 80/20 | None | 4.7 | 110 |
| Example 10 | B1-10 (1.3) | B2-10 (1.0) | — | Resin (10) | D-5 (0.31) | 1b | A1 | None | 4.5 | 155 |
| Example 11 | B1-11 (1.2) | B2-11 (1.3) | — | Resin (11) | D-5 (0.31) | 4b | A1 | None | 4.3 | 125 |
| Example 12 | B1-12 (1.2) | B2-12 (1.1) | — | Resin (12) | D-8 (0.30) | 4b | A1/A3 = 95/5 | W-1 | 4.4 | 140 |
| Example 13 | B1-5 (1.8) | — | RA-3 (0.9) | Resin (3) | D-2 (0.61) | 2b | A1 | W-1 | 4.7 | 110 |
| Example 14 | B1-6 (1.2) | — | RA-4 (1.0) | Resin (5) | D-5 (0.31) | 2b | A1 | W-4 | 4.8 | 100 |
| Example 15 | B1-5 (1.5) | B2-1 (1.2) | — | Resin (1) | D-1 (0.61) | 1b | A1/A2 = 80/20 | W-1 | 4.3 | 150 |
| Example 16 | B1-11 (1.2) | B2-11 (1.3) | — | Resin (1)/ Resin (11) (5 g/5 g) | D-5 (0.31) | 5b | A1 | None | 4.2 | 140 |
| Comparative Example 1 | — | — | RA-1 (3.0) | Resin (1) | D-1 (0.61) | 1b | A1/A2 = 80/20 | W-1 | 5.5 | 45 |
| Comparative Example 2 | — | B-9 (2.0) | — | Resin (1) | D-1 (0.61) | 1b | A1/A2 = 80/20 | W-1 | 5.7 | 75 |
| Comparative Example 3 | B1-3 (2.2) | — | — | Resin (1) | D-1 (0.61) | 1b | A1/A2 = 80/20 | W-1 | 5.4 | 60 |
| Comparative Example 4 | — | B-9 (1.7) | RA-2 (1.5) | Resin (1) | D-1 (0.61) | 1b | A1/A2 = 80/20 | W-1 | 5.2 | 75 |

Abbreviations in the Table as follows are used.

<Photoacid Generator (B)>

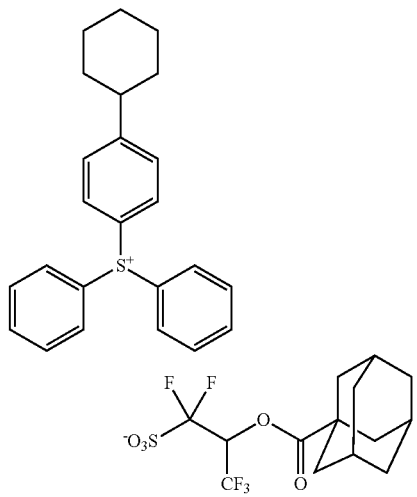

B1-1

B1-2
B1-3
B1-4
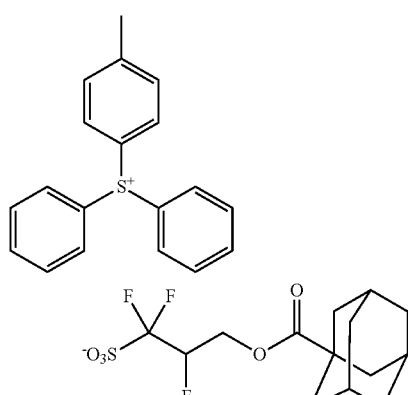
B1-5
B1-6
B1-7
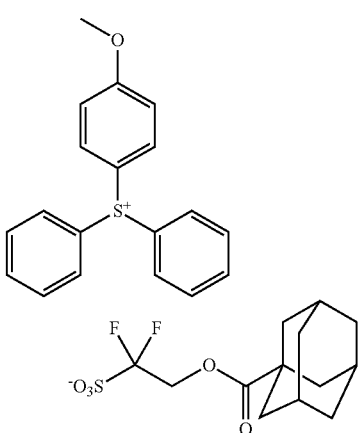
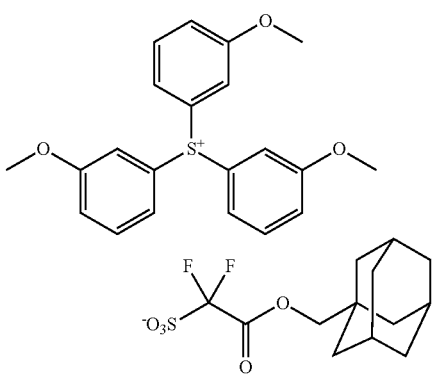
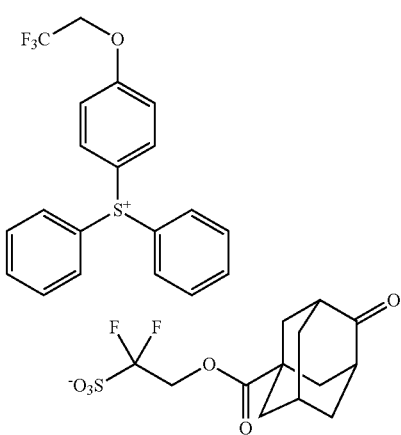

-continued
BI-8
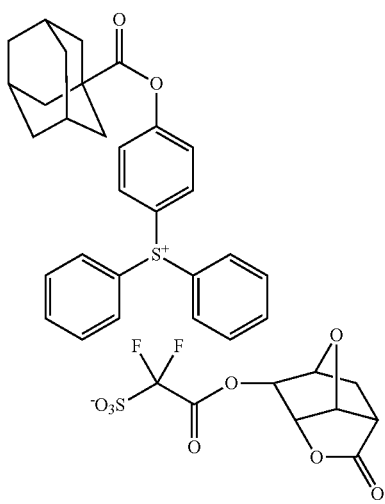
B1-9
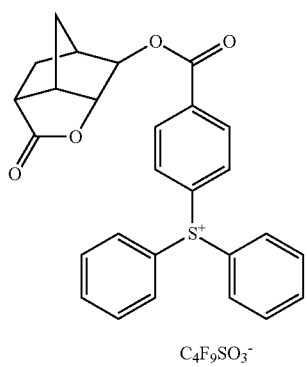
C₄F₉SO₃⁻
B1-10
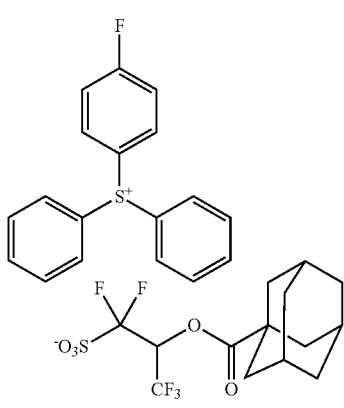
-continued
B1-11
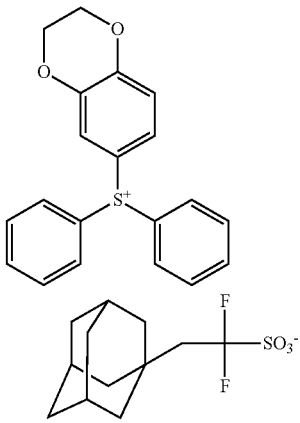
B1-12
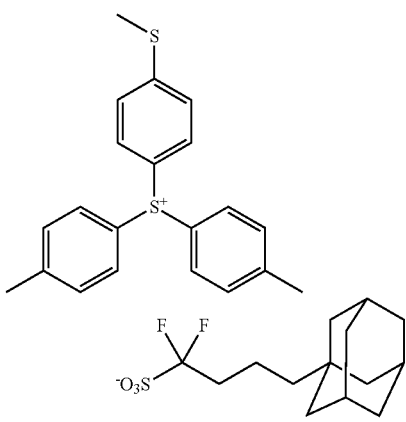
<Compound (B)>
B2-1
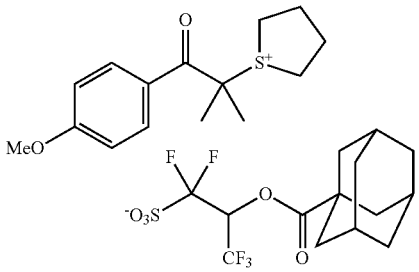
B2-2
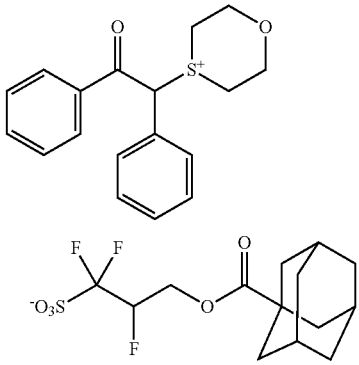

B2-3
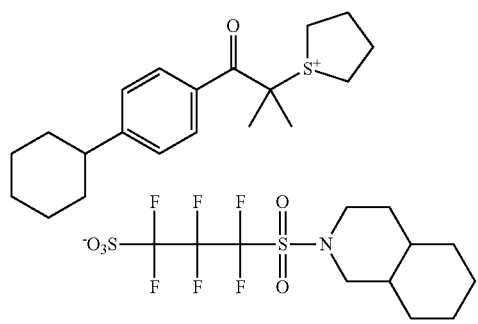
B2-4
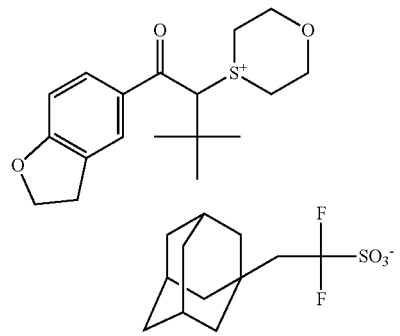
B2-5
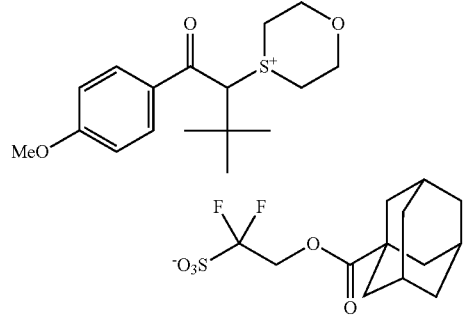
B2-6
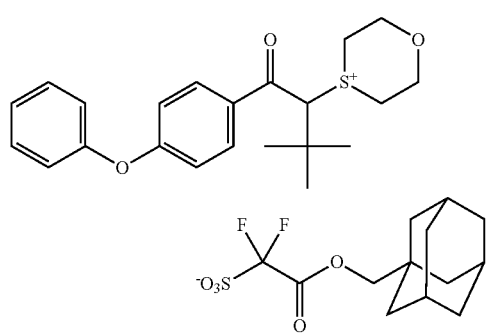
B2-7
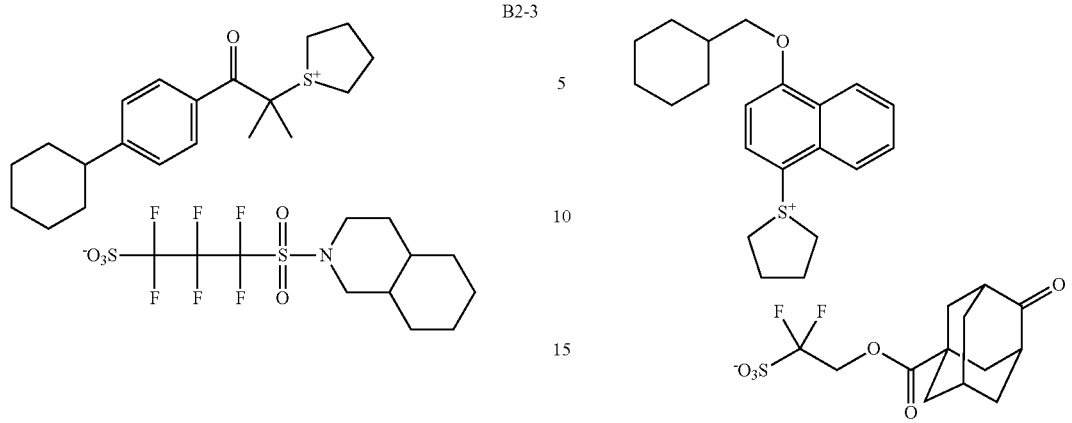
B2-8
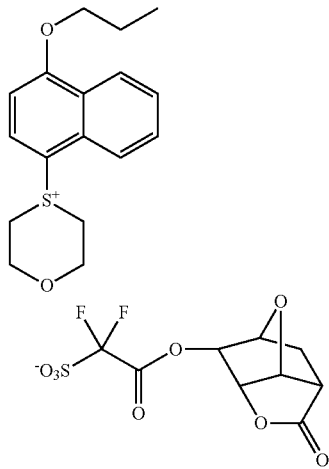
B2-9
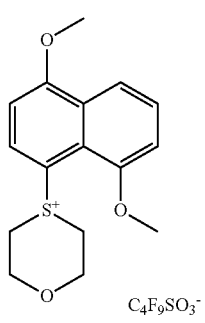
$C_4F_9SO_3^-$
B2-10
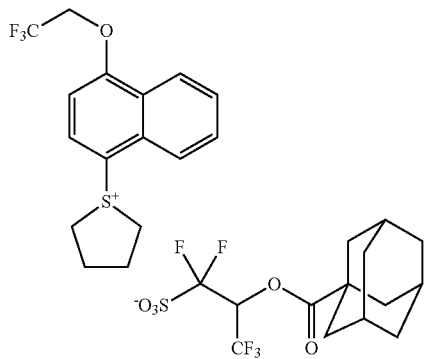

B2-11
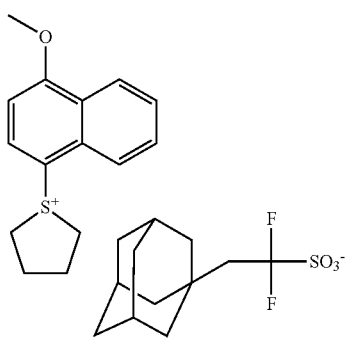
B2-12
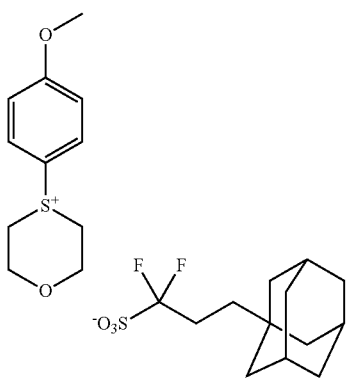
<Compound(RA)>
RA-1
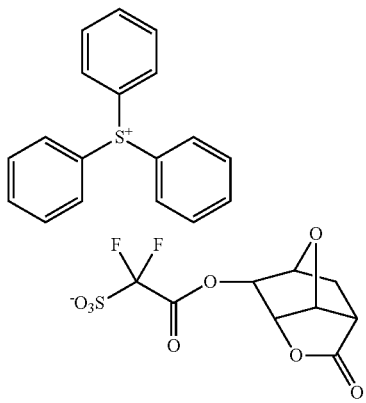
RA-2
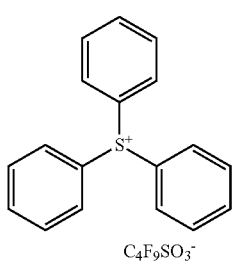
C₄F₉SO₃⁻
RA-3
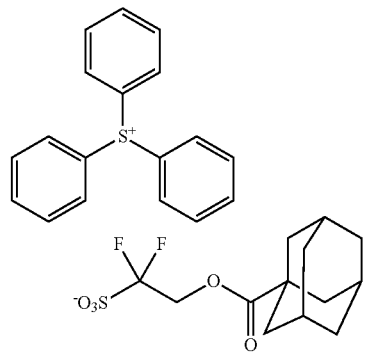
RA-4
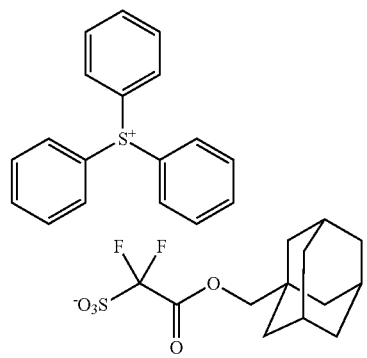
<Resin (A)>
Resin (1)
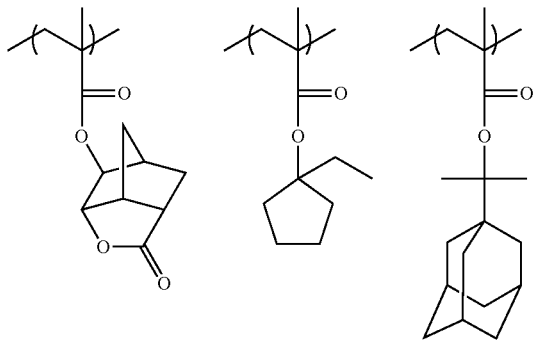
Resin (2)
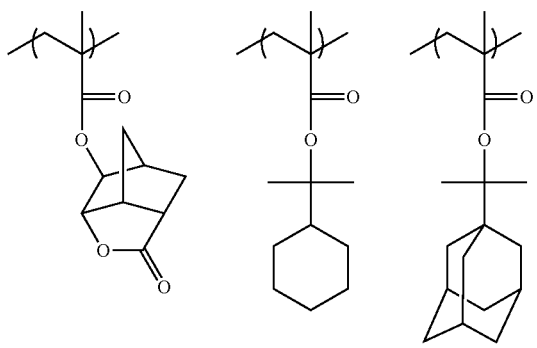

Resin (3)
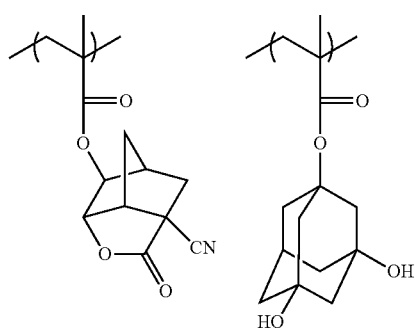
Resin (8)
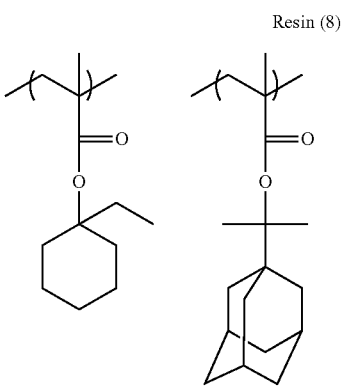
Resin (4)
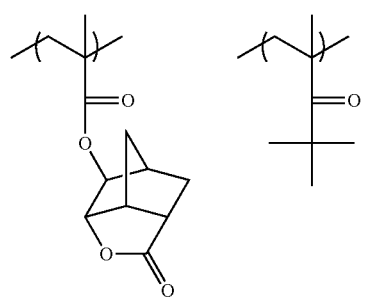
Resin (9)
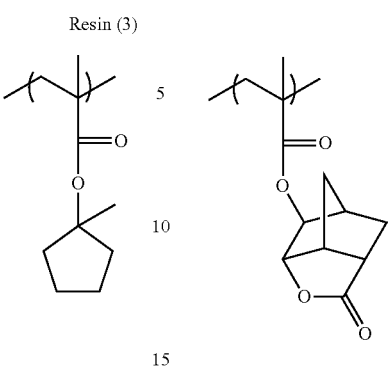
Resin (5)
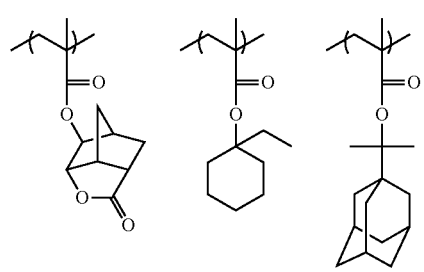
Resin (6)
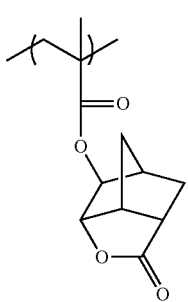
Resin (10)
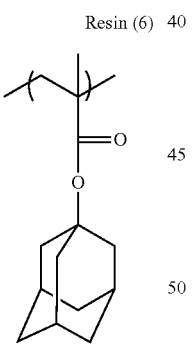
Resin (7)
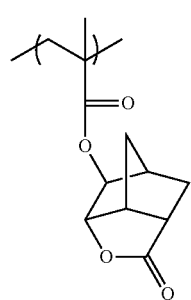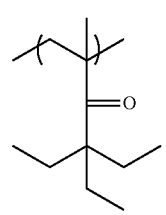
Resin (11)
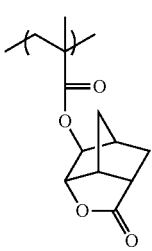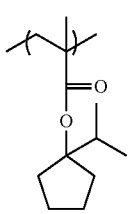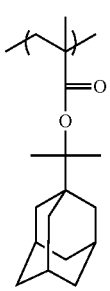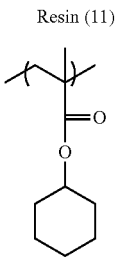

Resin (12)

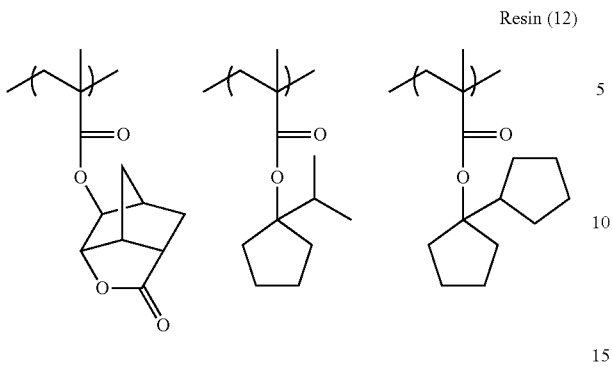

Furthermore, the compositional ratios (molar ratios; corresponding to the repeating units in order from the left side), the weight-average molecular weights (Mw), and the dispersities (Mw/Mn) of the repeating units are shown in Table 4 below. These were determined by the same methods as for the resin (1) as described above.

TABLE 4

| No. | Compositional ratio (% by mole) | | | | Mw | Mw/Mn |
|---|---|---|---|---|---|---|
| Resin (1) | 40 | 50 | 10 | — | 9,500 | 1.62 |
| Resin (2) | 40 | 40 | 20 | — | 17,000 | 1.70 |
| Resin (3) | 45 | 5 | 50 | — | 11,000 | 1.63 |
| Resin (4) | 40 | 60 | — | — | 15,000 | 1.66 |
| Resin (5) | 40 | 40 | 10 | 10 | 10,500 | 1.62 |
| Resin (6) | 40 | 50 | 10 | — | 15,500 | 1.68 |
| Resin (7) | 40 | 60 | — | — | 11,000 | 1.65 |
| Resin (8) | 40 | 40 | 20 | — | 10,000 | 1.64 |
| Resin (9) | 40 | 50 | 10 | — | 9,000 | 1.60 |
| Resin (10) | 40 | 60 | — | — | 10,000 | 1.61 |
| Resin (11) | 40 | 40 | 10 | 10 | 8,500 | 1.60 |
| Resin (12) | 40 | 40 | 20 | — | 9,500 | 1.61 |

<Basic Compound Whose Basicity is Reduced or Lost Upon Irradiation with Active Light or Radiation, and Nitrogen Atom-Containing Basic Compound>

As the basic compound whose basicity is reduced or lost upon irradiation with active light or radiation or the basic compound containing a nitrogen atom, the following compounds were used.

D-1

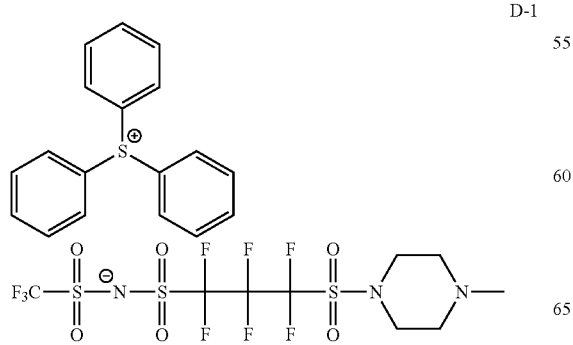

D-2

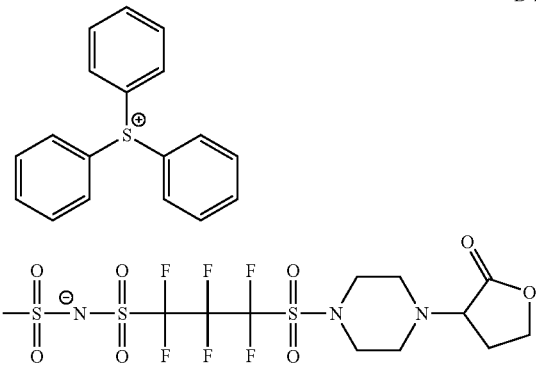

D-3

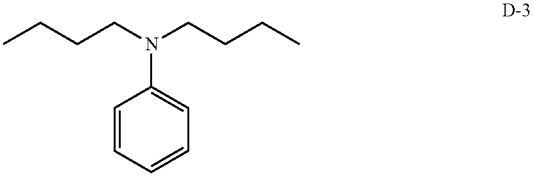

D-4

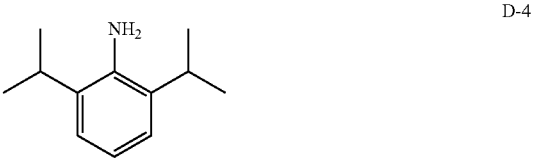

D-5

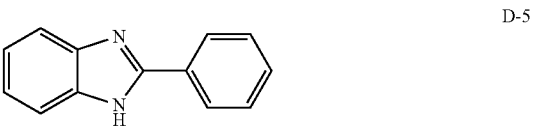

D-6

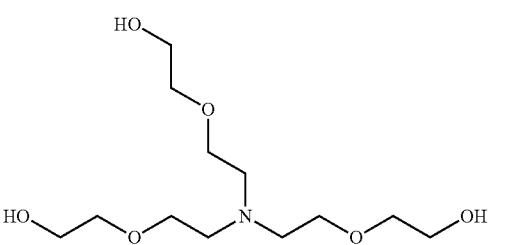

D-7

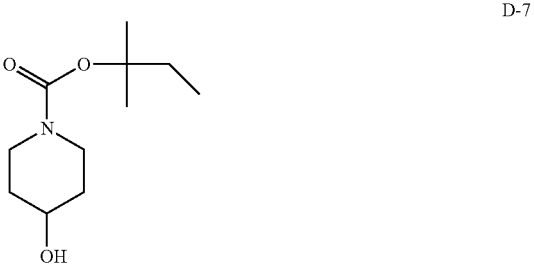

-continued

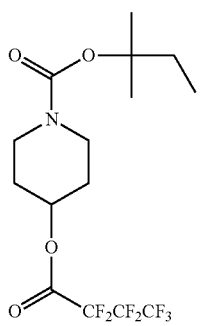
D-8

<Hydrophobic Resin>
As the hydrophobic resin, the following resins were used.

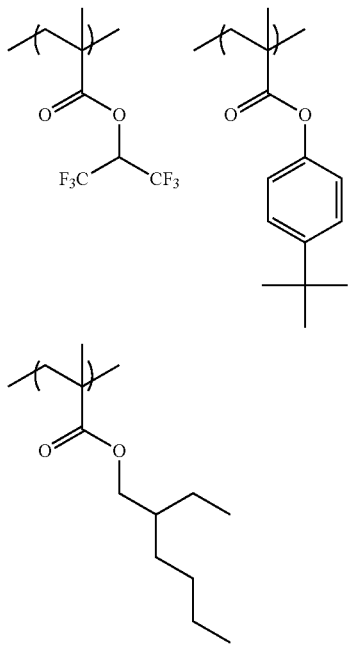
(1b)

(2b)

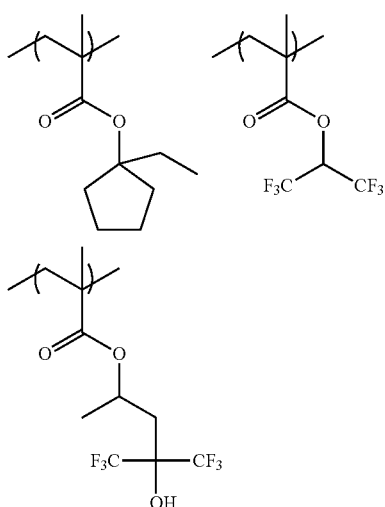

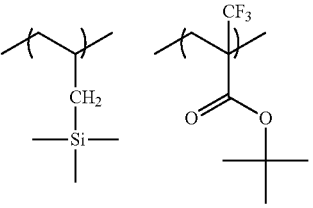
(3b)

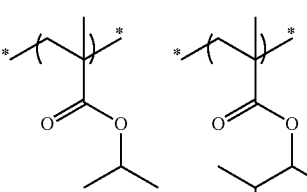
(4b)

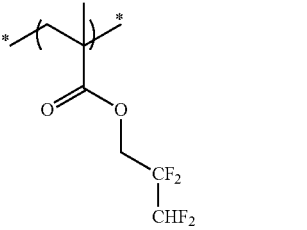

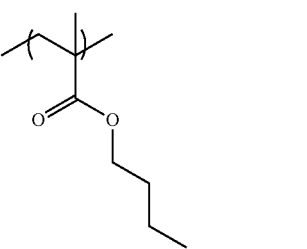
(5b)

The compositional ratios (molar ratios; corresponding to the repeating units in order from the left side), the weight-average molecular weights (Mw), and the dispersities (Mw/Mn) of the repeating units are shown in Table 5. These were determined by the same methods as for the resin (1) as described below.

TABLE 5

| No. | Compositional ratio (% by mole) | | | | Mw | Mw/Mn |
|---|---|---|---|---|---|---|
| Resin (1b) | 50 | 45 | 5 | — | 7,000 | 1.30 |
| Resin (2b) | 40 | 40 | 20 | — | 18,600 | 1.57 |
| Resin (3b) | 50 | 50 | — | — | 25,400 | 1.63 |
| Resin (4b) | 30 | 65 | 5 | — | 28,000 | 1.70 |
| Resin (5b) | 100 | — | — | — | 12,500 | 1.65 |

<Surfactant>
W-1: MEGAFACE F176 (manufactured by DIC, Inc.; fluorine-based)
W-2: MEGAFACE R08 (manufactured by DIC, Inc.; fluorine- and silicon-based)
W-3: PF6320 (manufactured by OMNOVA Solutions Inc.; fluorine-based)
W-4: TROYSOL S-366 (manufactured by Troy Chemical Co., Ltd.)
[Solvent]
A1: Propylene glycol monomethyl ether acetate (PG-MEA)

A2: Cyclohexanone
A3: γ-Butyrolactone
B1: Propylene glycol monomethyl ether (PGME)
B2: Ethyl lactate

What is claimed is:

1. An active-light-sensitive or radiation-sensitive resin composition comprising:
a resin (A); and
a photoacid generator (B) capable of generating an acid upon irradiation with active light or radiation,
wherein the active-light-sensitive or radiation-sensitive resin composition contains at least a photoacid generator (B1) represented by the following General Formula (1) and a photoacid generator (B2) other than the photoacid generator (B1) as the photoacid generator (B),

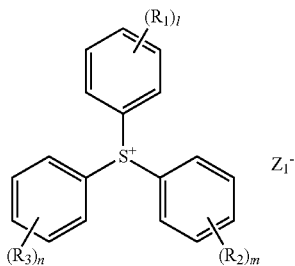

(1)

in General Formula (1),
$R_1$, $R_2$, and $R_3$ each independently represent a halogen atom, an alkyl group, a cycloalkyl group, an alkoxy group, an alkylcarbonyloxy group, an alkyloxycarbonyl group, an alkylthio group, a cycloalkylcarbonyloxy group, a cycloalkyloxycarbonyl group, or a cycloalkylthio group,
l, m, and n each independently represent an integer of 0 to 3, and l+m+n is 1 or more;
when l is 2 or more, a plurality of $R_1$'s may be the same as or different from each other, and at least two $R_1$'s may be bonded to each other to form a ring, provided that the ring is not an aromatic hydrocarbon group;
when m is 2 or more, a plurality of $R_2$'s may be the same as or different from each other, and at least two $R_2$'s may be bonded to each other to form a ring, provided that the ring is not an aromatic hydrocarbon group; and
when n is 2 or more, a plurality of $R_3$'s may be the same as or different from each other, and at least two $R_3$'s may be bonded to each other to form a ring, provided that the ring is not an aromatic hydrocarbon group, and
$Z_1^-$ represents a non-nucleophilic anion, and
wherein the photoacid generator (B2) is a compound represented by the following General Formula (ZI-3),

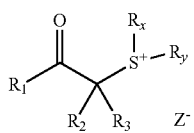

(ZI-3)

in General Formula (ZI-3),
$R_1$ represents an alkyl group, a cycloalkyl group, an alkoxy group, a cycloalkoxy group, an aryl group, or an alkenyl group,
$R_2$ and $R_3$ each independently represent a hydrogen atom, an alkyl group, a cycloalkyl group, or an aryl group, and $R_2$ and $R_3$ may be linked to each other to form a ring,
$R_1$ and $R_2$ may be bonded to each other to form a ring,
$R_X$ and $R_Y$ each independently represent an alkyl group, a cycloalkyl group, an alkenyl group, an aryl group, a 2-oxoalkyl group, a 2-oxocycloalkyl group, an alkoxycarbonylalkyl group, or an alkoxycarbonylcycloalkyl group; and $R_X$ and $R_Y$ may be linked to each other to form a ring, and this ring structure may include an oxygen atom, a nitrogen atom, a sulfur atom, a ketone group, an ether bond, an ester bond, or an amide bond, and
$Z^-$ represents a non-nucleophilic anion represent by the following General Formula (2),

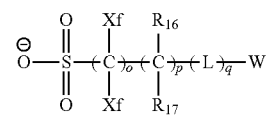

(2)

in General Formula (2),
Xf's each independently represent a fluorine atom or an alkyl group substituted with at least one fluorine atom.
$R_{16}$ and $R_{17}$ each independently represent a hydrogen atom, a fluorine atom, an alkyl group, or an alkyl group substituted with at least one fluorine atom, and in the case where $R_{16}$ and $R_{17}$ are present in plural numbers, they may be the same as or different from each other,
L represents a divalent linking group, and in the case where L's are present in plural numbers, they may be the same as or different from each other,
W represents an organic group including a cyclic structure,
o represents an integer of 1 to 20,
p represents an integer of 0 to 10, and
q represents an integer of 0 to 10

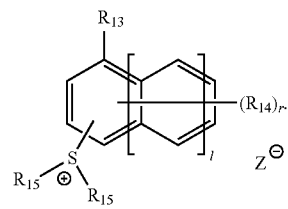

(ZI-4)

2. The active-light-sensitive or radiation-sensitive resin composition according to claim 1, wherein $Z_1^-$ in General Formula (1) is a non-nucleophilic anion represented by the following General Formula (2),

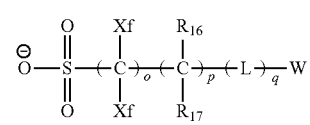

(2)

in General Formula (2),

X'fs each independently represent a fluorine atom or an alkyl group substituted with at least one fluorine atom, $R_{16}$ and $R_{17}$ each independently represent a hydrogen atom, a fluorine atom, an alkyl group, or an alkyl group substituted with at least one fluorine atom, and in the case where $R_{16}$ and $R_{17}$ are present in plural numbers, they may be the same as or different from each other, L represents a divalent linking group, and in the case where L's are present in plural numbers, they may be the same as or different from each other, W represents an organic group including a cyclic structure, o represents an integer of 1 to 20, p represents an integer of 0 to 10, and q represents an integer of 0 to 10.

3. The active-light-sensitive or radiation-sensitive resin composition according to claim 1, wherein the content of the photoacid generator (B) is 10% by mass or more with respect to the total solid content in the composition.

4. The active-light-sensitive or radiation-sensitive resin composition according to claim 1, wherein the resin (A) is a resin which decomposes by the action of an acid to increase the polarity thereof.

5. The active-light-sensitive or radiation-sensitive resin composition according to claim 1, further comprising a basic compound having a nitrogen atom or a basic compound whose basicity decreases or is lost upon irradiation with active light or radiation.

6. An active-light-sensitive or radiation-sensitive film formed by using the active-light-sensitive or radiation-sensitive resin composition according to claim 1.

7. The active-light-sensitive or radiation-sensitive resin composition according to claim 1, wherein in General Formula (1):

when l is 2 or more, at least two $R_1$'s are not bonded to each other to form a ring;

when m is 2 or more, at least two $R_2$'s are not bonded to each other to form a ring; and when n is 2 or more, at least two $R_3$'s are not bonded to each other to form a ring.

8. A pattern forming method comprising:

a step of forming an active-light-sensitive or radiation-sensitive film using the active-light-sensitive or radiation-sensitive resin composition according to claim 1;

a step of exposing the active-light-sensitive or radiation-sensitive film; and a step of developing the exposed active-light-sensitive or radiation-sensitive film.

9. The pattern forming method according to claim 8, wherein the exposing step is liquid immersion exposure.

10. The pattern forming method according to claim 9, wherein the developer used in the developing step is a developer containing an organic solvent.

11. A method for manufacturing an electronic device, comprising the pattern forming method according to claim 9.

12. An active-light-sensitive or radiation-sensitive resin composition comprising:

a resin (A); and a photoacid generator (B) capable of generating an acid upon irradiation with active light or radiation, wherein the active-light-sensitive or radiation-sensitive resin composition contains at least a photoacid generator (B1) represented by the following General Formula (1) and a photoacid generator (B2) other than the photoacid generator (B1) as the photoacid generator (B),

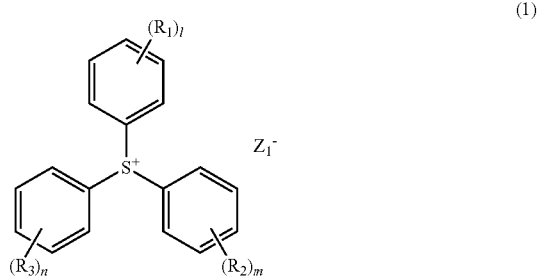

in General Formula (1), $R_1$, $R_2$, and $R_3$ each independently represent a halogen atom, an alkyl group, a cycloalkyl group, an alkoxy group, an alkylcarbonyloxy group, an alkyloxycarbonyl group, an alkylthio group, a cycloalkylcarbonyloxy group, a cycloalkyloxycarbonyl group, or a cycloalkylthio group, l, m, and n each independently represent an integer of 0 to 3, and l+m+n is 1 or more;

when l is 2 or more, a plurality of $R_1$'s may be the same as or different from each other, and at least two $R_1$'s may be bonded to each other to form a ring, provided that the ring is not an aromatic hydrocarbon group;

when m is 2 or more, a plurality of $R_2$'s may be the same as or different from each other, and at least two $R_2$'s may be bonded to each other to form a ring, provided that the ring is not an aromatic hydrocarbon group; and when n is 2 or more, a plurality of $R_3$'s may be the same as or different from each other, and at least two $R_3$'s may be bonded to each other to form a ring, provided that the ring is not an aromatic hydrocarbon group, and $Z1^-$ represents a non-nucleophilic anion, and wherein the photoacid generator (B2) is a compound represented by the following General Formula (ZI-4),

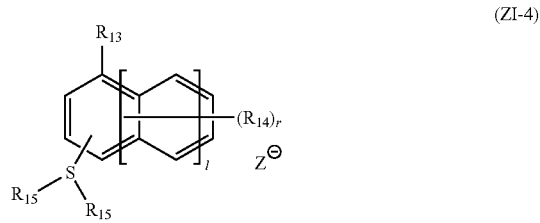

in General Formula (ZI-4), $R_{13}$ represents a hydrogen atom, a fluorine atom, a hydroxyl group, an alkyl group, a cycloalkyl group, an alkoxy group, an alkoxycarbonyl group, or a group having a cycloalkyl group, in the case where $R_{14}$'s are present in plural numbers, they each independently represent a hydroxyl group, an alkyl group, a cycloalkyl group, an alkoxy group, an alkoxycarbonyl group, an alkylcarbonyl group, an alkylsulfonyl group, a cycloalkylsulfonyl group, or a group having a cycloalkyl group, $R_{15}$'s each independently represent an alkyl group, a cycloalkyl group, or a naphthyl group; two $R_{15}$'s may be bonded to each other to form a ring together with a sulfur atom in the formula, and may further include a hetero atom, in addition to a sulfur atom in the formula, as an atom constituting the ring, l represents an integer of 0 to 2, r represents an integer of 0 to 8, and $Z^-$ represents a non-nucleophilic anion.

13. The active-light-sensitive or radiation-sensitive resin composition according to claim 12, wherein $Z^-$ in General Formula (ZI-4) is a non-nucleophilic anion represented by the following General Formula (2),

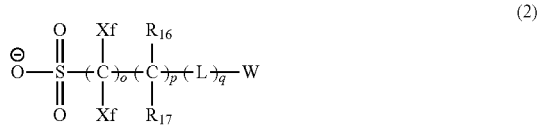

in General Formula (2),

Xf's each independently represent a fluorine atom or an alkyl group substituted with at least one fluorine atom, $R_{16}$ and $R_{17}$ each independently represent a hydrogen atom, a fluorine atom, an alkyl group, or an alkyl group substituted with at least one fluorine atom, and in the case where $R_{16}$ and $R_{17}$ are present in plural numbers, they may be the same as or different from each other, L represents a divalent linking group, and in the case where L's are present in plural numbers, they may be the same as or different from each other, W represents an organic group including a cyclic structure, o represents an integer of 1 to 20, p represents an integer of 0 to 10, and q represents an integer of 0 to 10.

14. The active-light-sensitive or radiation-sensitive resin composition according to claim 12, wherein $Z_1^-$ in General Formula (1) is a non-nucleophilic anion represented by the following General Formula (2),

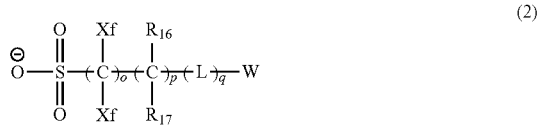

in General Formula (2),

Xf's each independently represent a fluorine atom or an alkyl group substituted with at least one fluorine atom, $R_{16}$ and $R_{17}$ each independently represent a hydrogen atom, a fluorine atom, an alkyl group, or an alkyl group substituted with at least one fluorine atom, and in the case where $R_{16}$ and $R_{17}$ are present in plural numbers, they may be the same as or different from each other, L represents a divalent linking group, and in the case where L's are present in plural numbers, they may be the same as or different from each other, W represents an organic group including a cyclic structure, o represents an integer of 1 to 20, p represents an integer of 0 to 10, and q represents an integer of 0 to 10.

15. The active-light-sensitive or radiation-sensitive resin composition according to claim 12, wherein the content of the photoacid generator (B) is 10% by mass or more with respect to the total solid content in the composition.

16. The active-light-sensitive or radiation-sensitive resin composition according to claim 12, wherein the resin (A) is a resin which decomposes by the action of an acid to increase the polarity thereof.

17. The active-light-sensitive or radiation-sensitive resin composition according to claim 12, further comprising a basic compound having a nitrogen atom or a basic compound whose basicity decreases or is lost upon irradiation with active light or radiation.

18. An active-light-sensitive or radiation-sensitive film formed by using the active-light-sensitive or radiation-sensitive resin composition according to claim 12.

19. A pattern forming method comprising:
a step of forming an active-light-sensitive or radiation-sensitive film using the active-light-sensitive or radiation-sensitive resin composition according to claim 12;
a step of exposing the active-light-sensitive or radiation-sensitive film; and
a step of developing the exposed active-light-sensitive or radiation-sensitive film.

20. The pattern forming method according to claim 19, wherein the exposing step is liquid immersion exposure.

21. The pattern forming method according to claim 19, wherein the developer used in the developing step is a developer containing an organic solvent.

22. A method for manufacturing an electronic device, comprising the pattern forming method according to claim 19.

23. The active-light-sensitive or radiation-sensitive resin composition according to claim 12, wherein in General Formula (1):
when l is 2 or more, at least two $R_1$'s are not bonded to each other to form a ring;
when m is 2 or more, at least two $R_2$'s are not bonded to each other to form a ring; and
when n is 2 or more, at least two $R_3$'s are not bonded to each other to form a ring.

* * * * *